(12) United States Patent
Bonnert et al.

(10) Patent No.: US 8,524,715 B2
(45) Date of Patent: Sep. 3, 2013

(54) PHENOXYACETIC ACID DERIVATIVES USEFUL FOR TREATING RESPIRATORY DISEASES

(75) Inventors: Roger Victor Bonnert, Leicestershire (GB); Lilian Alcaraz, Leicestershire (GB); Rukhsana Tasneem Mohammed, Leicestershire (GB); Anthony Ronald Cook, Leicestershire (GB); Stephen Thom, Leicestershire (GB); Timothy Jon Luker, Leicestershire (GB)

(73) Assignee: Astrazeneca AB, Sodertalje (SE)

( * ) Notice: Subject to any disclaimer, the term of this patent is extended or adjusted under 35 U.S.C. 154(b) by 1404 days.

(21) Appl. No.: 11/719,832

(22) PCT Filed: Nov. 22, 2005

(86) PCT No.: PCT/GB2005/004464
§ 371 (c)(1),
(2), (4) Date: May 21, 2007

(87) PCT Pub. No.: WO2006/056752
PCT Pub. Date: Jun. 1, 2006

(65) Prior Publication Data
US 2009/0149448 A1    Jun. 11, 2009

(30) Foreign Application Priority Data

Nov. 23, 2004 (GB) ................................. 0425673.1
Apr. 30, 2005 (GB) ................................. 0508923.0

(51) Int. Cl.
*A61K 31/497* (2006.01)
*C07D 295/00* (2006.01)

(52) U.S. Cl.
USPC .................................... 514/252.12; 544/383

(58) Field of Classification Search
None
See application file for complete search history.

(56) References Cited

U.S. PATENT DOCUMENTS

| | | | |
|---|---|---|---|
| 3,278,524 A | 10/1966 | Johnson et al. | |
| 3,920,846 A | 11/1975 | Hanauye et al. | |
| 3,985,779 A | 10/1976 | Tanaka et al. | |
| 4,234,742 A | 11/1980 | Cognacq et al. | |
| 4,248,618 A | 2/1981 | Serban et al. | |
| 4,670,566 A | 6/1987 | Walsh et al. | |
| 5,006,542 A | 4/1991 | Hall et al. | |
| 5,145,790 A | 9/1992 | Mattingly et al. | |
| 5,411,972 A * | 5/1995 | Komoto et al. | 514/330 |
| 5,413,891 A | 5/1995 | Matsuura et al. | |
| 5,532,371 A * | 7/1996 | Komoto et al. | 544/360 |
| 5,703,099 A | 12/1997 | Hamanaka et al. | |
| 6,150,413 A | 11/2000 | Bernardon et al. | |
| 6,376,546 B1 | 4/2002 | Shoda et al. | |
| 6,417,212 B1 | 7/2002 | Brooks et al. | |
| 7,056,942 B2 * | 6/2006 | Hildesheim et al. | 514/411 |
| 7,067,507 B2 * | 6/2006 | Pulley et al. | 514/183 |
| 7,737,135 B2 | 6/2010 | Luker et al. | |
| 2004/0029933 A1 | 2/2004 | Zhao et al. | |
| 2004/0097555 A1 | 5/2004 | Ohkawa et al. | |
| 2004/0220237 A1 | 11/2004 | Fu et al. | |
| 2005/0239881 A1 | 10/2005 | Dunn et al. | |
| 2006/0211765 A1 | 9/2006 | Pairaudeau et al. | |
| 2006/0264435 A1 | 11/2006 | Bonnert et al. | |
| 2006/0293352 A1 | 12/2006 | Bonnert et al. | |
| 2007/0249686 A1 | 10/2007 | Bonnert et al. | |
| 2008/0114002 A1 | 5/2008 | Bonnert et al. | |
| 2008/0132480 A1 | 6/2008 | Luker et al. | |
| 2008/0255150 A1 | 10/2008 | Luker | |
| 2008/0293775 A1 | 11/2008 | Bonnert et al. | |
| 2009/0012151 A1 | 1/2009 | Bonnert et al. | |
| 2009/0036535 A1 | 2/2009 | Luker et al. | |
| 2009/0149448 A1 | 6/2009 | Alcaraz et al. | |
| 2009/0192163 A1 | 7/2009 | Luker et al. | |
| 2010/0160285 A1 | 6/2010 | Luker et al. | |

FOREIGN PATENT DOCUMENTS

| | | |
|---|---|---|
| CH | 432119 | 9/1967 |
| EP | 0006789 | 1/1980 |
| EP | 0114734 | 8/1984 |
| EP | 0455058 | 11/1991 |
| EP | 0540165 | 5/1993 |
| EP | 0622690 | 11/1994 |
| EP | 0622816 | 11/1994 |
| EP | 0839808 | 5/1998 |
| EP | 1012142 | 6/2000 |
| EP | 1170594 | 1/2002 |
| EP | 1211513 | 6/2002 |
| EP | 1471057 | 10/2004 |
| GB | 690816 | 4/1953 |
| GB | 1 356 834 | 6/1974 |
| GB | 1 464 977 | 2/1977 |

(Continued)

OTHER PUBLICATIONS

Ebenezer et al. Expert Opinion on Therapeutic Patents, 2007, 17(9), 1131-45.*

(Continued)

Primary Examiner — Noble Jarrell

(57) ABSTRACT

The invention relates to substituted phenoxyacetic acids as useful pharmaceutical compounds for treating respiratory disorders, pharmaceutical compositions containing them, and processes for their preparation.

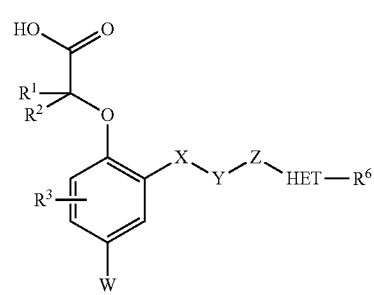

(I)

11 Claims, No Drawings

(56) References Cited

FOREIGN PATENT DOCUMENTS

| | | |
|---|---|---|
| GB | 1 469 687 | 4/1977 |
| GB | 2 031 408 | 4/1980 |
| GB | 2 041 363 | 9/1980 |
| GB | 1 585 963 | 3/1981 |
| JP | 07140725 | 6/1995 |
| JP | 2003-508389 | 3/2003 |
| JP | 2006-521382 | 9/2006 |
| JP | 2006-522117 | 9/2006 |
| WO | WO 93/12086 * | 6/1993 |
| WO | WO 97/08126 | 3/1997 |
| WO | WO 98/03164 | 1/1998 |
| WO | WO 99/11605 | 3/1999 |
| WO | WO 99/11627 | 3/1999 |
| WO | WO 01/16120 | 3/2001 |
| WO | WO 01/60807 | 8/2001 |
| WO | WO 01/81312 | 11/2001 |
| WO | WO 01/92224 | 12/2001 |
| WO | WO 03/064387 | 8/2003 |
| WO | WO 03/066047 | 8/2003 |
| WO | WO 03/068744 | 8/2003 |
| WO | WO 03/097042 | 11/2003 |
| WO | WO 03/097598 | 11/2003 |
| WO | WO 03/101961 | 12/2003 |
| WO | WO 2004/007451 | 1/2004 |
| WO | WO 2004/048314 | 6/2004 |
| WO | WO 2004/058164 | 7/2004 |
| WO | WO 2004/089884 | 10/2004 |
| WO | WO 2004/089885 | 10/2004 |
| WO | WO 2004/094386 | 11/2004 |
| WO | WO 2004/096777 | 11/2004 |
| WO | WO 2005/018529 | 3/2005 |
| WO | WO 2005/044260 | 5/2005 |
| WO | WO 2005/105727 | 11/2005 |
| WO | WO 2005/115382 | 12/2005 |
| WO | WO 2006/005909 | 1/2006 |
| WO | WO 2006/021759 | 3/2006 |
| WO | WO 2006/037982 | 4/2006 |
| WO | WO 2006/056752 | 6/2006 |
| WO | WO 2006/125596 | 11/2006 |
| WO | WO 2007/039736 | 4/2007 |
| WO | WO 2007/039741 | 4/2007 |
| WO | WO 2007/052023 | 5/2007 |
| WO | WO 2007/068894 | 6/2007 |

OTHER PUBLICATIONS

Ono Pharm. Co. Ltd. Expert Opinion on Therapeutic Patents, 2003, 13(10), 1657-1661.*
AstraZeneca AB. Expert Opinion on Therapeutic Patents, 2004, 14(1), 125-128.*
"Prevention Asthma Symptoms", http://www.webmd.com/asthma/guide/asthma-prevention, accessed Apr. 23, 2010.*
"Allergic Rhinitis-Prevention", http://www.webmd.com/allergies/tc/allergic-rhinitis-prevention, accessed Apr. 23, 2010.*
"COPD treatments", http://www.webmd.com/lung/copd/copd-treatments-improving-your-quality-of-life, accessed Apr. 23, 2010.*
Wermuth. The Practice of Medicinal Chemistry, 1996, chapter 13, pp. 203-3.*
"DialogWeb Records", http://www.dialogweb.com/cgi/document?req=1284661379410, accessed Sep. 16, 2010.*
Amin et al., "The Fries Reaction: Part VI—the rearrangement of aryl p-toluene-sulphonates & a convenient method for synthesis of hydroxy-diarylsulphones", *Journal of Scientific Industrial Research*, vol. 13B, 1954, pp. 181-183.
Atkinson et al., "Substituted (2-Phenoxyphenyl)acetic Acids with Antiinflammatory Activity", *J. Med. Chem.*, vol. 26, 1983, pp. 1353-1360.
Baliah et al., "Fries rearrangement of the benzenesulphonates of xylenols", *Recueil des Travaux Chimiques des Pays-Bas*, vol. 80, 1961, pp. 139-148.
Bartl et al., "Thioxanthene Derivatives of Pharmacological Interest: 1,2,4-Trichloro and 2,4,5,6-Tetrachloro Derivatives of 9-(3-Dimethylaminopropylidene)Thioxanthene", *Collection Czechoslov. Chem. Commun.*, vol. 49, 1984, pp. 2295-2308.

Brown et al., "Some Chlorinated Hydroxyphenoxyacetic Acids", *Journal of the Chemical Society*, 1955, pp. 3681-3687.
Budavari, S., "The merck Index, 13$^{th}$ edition", p. 3106, monograph 3108, XP-002347170, 2001.
Cavill et al., "The chemistry of plant-growth regulators. Part I. 2:4-dichloro-6-hydroxyphenoxyacetic acid and related compounds", *Journal of the Chemical Society*, 1954, pp. 565-569.
*Cecil Textbook of Medicine*, 20$^{th}$ ed. (1996), vol. 2, pp. 1992-1996.
*Cecil Textbook of Medicine*, 20$^{th}$ ed. (1996), vol. 2, pp. 2050-2057.
Clemo et al., "Strychnine and brucine. Part II", *Journal of the Chemical Society*, vol. 125, 1924, pp. 1751-1804, XP008053173.
Cocco et al., "Annulation of functionalized hexadienones as an efficient regioselective approach to N-Aryl-2-(trifluoromethyl)-4-pyridinamines", *Tetrahedron Letters*, vol. 40, No. 23, 1999, pp. 4407-4410.
FDA mulls drug to slow late-stage Alzheimer's [online], [retrieved Sep. 24, 2003]. Retrieved from the Internet, URL; http://www.cnn.com/2003/HEALTH/conditions/09/24/alzheimers.drug.ap/index.html>.
Gallo et al., "Spirodioxolanonarenones. II. Synthesis of a halogenated 1,4-dioxaspiro[4,5]deca-7,9-diene-2,6-dione", *Journal of Chemistry*, vol. 30, No. 5, 1965, pp. 1657-1658.
Gaunt et al., "Metabolism of 4-chloro-2-methylphenoxyacetate by a soil pseudomonad", *Biochem. J.*, vol. 122, 1971, pp. 519-526.
Hazeldine et al., "Design, Synthesis and Biological Evaluation of Analogues of the Antitumor Agent, 2-{4-[(7-Chloro-2-quinoxalinyl)oxy]phenoxy}propionic Acid (XK469)", *J. Med. Chem.*, vol. 44, 2001, pp. 1758-1776.
Huston et al., "Chloro derivatives of o- and p-benzyl phenols: II. Some monochloro, dichloro and trichloro derivatives of ortho and para benzyl phenols", *Journal of the American Chemical Society*, vol. 55, No. 11, 1933, pp. 4639-4643.
Inukai et al., "*ortho*-Disubstituted *F*-benzenes. III. Preparation of (*F*-benzo)heterocyclic compounds from *F*-benzoic acid and *F*-phenol, and the reactions of some intermediary *F*-benzoyl- and F-phenoxy compounds", *Bull. Chem. Soc. Jpn.*, vol. 54, No. 11, 1981, pp. 3447-3452.
Janczewski et al., "Effect of Molecular Structure on Optical Properties of Sulfoxide Systems. o-Phenoxyphenylsulfinylacetic Acid and some of Their Derivatives. Part II", *Polish Journal of Chemistry*, vol. 62, No. 1-3, 1964, pp. 91-105, XP008053171.
Kmonicek et al., "(Tert-Amino)-11-(4-Methylpiperazino)Dibenzo[b,f]Thiepins and their 10,11-Dihydro Derivatives; Synthesis and Neuroleptic Activity", *Collection Czechoslov. Chem. Commun.*, vol. 52, 1987, pp. 792-803, XP-002347166.
Lehmler et al., "Synthesis of hydroxylated PCB metabolites with the Suzuki-coupling", *Chemosphere*, vol. 45, 2001, pp. 1119-1127.
Litvak et al., "Synthesis and $S_NAr$ reactions of new dioxins and predioxins", *Chemosphere*, vol. 43, No. 4-7, 2001, pp. 493-495.
Lupus erythematosus [online], [retrieved Dec. 28, 2006]. Retrieved from the Internet, URL; http://en.wikipedia.org/wiki/Lupus_erythematosus>.
Maeda et al., "Studies on the Synthesis and Analgesic and Anti-inflammatory Activities of 2-Thiazolylamino- and 2-Thiazolyloxyarylacetic Acid Derivatives", *Chem. Pharm. Bull.*, vol. 31, No. 10, 1983, pp. 3424-3445, XP-002347167.
Manoury et al., "Synthesis and Analgesic Activities of Some (4-Substituted phenyl-1-piperazinyl)alkyl 2-Aminobenzoates and 2-Aminonicotinates", Journal of Medicinal Chemistry, vol. 22(5), pp. 554-559 (1979).
Meunier et al., "Photochemical behaviour of dichlorprop [(±)-2-(2,4-dichlorophenoxy)propanoic acid] in aqueous solution", *Pest Management Science*, vol. 58, No. 8, 2002, pp. 845-852.
Moser et al., "Synthesis and Quantitative Structure-Activity Relationships of Diclofenac Analogues", *J. Med. Chem.*, vol. 33, 1990, pp. 2358-2368, XP-001024801.
Moshchitskii et al., "Smiles rearrangement of tetrachloropyridyl methyl-hydroxyphenyl sulfone", *Chemistry of Heterocyclic Compounds*, vol. 15, No. 7, 1979, pp. 1085-1088.
Ong et al., "Synthesis and Analgesic Activity of Some Spiro[dibenz[b,f]oxepin-10,4'-piperidine] Derivatives", *J. Med. Chem.*, vol. 22, No. 7, 1979, pp. 834-839, XP-002347163.

Rajsner et al., "Fluorinated tricyclic Neuroleptics: Synthesis and Pharmacology of 8-Fluoro-4-(4-Methylpiperazino)-4,5-Dihydrothieno[2,3-b]-1-Benzothiepin", Collection Czechoslov. Chem. Commun., vol. 44, 1979, pp. 2997-3007, XP-002347164.

Selvi et al., "Vilsmeier cyclization of 2-amino phenoxyacetic acid", Synthetic Communications, vol. 31, No. 14, 2001, pp. 2199-2202.

Sindelar et al., "Synthesis of 3-Chloro-5-(4-Methylpiperazino)-6,7-Dihydro-5H-Dibenzo[b,g]Thiocin, An Eight-Membered Ring Homologue of The Neuroleptic Agent Octoclothepin", Collection Czechoslov. Chem. Commun., vol. 45, 1980, pp. 491-503, XP-002347160.

Sindelar et al., "Fluorinated Tricyclic Neuroleptics with Prolonged Action: 3-Fluoro-8-Trifluoromethyl Derivatives of 10-(4-Methylpiperazino)- and 10-[4-(2-Hydroxyethyl)Piperazino]-10,11-Dihydrodibenzo-[b,f]Thiepin", Collection Czechoslov. Chem. Commun., vol. 46, 1981, pp. 118-140, XP-002347168.

Sindler-Kulyk et al., "Synthesis of New 3-(Phenoxyphenyl)sydnones", J. Hetercyclic Chem., vol. 29, No. 2, 1992, pp. 1013-1015, XP-002347161.

Stokker et al., "3-Hydroxy-3-methylglutaryl-coenzyme A Reductase Inhibitors. 5. 6-(Fluoren-9-yl)- and 6-(Fluoren-9-ylidenyl)-3,5-dihydroxyhexanoic Acids and Their Lactone Derivatives", J. Med. Chem. 29:852-855 (1986).

Thuillier, G., "Derives des acides 24 aryloxyacetiques a activite neurotrope", Chimique Therapeutique, vol. 1, No. 2, 1966, pp. 82-86.

Walsh et al., "Antiinflammatory Activity of N-(2-Benzoylphenyl)alanine Derivatives", J. Med. Chem., vol. 27, 1984, pp. 1317-1321, XP-002347162.

Wheatley et al., "2-Benzylphenol Derivatives. III. Basic Ethers", Journal of American Chemical Society, vol. 71, No. 11, 1949, pp. 3795-3797.

Database CA [Online] Chemical Abstracts Service, Columbus, Ohio, US; XP002372494 retrieved from STN Database accession No. 1956:16264 abstract & OTT, Donald G. et al: "A carbon-14 tracer study of the alkaline rearrangement of chlorophenanthraquinones" Journal of the American Chemical Society, 77, 2325-9 CODEN:JACSAT; ISSN:0002-7863, 1955.

Database CAPLUS [Online] Chemical Abstracts Service, Columbus, Ohio, US; 1992, XP002372495 retrieved from STN Database accession No. 1992:255529 abstract & RAM, Bhagat et al: "Potential hypolipidemic agents part VI: synthesis and biological activity of some new 4-chloro/methyl-2-pyrazolylphenoxy alkanoates" Indian Drugs, vol. 29, No. 6, 1992, pp. 258-262.

Database WPI 1-3, 5, Section Ch, Week 200365 19, 20, Derwent Publications Ltd., London, GB, AN 2003-689635 XP-002301315, WO03068744A1, Ishihara Sangyo Kaisha, Ltd., Aug. 21, 2003.

STN International, File CAPLUS, CAPLUS accession 1-10, No. 1987:597776, document No. 107:197776, Otsuka Pharmaceutical Factory, "Preparation of aminophenol derivatives as anticoagulants, analgesics, hypotensives, and diuretics", JP, A2, 62108859, 19870520.

STN International, File CAPLUS, CAPLUS accession 1-5, 10, No. 1979:186607, document No. 90:186607, Ciba-Geigy, "Phenoxyphenoxyalkanecardoxylic acid derivatives", DE, A1, 2832435, 19790208.

STN International, File CAPLUS, CAPLUS accession 1-5, 10, No. 1971:53748, document No. 74:53748, Walker et al., "Synthesis of 5-phenyl-2,3,4,5-tetrahydro-1,4-benzoxazepines and corresponding 3-ones", & Journal of Organic Chemistry (1970), 36(2), 305-308.

STN International, File CAPLUS, CAPLUS accession 1-3, 5, 10, No. 1992:407796, document No. 117:7796, Tokuyama Soda Co., Ltd., "Preparation of thienyloxphenoxy group-containing carboxylic acids as microbicides", JP, A2, 04021677, 19920124.

STN International, File CAPLUS, CAPLUS accession 1-3, 5, 10, No. 1975:402045, document No. 83:2045, Shiley et al., "Fungicidal activity of some fluoroaromatic compounds", Journal of Fluorine Chemistry (1975), 5(4), 371-376.

STN International, File CAPLUS, CAPLUS accession 1, 3, 5, 10, No. 1972:405106, document No. 77:5106, Oniscu et al., "Monoethanolaminosulfonyl-,diethanolaminosulfonyl- and morpholinosulfonyl-phenoxyacetic derivatives", Buletinul Institutului Politehnic din Iasi, (1971), 14(3-4), 101-114.

STN International, File CAPLUS, CAPLUS accession 1, 3, 5, 10, No. 1961:22702, document No. 55:22702, Takano, K., "Condensation products of furfuryl alcohol. IV. Condensation products of furfuryl alcohol with cresols", Nippon Kagaku Zasshi (1959), 80, 678-681.

STN International, File CAPLUS, CAPLUS accession 1, 3-5, 10, No. 1958:25331, document No. 52:25331, Landa et al., "Properties of sulfide catalysts. V. Preparation of alkylphenols", Chemicke Listy pro Vedu a Prumysl (1957), 51, 1851-1857.

STN Intenational, File CAPLUS, CAPLUS accession 1, 3, 5, 10, No. 1971:498288, document No. 75:98288, Botez et al., "Phenoxybutyric acid sulfamides. I. Sulfamide derivatives of the α-phenoxy-, α-cresoxy-, and α-xylenoxybutyric acids", Buletinul Institutului Politehnic din Iasi (1970), 16(1-2), 161-172.

STN International, File CAPLUS, CAPLUS accession 1-7, 10, No. 1986:109631, document No. 104:109631, Yoshitomi Pharmaceutical Industries, Ltd., "Imidazole derivatives", JP, A2, 60142965, 19850729.

Vippagunta et al., "Crystalline solids", Advanced Drug Delivery Reviews 48:3-26 (2001).

Inflammatory Bowel Disease [online] {retrieved on Apr. 7, 2008 from the internet} {URL:http://www.emedicinehealth.com/script/main/art.asp?articlekey=59121&pf=3&page=8}.

Rheumatoid arthritis [online] {retrieved on Apr. 7, 2008 from the internet} {URL:http://www.nlm.nih.gov/medlineplus/ency/artiele/000431.htm}.

Asthma [online] [retrieved on May 30, 2008] retrieved from the Internet URL:http://www.nlm.nih.gov/medlineplus/ency/article/000141.htm.

Chiu et al., "Derivation and Properties of Recombinant Fab Antibodies to Coplanar Polychlorinated Biphenyls", J. Agric. Food Chem. 48:2614-2624 (2000).

Dalal et al., "Synthetic insecticides. I. Synthesis of α, α-bis(aryl)-β, β, γ-trichlorobutanes", STN Accession No. 1950:35789, Document No. 44:35789, Abstract of Journal of the Indian Chemical Society 26:549-52 (1949).

Fromageot et al., "Photodecarboxylation of 2-(2'-carboxymethoxy-5'-methylphenyl)-benzotriazole", Journal of Photochemistry and Photobiology, A: Chemistry 44(1):93-98 (1988).

Gavezzotti, "Are Crystal Structures Predictable?", Acc. Chem. Res. 27:309-314 (1994).

Golub et al., "Molecular Classification of Cancer: Class Discovery and Class Prediction by Gene Expression Monitoring", Science 286:531-537 (1999).

Hazlet et al., "Bromination of 2-phenylphenyl acetate", STN Accession No. 1941:37645, Document No. 35:37645, Abstract of Journal of the American Chemical Society 63:1890-2 (1941).

Ly et al., "Small-molecule CRTH2 antagonists for the treatment of allergic inflammation: an overview", Expert Opin. Invest. Drugs 14(7):769-773 (2005).

Manske et al., "Synthesis and Reactions of Some Dibenzoxepins", Journal of American Chemical Society 72:4797-4799 (1950).

Morissette et al., "High-throughput crystallization: polymorphs, salts, co-crystals and solvates of pharmaceutical solids", Advanced Drug Delivery Reviews 56:275-300 (2004).

Ram et al., "Potential Hypolipidemic Agents Part VI: Synthesis and Biological Activity of Some New 4-Chloro/Methyl-2-pyrazolylphenoxy Alkanoates", Indian Drugs 29(6), 258-262 (1992).

Ueda et al., "The Synthesis of 10-(4-Methylpiperazino)dibenzo[b,f]thiepin and Related Compounds. Neurotropic and Psychotropic Agents", Chem. Pharm. Bull. 23(10):2223-2231 (1975).

Ulven et al., "Targeting of the Prostaglandin D₂ Receptors DP and CRTH2 for Treatment of Inflammation", Current Topics in Medicinal Chemistry 6:1427-1444 (2006).

Rhinitis [online] [retrieved on Nov. 12, 2008 from the internet] URL:http://www.healthline.com/galecontent/rhinitis?print=true.

RN 110624-55-0, retrieved from CAPLUS; retrieved on Apr. 7, 2008.

USPTO Office Action in U.S. Appl. No. 10/552,082, mailed Oct. 29, 2007, 6 pages.

Fish & Richardson P.C., Amendment in Reply to Action of Oct. 29, 2007 in U.S. Appl. No. 10/552,082, filed Feb. 29, 2008, 18 pages.

USPTO Final Office Action in U.S. Appl. No. 10/552,082, mailed Jun. 9, 2008, 18 pages.
Fish & Richardson P.C., Amendment in Reply to Action of Jun. 9, 2008 in U.S. Appl. No. 10/552,082, filed Sep. 9, 2008, 11 pages.
USPTO Office Action in U.S. Appl. No. 10/552,082, mailed Dec. 4, 2008, 23 pages.
Fish & Richardson P.C., Amendment in Reply to Action of Dec. 4, 2008 in U.S. Appl. No. 10/552,082, filed Apr. 6, 2009, 8 pages.
USPTO Notice of Allowance in U.S. Appl. No. 10/552,082, mailed Jul. 1, 2009, 9 pages.
Fish & Richardson P.C., RCE and Interview Summary in response to Notice of Allowance of Jul. 1, 2009 in U.S. Appl. No. 10/552,082, filed Sep. 30, 2009, 2 pages.
USPTO Office Action in U.S. Appl. No. 10/552,082, mailed Jan. 7, 2010, 12 pages.
Fish & Richardson P.C., Amendment in Reply to Action of Jan. 7, 2010 in U.S. Appl. No. 10/552,082, filed Jul. 2, 2010, 8 pages.
USPTO Office Action in U.S. Appl. No. 10/551,783, mailed Dec. 7, 2009, 15 pages.
Fish & Richardson P.C., Amendment in Reply to Action of Dec. 7, 2009 in U.S. Appl. No. 10/551,783, filed Mar. 8, 2010, 17 pages.
USPTO Office Action in U.S. Appl. No. 10/551,783, mailed Apr. 23, 2010, 9 pages.
Fish & Richardson P.C., Amendment in Reply to Action of Apr. 23, 2010 in U.S. Appl. No. 10/551,783, filed Jul. 2, 2010, 23 pages.
USPTO Office Action in U.S. Appl. No. 10/569,065, mailed May 4, 2007, 12 pages.
Fish & Richardson P.C., Amendment in Reply to Action of May 4, 2007 in U.S. Appl. No. 10/569,065, filed Aug. 3, 2007, 14 pages.
USPTO Final Office Action in U.S. Appl. No. 10/569,065, mailed Oct. 17, 2007, 4 pages.
Fish & Richardson P.C., Amendment in Reply to Action of Oct. 17, 2007 in U.S. Appl. No. 10/569,065, filed Jan. 17, 2008, 9 pages.
USPTO Office Action in U.S. Appl. No. 10/569,065, mailed Apr. 16, 2008, 14 pages.
Fish & Richardson P.C., Amendment in Reply to Action of Apr. 16, 2008 in U.S. Appl. No. 10/569,065, filed Jul. 16, 2008, 38 pages.
USPTO Office Action in U.S. Appl. No. 10/569,065, mailed Oct. 28, 2008, 15 pages.
Fish & Richardson P.C., Amendment in Reply to Action of Oct. 28, 2008 in U.S. Appl. No. 10/569,065, filed Jan. 27, 2009, 7 pages.
USPTO Office Action in U.S. Appl. No. 10/569,065, mailed May 13, 2009, 10 pages.
Fish & Richardson P.C., Amendment in Reply to Action of May 13, 2009 in U.S. Appl. No. 10/569,065, filed Jul. 14, 2009, 9 pages.
USPTO Notice of Allowance in U.S. Appl. No. 10/569,065, mailed Oct. 23, 2009, 10 pages.
Fish & Richardson P.C., RCE and IDS in Reply to Notice of Allowance of Oct. 23, 2009 in U.S. Appl. No. 10/569,065, filed Nov. 5, 2009, 3 pages.
USPTO Notice of Allowance in U.S. Appl. No. 10/569,065, mailed Jan. 28, 2010, 9 pages.
Fish & Richardson P.C., RCE and IDS in Reply to Notice of Allowance of Jan. 28, 2010 in U.S. Appl. No. 10/569,065, filed Mar. 31, 2010, 5 pages.
USPTO Notice of Allowance in U.S. Appl. No. 10/569,065, mailed May 13, 2010, 10 pages.
Fish & Richardson P.C., RCE and IDS in Reply to Notice of Allowance of May 13, 2010 in U.S. Appl. No. 10/569,065, filed Aug. 2, 2010, 4 pages.
USPTO Office Action in U.S. Appl. No. 11/571,707, mailed Mar. 12, 2010, 16 pages.
USPTO Office Action in U.S. Appl. No. 11/574,076, mailed Oct. 27, 2008, 23 pages.
Fish & Richardson P.C., Amendment in Reply to Action of Oct. 27, 2008 in U.S. Appl. No. 11/574,076, filed Apr. 27, 2009, 21 pages.
USPTO Final Office Action in U.S. Appl. No. 11/574,076, mailed Aug. 18, 2009, 7 pages.
Fish & Richardson P.C., RCE and Amendment in Reply to Action of Aug. 18, 2009 in U.S. Appl. No. 11/574,076, filed Dec. 18, 2009, 13 pages.
USPTO Notice of Allowance in U.S. Appl. No. 11/574,076, mailed Feb. 3, 2010, 12 pages.
Fish & Richardson P.C., Response to Notice of Allowance of Feb. 3, 2010 in U.S. Appl. No. 11/574,076, filed Apr. 30, 2010, 2 pages.
USPTO Office Action in U.S. Appl. No. 11/576,372, mailed Jul. 22, 2009, 19 pages.
Fish & Richardson P.C., Amendment in Reply to Action of Jul. 22, 2009 in U.S. Appl. No. 11/576,372, filed Jan. 22, 2010, 18 pages.
USPTO Final Office Action in U.S. Appl. No. 11/576,372, mailed May 7, 2010, 7 pages.
USPTO Office Action in U.S. Appl. No. 12/089,276, mailed Jun. 17, 2009, 28 pages.
Fish & Richardson P.C., Amendment in Reply to Action of Jun. 17, 2009 in U.S. Appl. No. 12/089,276, filed Sep. 22, 2009, 10 pages.
USPTO Notice of Allowance in U.S. Appl. No. 12/089,276, mailed Jan. 4, 2010, 6 pages.
Fish & Richardson P.C., RCE and IDS in Reply to Notice of Allowance of Jan. 4, 2010 in U.S. Appl. No. 12/089,276, filed Mar. 31, 2010, 7 pages.
USPTO Notice of Allowance in U.S. Appl. No. 12/089,276, mailed Apr. 21, 2010, 11 pages.
Fish & Richardson P.C., RCE and IDS in Reply to Notice of Allowance of Apr. 21, 2010 in U.S. Appl. No. 12/089,276, filed Jul. 21, 2010, 5 pages.
USPTO Office Action in U.S. Appl. No. 12/092,431, mailed Aug. 4, 2009, 8 pages.
Fish & Richardson P.C., Amendment in Reply to Action of Aug. 4, 2009 in U.S. Appl. No. 12/092,431, filed Feb. 3, 2010, 15 pages.
USPTO Final Office Action in U.S. Appl. No. 12/092,431, mailed May 4, 2010, 13 pages.
USPTO Office Action in U.S. Appl. No. 12/167,513, mailed Nov. 2, 2009, 19 pages.
Fish & Richardson P.C., Amendment in Reply to Action of Nov. 2, 2009 in U.S. Appl. No. 12/167,513, filed Feb. 2, 2010, 19 pages.
USPTO Final Office Action in U.S. Appl. No. 12/167,513, mailed Apr. 22, 2010, 22 pages.
Berhenke et al., "Some Aryloxyaliphatic Acids", *Journal of the American Chemical Society* 73:4458 (1951).
Burger, "Isosterism and bioisosterism in drug design", in Progress in Drug Research 287-328 (Ernst Jucker, ed., Birkhauser Verlag, 1991).
Chemical abstract 123:213132 in CAS (or JP07140725), 1995.
Chemical abstract 123:22081 in CAS (or EP622690), 1995.
Chemical abstract 116:123167 in CAS (or EP455058), 1992.
Chemical abstract 85:56485 in CAS or Parli et al., "The relation between the metabolism of 2,4-dichloro-6-phenylphenoxyethylamine (DPEA) and related compounds and their activities as microsomal mono-oxygenase inhibitors", Drug Metabolism and Disposition 1(4):628-33 (1973).
Chemical abstract 69:93942 in CAS or Cheng et al., "Phenylphenol derivatives with biological activity. III. Fungistatic activity of phenylphenol derivatives", Agricultural and Biological Chemistry 32(9):1162-74 (1968).
Chemical abstract 49:86470 in CAS or Mel'nikov et al., "Structure and physiological activity of alkyl- and aryl-phenoxyacetic acids and their derivatives", Fiziologiya Rastenii 2:267-70 (1995).
Chemical abstract 35:37645 in CAS or Hazlet et al., "The Bromination of 2-Phenylphenyl Acetate", Journal of the American Chemical Society 63:1890-2 (1941).
Coxworth, "Synthesis of Chlorinated 2-(3-Benzofuranyl)Phenols", *Canadian Journal of Chemistry* 44:1092-1096 (1966).
Patani et al., "Bioisosterism: A Rational Approach in Drug Design", *Chem. Rev.* 96:3147-3176 (1996).
Database Beilstein chemical extract accession No. 6722243, Jan. 2010.
Database Beilstein chemical extract accession No. 6722682, Jan. 2010.
Database Beilstein chemical extract accession No. 3532059, Jan. 2010.
Database Beilstein chemical extract accession No. 2533336, Jan. 2010.
Database Beilstein chemical extract accession No. 2537173, Jan. 2010.
Database Beilstein chemical extract accession No. 3385275, Jan. 2010.

Database Beilstein chemical extract accession No. 3386554, Jan. 2010.

USPTO Notice of Allowance in U.S. Appl. No. 10/552,082, mailed Sep. 15, 2010, 12 pages.

USPTO Notice of Allowance in U.S. Appl. No. 10/551,783, mailed Sep. 7, 2010, 6 pages.

Fish & Richardson P.C., RCE and IDS in reply to Notice of Allowance of Sep. 7, 2010 in U.S. Appl. No. 10/551,783, filed Dec. 6, 2010, 4 pages.

USPTO Notice of Allowance in U.S. Appl. No. 10/569,065, mailed Sep. 1, 2010, 9 pages.

Fish & Richardson P.C., RCE and IDS in Reply to Notice of Allowance of Sep. 1, 2010 in U.S. Appl. No. 10/569,065, filed Nov. 8, 2010, 5 pages.

USPTO Notice of Allowance in U.S. Appl. No. 10/569,065, mailed Dec. 2, 2010, 10 pages.

Fish & Richardson P.C., RCE and IDS in Reply to Notice of Allowance of Dec. 2, 2010 in U.S. Appl. No. 10/569,065, filed Feb. 15, 2011, 5 pages.

Fish & Richardson P.C., Amendment in Reply to Action of Mar. 12, 2010 in U.S. Appl. No. 11/571,707, filed Sep. 3, 2010, 14 pages.

USPTO Notice of Allowance in U.S. Appl. No. 11/571,707, mailed Nov. 22, 2010, 12 pages.

Fish & Richardson P.C., Response to Notice of Allowance of Nov. 22, 2010 in U.S. Appl. No. 11/571,707, filed Feb. 18, 2011, 12 pages.

Fish & Richardson P.C., Reply to Action of May 7, 2010 in U.S. Appl. No. 11/576,372, filed Aug. 9, 2010, 10 pages.

USPTO Office Action in U.S. Appl. No. 11/576,372, mailed Sep. 2, 2010, 7 pages.

Fish & Richardson P.C., RCE, IDS and Amendment in Reply to Action of Sep. 2, 2010 in U.S. Appl. No. 11/576,372, filed Dec. 2, 2010, 16 pages.

USPTO Office Action in U.S. Appl. No. 12/089,275, mailed Jan. 26, 2011, 25 pages.

USPTO Notice of Allowance in U.S. Appl. No. 12/089,276, mailed Sep. 21, 2010, 9 pages.

Fish & Richardson P.C., RCE and IDS in Reply to Notice of Allowance of Sep. 21, 2010 in U.S. Appl. No. 12/089,276, filed Dec. 20, 2010, 6 pages.

USPTO Notice of Allowance in U.S. Appl. No. 12/089,276, mailed Jan. 4, 2011, 11 pages.

Fish & Richardson P.C., RCE and IDS in Reply to Notice of Allowance of Jan. 4, 2011 in U.S. Appl. No. 12/089,276, filed Apr. 4, 2011, 4 pages.

Fish & Richardson P.C., RCE, IDS and Amendment in Reply to Action of May 4, 2010 in U.S. Appl. No. 12/092,431, filed Sep. 7, 2010, 16 pages.

Fish & Richardson P.C., Amendment in Reply to Action of Apr. 22, 2010 in U.S. Appl. No. 12/167,513, filed Oct. 22, 2010, 22 pages.

* cited by examiner

PHENOXYACETIC ACID DERIVATIVES USEFUL FOR TREATING RESPIRATORY DISEASES

CROSS-REFERENCE TO RELATED APPLICATIONS

This application is a national phase application under 35 U.S.C. §371 of PCT International Application No. PCT/GB2005/004464, filed Nov. 22, 2005, which claims priority to United Kingdom Application Serial No. 0425673,1, filed Nov. 23, 2004 and United Kingdom Application Serial No. 0508923.0, filed Apr. 30, 2005.

The present invention relates to substituted phenoxyacetic acids as useful pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTH2. GB 1356834 discloses a series of compounds said to possess anti-inflammatory, analgesic and antipyretic activity. It has been found that certain phenoxyacetic acids are active at the CRTH2 receptor, and as a consequence are expected to be potentially useful for the treatment of various respiratory diseases, including asthma and COPD.

In a first aspect the invention therefore provides a compound of formula (I) or a pharmaceutically acceptable salt thereof:

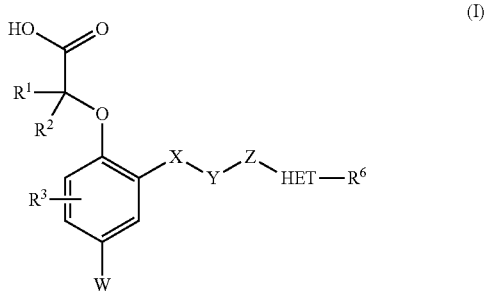

(I)

in which:

$R^1$ and $R^2$ independently represent a hydrogen atom, halogen, $C_2$-$C_6$ alkenyl, $C_2$-$C_6$ alkynyl, $C_3$-$C_7$ cycloalkyl or a $C_{1-6}$ alkyl group, the latter four groups being optionally substituted by one or more substituents independently selected from halogen, $C_3$-$C_7$ cycloalkyl, $NR^9R^{10}$, $OR^8$, $S(O)_nR^7$ (where n is 0, 1 or 2);

or $R^1$ and $R^2$ together can form a 3-8 membered ring optionally containing one or more atoms selected from O, S, $NR^{11}$ and itself optionally substituted by one or more $C_1$-$C_3$ alkyl or halogen;

W is halogen, cyano, nitro, $SO_2R^7$, $SO_2NR^9R^{10}$, $OR^8$, or $C_{1-6}$alkyl, the latter being optionally substituted by one or more substituents independently selected from halogen, $OR^8$ and $NR^7R^8$, $S(O)_nR^5$ where n is 1 or 2.

$R^3$ is one or more substituents independently selected from hydrogen, halogen, CN, nitro, $SO_2R^7$, $OR^8$, $SR^7$, $SOR^7$, $SO_2NR^9R^{10}$, $CONR^9R^{10}$, $NR^9R^{10}$, $NR^{11}SO_2R^7$, $NR^{11}O_2R^7$, $NR^{11}COR^7$ or $C_{1-6}$ alkyl, the latter being optionally substituted by one or more substituents independently selected from halogen, $OR^8$ and $NR^9R^{10}$, $S(O)_nR^7$ where n is 0, 1 or 2;

X represents a bond, or $C_1$-$C_6$ alkyl, optionally substituted by one or more substituents independently selected from halogen, $C_1$-$C_6$ alkyl the latter being optionally substituted by one or more substituents independently selected from halogen, $OR^6$ and $NR^7R^8$, $S(O)_nR^5$ where n is 0, 1 or 2;

Y represents a diamine of the following type:—

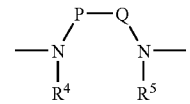

$R^4$ and $R^5$ independently represent hydrogen, $SO_2R^7$, $C(O)R^7$, $CO_2R^7$ and $C_1$-$C_6$ alkyl, the latter being optionally substituted by one or more substituents independently selected from aryl, heteroaryl, halogen, $OR^8$ and $NR^9R^{10}$, $S(O)_nR^7$ where n is 0, 1 or 2;

$R^4$ and $R^5$ are joined together or one of $R^4$ and $R^5$ is joined onto P or Q to form a saturated heterocyclic 3-10 membered ring with, 1 or 2 endocyclic nitrogen atoms;

P and Q independently represent, $C_1$-$C_6$ alkyl optionally substituted by one or more substituents independently selected from (=O), halogen, $OR^8$ and $NR^9R^{10}$, $S(O)_nR^7$ (where n is 0, 1 or 2), $C_1$-$C_6$ alkyl, $C_3$-$C_6$ cycloalkyl, aryl or heteroaryl (the latter two being optionally substituted by one or more substituents independently selected from halogen, $OR^8$ and $NR^9R^{10}$, $CONR^9R^{10}$, $S(O)_nR^7$ where n is 0, 1 or 2);

Z represents a bond, $(CR^{12})n$—$C(O)$, $(CR^{12})n$—$S(O)n$, $C(O)(CR^{12})n$, or $S(O)_2(CR^{12})n$, $S(O)_2N(CR^{12})n$, where n=0, 1 or 2;

HET represents aryl or heteroaryl;

$R^6$ represents one or more substituents independently selected from hydrogen, halogen, CN, nitro, $COR^7$, $CO_2R^8$, $SO_2R^7$, $OR^8$, $SR^8$, $SOR^7$, $SO_2NR^9R^{10}$, $CONR^9R^{10}$, $NR^9R^{10}$, $NR^8SO_2R^7$, $NR^8CO_2R^8$, $NR^8COR^7$, $NR^8CONR^9R^{10}$, $NR^8SO_2NR^9R^{10}$, aryl, heteroaryl, $C_2$-$C_6$ alkenyl, $C_2$-$C_6$ alkynyl, $C_3$-$C_7$ cycloalkyl or $C_{1-6}$alkyl, the latter four groups being optionally substituted by one or more substituents independently selected from halogen, $C_3$-$C_7$ cycloalkyl, CN, $OR^8$, $NR^9R^{10}$, $S(O)_nR^7$ (where n is 0, 1 or 2), $CONR^9R^{10}$, $NR^8COR^7$, $SO_2NR^9R^{10}$ and $NR^8SO_2R^7$;

$R^7$ represents a $C_1$-$C_6$ alkyl, an aryl or a heteroaryl group all of which may be optionally substituted by halogen atoms, $OR^8$, $NR^{14}R^{15}$;

$R^8$ represents hydrogen, $C_1$-$C_6$, alkyl, an aryl or a heteroaryl group all of which may be optionally substituted by halogen atoms, $OR^8$, $NR^{14}R^{15}$;

$R^9$ and $R^{10}$ independently represent hydrogen, $C_3$-$C_7$ cycloalkyl or $C_{1-6}$alkyl, the latter two groups being optionally substituted by one or more substituents independently selected from halogen, $C_3$-$C_7$ cycloalkyl, $OR^6$ and $NR^{14}R^{15}$, $S(O)_nR^6$ (where n=0, 1 or 2), $CONR^7R^8$, $NR^6COR^7$, $SO_2NR^7R^8$ and $NR^6SO_2R^5$;

or $R^9$ and $R^{10}$ together with the nitrogen atom to which they are attached can form a 3-8 membered saturated heterocylic ring optionally containing one or more atoms selected from O, $S(O)_n$ (where n=0, 1 or 2), $NR^{13}$, and itself optionally substituted by halogen or $C_{1-3}$ alkyl;

$R^{11}$ represents a hydrogen atom, $C(O)R^9$, $C_1$-$C_6$ alkyl an aryl or a heteroaryl group (the latter three can be optionally substituted by halogen);

$R^{12}$ represents one or more from hydrogen, or a $C_{1-6}$alkyl group, the latter being optionally substituted by one or more substituents independently selected from halogen, $C_3$-$C_7$cycloalkyl, $NR^{14}R^{15}$, $OR^8$, $S(O)_nR^7$ (where n is 0, 1 or 2);

$R^{13}$ represent hydrogen, $C_{1-4}$ alkyl, —$COC_1$-$C_4$ alkyl, $COYC_1$-$C_4$alkyl where Y is O or $NR^7$; and $R^{14}$ and $R^{15}$ independently represent hydrogen, $C_{1-4}$ alkyl or $R^{14}$ and $R^{15}$ together with the nitrogen atom to which they are attached can form a 3-8 membered saturated heterocylic ring optionally containing one or more atoms selected from O, $S(O)_n$ (where n=0, 1 or 2), $NR^{13}$, and itself optionally substituted by halogen or $C_{1-3}$ alkyl.

Examples of monocyclic saturated rings as defined for Y include piperizine, alkyl substituted piperizine (such as methyl, ethyl or propyl piperizine), piperazinone, imidazolidine, homopiperazine, aminopyrrolidine, aminoazetidine and aminopiperidine.

Examples of aryl include phenyl and naphthyl.

Heteroaryl is defined as a 5-7 member aromatic ring or can be 6,6- or 6,5-fused bicyclic ring optionally containing one or more heteroatoms selected from N, S and O. The bicyclic ring may be linked through carbon or nitrogen and may be attached through the 5 or 6 membered ring and can be fully or partially saturated. Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine, quinolone and 1,2-methylenedioxy benzene.

In the context of the present specification, unless otherwise indicated the groups aryl and heteroaryl can be optionally substituted by $R^6$.

In the context of the present specification, unless otherwise indicated, an alkyl or alkenyl group or an alkyl or alkenyl moiety in a substituent group may be linear or branched.

Heterocyclic rings as defined for $R^{14}$ and $R^{15}$ means saturated heterocycles, examples include morpholine, thiomorpholine, azetidine, imidazolidine, pyrrolidine, piperidine and piperazine.

Preferably W is halogen, $CF_3$, CN or $C_1$-$C_6$alkyl; more preferably W is halogen, methyl, CN or $CF_3$;

Preferably $R^1$ and $R^2$ are independently hydrogen or methyl.

Preferably $R^3$ is hydrogen or halogen, more preferably $R^3$ is hydrogen;

Preferably X is a bond or $CH_2$, more preferably X is $CH_2$;

Preferably the group Y (together with the two nitrogen atoms to which it is attached) is piperizine, piperazinone, homopiperazine or amino pyrrolidine; more preferably the group Y is piperizine or homopiperazine which can be optionally substituted by $C_{1-4}$ alkyl. Most preferably the group Y is piperazine, which is optionally substituted by $C_{1-4}$ alkyl.

Preferably the group Z is $SO_2$, $SO_2CH_2$, $C(O)CH_2C(O)C(Me)_2$, C(O) or $C(O)CH_2CH_2$, more preferably the group Z is $SO_2$, $SO_2CH_2$ or $C(O)CH_2$.

Preferably HET is aryl, or heteroaryl, more preferably HET is phenyl or heteroaryl, most preferably HET is phenyl.

Preferably $R^6$ is one or more substituents selected from halogen, hydrogen, $C_1$-$C_6$ alkyl (optionally substituted by one or more halogen atoms), alkoxy (alkyl group is optionally substituted by halogen atoms), nitro, cyano or $SO_2$alkyl; more preferably $R^6$ is hydrogen, halogen, CM alkyl, O-alkyl, $OCF_2$, $OCF_3$, CN or $SO_2Me$;

Preferred compounds of the invention include:
[2-[4-[(4-Fluorophenyl)sulfonyl]-1-piperazinyl]-4-(trifluoromethyl)phenoxy]-acetic acid;
[2-[[4-(phenylsulfonyl)-1-piperazinyl]methyl]-4-(trifluoromethyl)phenoxy]-acetic acid;
[2-[4-[[(4-cyanophenyl)sulfonyl]-1-piperazinylmethyl]]-4-(trifluoromethyl)phenoxy]-acetic acid;
[2-[[4-[(2-fluorophenyl)sulfonyl]-1-piperazinyl]methyl]-4-(trifluoromethyl)phenoxy]-acetic acid;
[2-[[4-[(2-methylphenyl)sulfonyl]-1-piperazinyl]methyl]-4-(trifluoromethyl)phenoxy]-acetic acid;
[2-[[4-[(4-nitrophenyl)sulfonyl]-1-piperazinyl]methyl]-4-(trifluoromethyl)phenoxy]-acetic acid;
[2-[[4-[(4-fluorophenyl)sulfonyl]hexahydro-1H-1,4-diazepin-1-yl]methyl]-4-(trifluoromethyl)phenoxy]-acetic acid;
[2-[hexahydro-4-[[(4-methoxyphenyl)sulfonyl]-1H-1,4-diazepin-1-yl]methyl]-4-(trifluoromethyl)phenoxy]-acetic acid;
[2-[[hexahydro-4-(phenylsulfonyl)-1H-1,4-diazepin-1-yl]methyl]-4-(trifluoromethyl)phenoxy]-acetic acid;
[2-[[4-[(4-cyanophenyl)sulfonyl]hexahydro-1H-1,4-diazepin-1-yl]methyl]-4-(trifluoromethyl)phenoxy]-acetic acid;
[4-chloro-2-[4-(phenylsulfonyl)-1-piperazinyl]phenoxy]-acetic acid;
[4-chloro-2-[[4-[(4-fluorophenyl)sulfonyl]-1-piperazinyl]methyl]phenoxy]-acetic acid;
[4-chloro-2-[[4-[(4-chlorophenyl)sulfonyl]-1-piperazinyl]methyl]phenoxy]-acetic acid;
[4-chloro-2-[[4-[[4-(trifluoromethyl)phenyl]methyl]sulfonyl]-1-piperazinyl]phenoxy]-acetic acid;
[4-chloro-2-[[4-[[4-(trifluoromethoxy)phenyl]methyl]sulfonyl]-1-piperazinyl]phenoxy]-acetic acid;
[4-chloro-2-[4-[[[4-(methylsulfonyl)phenyl]sulfonyl]-1-piperazinyl]methyl]phenoxy]-acetic acid;
[4-chloro-2-[[4-[(3-fluorophenyl)sulfonyl]-1-piperazinyl]methyl]phenoxy]-acetic acid;
[4-chloro-2-[[4-[[3-(trifluoromethyl)phenyl]sulfonyl]-1-piperazinyl]methyl]phenoxy]-acetic acid;
[4-chloro-2-[[4-[(3-chlorophenyl)sulfonyl]-1-piperazinyl]methyl]phenoxy]-acetic acid;
[4-chloro-2-[[4-[[3-(trifluoromethoxy)phenyl]sulfonyl]-1-piperazinyl]methyl]phenoxy]-acetic acid;
[4-chloro-2-[[4-[[3-(difluoromethoxy)phenyl]sulfonyl]-1-piperazinyl]methyl]phenoxy]-acetic acid;
[4-chloro-2-[[4-[(3-chloro-4-fluorophenyl)sulfonyl]-1-piperazinyl]methyl]phenoxy]-acetic acid;
[4-chloro-2-[[4-[(3,4-dichlorophenyl)sulfonyl]-1-piperazinyl]methyl]phenoxy]-acetic acid;
[4-chloro-2-[[4-[(3,4-difluorophenyl)sulfonyl]-1-piperazinyl]methyl]phenoxy]-acetic acid;
[4-chloro-2-[[4-[(phenylmethyl)sulfonyl]-1-piperazinyl]methyl]phenoxy]-acetic acid;
[4-chloro-2-[[4-[[(2-nitrophenyl)methyl]sulfonyl]-1-piperazinyl]methyl]phenoxy]-acetic acid;
[4-chloro-2-[[4-[[(3-chlorophenyl)methyl]sulfonyl]-1-piperazinyl]methyl]phenoxy]-acetic acid;
[4-chloro-2-[[4-[[(4-chlorophenyl)methyl]sulfonyl]-1-piperazinyl]methyl]phenoxy]-acetic acid;
[2-[[4-(phenylacetyl)-1-piperazinyl]methyl]-4-(trifluoromethyl)phenoxy]-acetic acid;
[4-Chloro-2-[[4-[(4-chlorophenyl)acetyl]-1-piperazinyl]methyl]phenoxy]-acetic acid;
[4-Chloro-2-[[4-(1-oxo-3-phenylpropyl)-1-piperazinyl]methyl]phenoxy]-acetic acid;

[3-Chloro-2-[[4-[(4-chlorophenyl)acetyl]-1-piperazinyl]methyl]phenoxy]-acetic acid;
[2-Chloro-2-[[4-[(4-chlorophenyl)acetyl]-1-piperazinyl]methyl]phenoxy]-acetic acid;
[4-chloro-2-[1-[4-(phenylsulfonyl)-1-piperazinyl]methyl]phenoxy]-acetic acid trifluoroacetate salt;
[2-[1-(4-benzoyl-1-piperazinyl)ethyl]-4-chlorophenoxy]-acetic acid, trifluoroacetate salt;
[4-chloro-2-[[[1-[(phenylmethyl)sulfonyl]-3-pyrrolidinyl]amino]methyl]phenoxy]-acetic acid;
[4-chloro-2-[[[1-(phenylsulfonyl)-3-pyrrolidinyl]amino]methyl]phenoxy]-acetic acid;
[4-chloro-2-[4-(phenylsulfonyl)-1-piperazinyl]phenoxy]-acetic acid;
[4-chloro-2-[4-[(phenylmethyl)sulfonyl]-1-piperazinyl]phenoxy]-acetic acid;
[4-chloro-2-[4-(phenylacetyl)-1-piperazinyl]phenoxy]-acetic acid;
[2-[(4-benzoyl-1-piperazinyl)methyl]-4-(trifluoromethyl)phenoxy]-acetic acid;
[2-[[4-(2-thienylacetyl)-1-piperazinyl]methyl]-4-(trifluoromethyl)phenoxy]-acetic acid;
[4-Chloro-2-[[4-[[(4-fluorophenyl)methyl]sulfonyl]-1-piperazinyl]methyl]phenoxy]acetic acid;
[4-Chloro-2-[[4-[[(4-methylphenyl)methyl]sulfonyl]-1-piperazinyl]methyl]phenoxy]acetic acid;
[4-Chloro-2-[[4-[[(3-methylphenyl)methyl]sulfonyl]-1-piperazinyl]methyl]phenoxy]acetic acid;
[4-Chloro-2-[[4-[(2-pyridinylmethyl)sulfonyl]-1-piperazinyl]methyl]phenoxy]acetic acid;
[4-Chloro-2-[[4-[(3-pyridinylmethyl)sulfonyl]-1-piperazinyl]methyl]phenoxy]acetic acid;
[4-Chloro-2-[[4-[(4-methylphenyl)acetyl]-1-piperazinyl]methyl]phenoxy]acetic acid;
[4-Chloro-2-[[4-[(4-fluorophenyl)acetyl]-1-piperazinyl]methyl]phenoxy]acetic acid;
[4-Chloro-2-[[4-[(4-methoxyphenyl)acetyl]-1-piperazinyl]methyl]phenoxy]acetic acid;
[4-Chloro-2-[[4-(3-pyridinylacetyl)-1-piperazinyl]methyl]phenoxy]acetic acid;
[4-Chloro-2-[[4-[(4-cyanophenyl)acetyl]-1-piperazinyl]methyl]phenoxy]acetic acid;
[4-Chloro-2-[[2-methyl-4-(phenylsulfonyl)-1-piperazinyl]methyl]phenoxy]acetic acid;
[4-Chloro-2-[[2-methyl-4-[(phenylmethyl)sulfonyl]-1-piperazinyl]methyl]phenoxy]acetic acid;
[4-Chloro-2-[[(2R)-2-methyl-4-(phenylsulfonyl)-1-piperazinyl]methyl]phenoxy]acetic acid;
[4-Chloro-2-[[3-methyl-4-[(phenylmethyl)sulfonyl]-1-piperazinyl]methyl]phenoxy]acetic acid;
[4-Chloro-2-[[3-methyl-4-(phenylsulfonyl)-1-piperazinyl]methyl]phenoxy]acetic acid;
[4-Chloro-2-[[3-methyl-4-(phenylacetyl)-1-piperazinyl]methyl]phenoxy]acetic acid;
[4-Chloro-2-[[(3S)-3-methyl-4-(phenylsulfonyl)-1-piperazinyl]methyl]phenoxy]acetic acid;
[4-Chloro-2-[[(3R)-3-methyl-4-(phenylsulfonyl)-1-piperazinyl]methyl]phenoxy]acetic acid;
[4-Chloro-2-[[(3R)-3-methyl-4-[(phenylmethyl)sulfonyl]-1-piperazinyl]methyl]phenoxy]acetic acid;
[4-Chloro-2-[[(3S)-3-methyl-4-[(phenylmethyl)sulfonyl]-1-piperazinyl]methyl]phenoxy]acetic acid;
[4-Chloro-2-[[(3S)-3-methyl-4-(phenylacetyl)-1-piperazinyl]methyl]phenoxy]acetic acid;
[4-Chloro-2-[[(3S)-3-methyl-4-(phenylacetyl)-1-piperazinyl]methyl]phenoxy]acetic acid;

c) [4-Chloro-2-[[(3S)-3-methyl-4-(phenylacetyl)-1-piperazinyl]methyl]phenoxy]acetic acid;
[4-Chloro-2-[[(3S)-4-[(4-chlorophenyl)acetyl]-3-methyl-1-piperazinyl]methyl]phenoxy]acetic acid;
[2-[(4-Benzoyl-3-methyl-1-piperazinyl)methyl]-4-chlorophenoxy]acetic acid;
[4-chloro-2-[[2,5-dimethyl-4-(phenylacetyl)-1-piperazinyl]methyl]phenoxy]-acetic acid;
[4-Chloro-2-[[4-(1-oxo-2-phenylpropyl)-1-piperazinyl]methyl]phenoxy]-acetic acid;
[4-Chloro-2-[[(3S)-3-ethyl-4-(phenylsulfonyl)-1-piperazinyl]methyl]phenoxy]-acetic acid;
[4-chloro-2-[[(3S)-3-ethyl-4-(phenylacetyl)-1-piperazinyl]methyl]phenoxy]-acetic acid;
(Cis)-[4-chloro-2-[[2,3-dimethyl-4-(phenylacetyl)-1-piperazinyl]methyl]phenoxy]-acetic acid;
[4-chloro-2-[[(3S)-4-(phenylsulfonyl)-3-propyl-1-piperazinyl]methyl]phenoxy]-acetic acid;
[4-Chloro-2-[[(3S)-4-(phenylacetyl)-3-propyl-1-piperazinyl]methyl]phenoxy]-acetic acid;
[4-chloro-2-[[(3R,5S)-3,5-dimethyl-4-(phenylacetyl)-1-piperazinyl]methyl]phenoxy]-acetic acid;
[4-chloro-2-[[hexahydro-4-(phenylsulfonyl)-1H-1,4-diazepin-1-yl]methyl]phenoxy]-acetic acid;
[4-chloro-2-[[hexahydro-4-[(phenylmethyl)sulfonyl]-1H-1,4-diazepin-1-yl]methyl]phenoxy]acetic acid;
[4-chloro-2-[[hexahydro-4-(phenylacetyl)-1H-1,4-diazepin-1-yl]methyl]phenoxy]-acetic acid;
[4-Fluoro-2-[4-(phenyl)acetyl-1-piperazinyl]methyl]phenoxy]-acetic acid;
[4-Fluoro-2-[[4-[(phenyl)sulfonyl]-1-piperazinyl]methyl]phenoxy]-acetic acid;
[4-Fluoro-2-[[4-[(phenylmethyl)sulfonyl]-1-piperazinyl]methyl]phenoxy]-acetic acid;
(2S)-2-[4-fluoro-2-[[4-(phenylacetyl)-1-piperazinyl]methyl]phenoxy]-propanoic acid;
(2S)-2-[4-fluoro-2-[[4-(phenylsulfonyl)-1-piperazinyl]methyl]phenoxy]-propanoic acid;
(2S)-2-[4-fluoro-2-[[4-[(phenylmethyl)sulfonyl]-1-piperazinyl]methyl]phenoxy]-propanoic acid;
[4-chloro-2-[[methyl[1-(phenylsulfonyl)-3-pyrrolidinyl]amino]methyl]phenoxy]-acetic acid;
[4-Cyano-2-[[(3S)-3-methyl-4-(phenylacetyl)-1-piperazinyl]methyl]phenoxy]acetic acid;
[4-Methyl-2-[[(3S)-3-methyl-4-(phenylacetyl)-1-piperazinyl]methyl]phenoxy]acetic acid;
[2-[[(3S)-3-Methyl-4-(phenylacetyl)-1-piperazinyl]methyl]-4-(trifluoromethyl)phenoxy]acetic acid;
[4-(1-methylethyl)-2-[[4-(phenylsulfonyl)-1piperazinyl]methyl]phenoxy]acetic acid;
[4-chloro-2-[[(3S)-4-[(4-fluorophenyl)acetyl]-3-methyl-1-piperazinyl]methyl]phenoxy]-acetic acid;
[4-chloro-2-[[(3S)-4-[(2,4-difluorophenyl)acetyl]-3-methyl-1-piperazinyl]methyl]phenoxy]-acetic acid;
[4-chloro-2-[[(3S)-4-[(3-fluorophenyl)acetyl]-3-methyl-1-piperazinyl]methyl]phenoxy]-acetic acid;
[4-chloro-2-[[(3S)-4-[(3-chlorophenyl)acetyl]-3-methyl-1-piperazinyl]methyl]phenoxy]-acetic acid;
[4-chloro-2-[[(3S)-4-[(2-chlorophenyl)acetyl]-3-methyl-1-piperazinyl]methyl]phenoxy]-acetic acid;
[4-chloro-2-[[(3S)-4-[[2-fluoro-4-(trifluoromethyl)phenyl]acetyl]-3-methyl-1-piperazinyl]methyl]phenoxy]-acetic acid;
[4-chloro-2-[[(3S)-4-[(3,4-dichlorophenyl)acetyl]-3-methyl-1-piperazinyl]methyl]phenoxy]-acetic acid;
[4-chloro-2-[[(3S)-[(2,4-dichlorophenyl)acetyl]-3-methyl-1-piperazinyl]methyl]phenoxy]acetic acid;

[4-chloro-2-[[(3S)-3-methyl-4-[[4-(trifluoromethyl)phenyl]acetyl]-1-piperazinyl]methyl]phenoxy]-acetic acid;
[4-chloro-2-[[(3S)-3-methyl-4-[(4-methylphenyl)acetyl]-4-piperazinyl]methyl]phenoxy]-acetic acid;
[4-chloro-2-[[(3S)-4-[(4-chloro-2-fluorophenyl)acetyl]-3-methyl-1-piperazinyl]methyl]phenoxy]-acetic acid;
[4-chloro-2-[[(3S)-4-[(3-fluoro-4-methylphenyl)acetyl]-3-methyl-1-piperazinyl]methyl]phenoxy]-acetic acid;
[4-chloro-2-[[(3S)-4-[[3-fluoro-4-(trifluoromethyl)phenyl]acetyl]-3-methyl-1-piperazinyl]methyl]phenoxy]-acetic acid;
[4-chloro-2-[[(3S)-3-methyl-4-[[4-(trifluoromethoxy)phenyl]acetyl]-1-piperazinyl]methyl]phenoxy]-acetic acid;
[4-chloro-2-[[(3S)-4-[2-(4-chlorophenyl)-2-methyl-1-oxopropyl]-3-methyl-1-piperazinyl]methyl]phenoxy]-acetic acid;
[4-chloro-2-[[(3S)-4-[(4-methoxyphenyl)acetyl]-3-methyl-1-piperazinyl]methyl]phenoxy]-acetic acid;
[2-[[(3S)-4-[(4-chlorophenyl)acetyl]-3-methyl-1-piperazinyl]methyl]-4-(trifluoromethyl)phenoxy]-acetic acid;
[2-[[(3S)-4-[(4-fluorophenyl)acetyl]-3-methyl-1-piperazinyl]methyl]-4-(trifluoromethyl)phenoxy]-acetic acid
(2S)-2-[4-chloro-2-[(3S)-4-[(4-chlorophenyl)acetyl]-3-methyl-1-piperazinyl]phenoxy]-propanoic acid;
(2S)-2-[4-chloro-2-[(3S)-4-[(4-fluorophenyl)acetyl]-3-methyl-1-piperazinyl]phenoxy]-propanoic acid;
(2S)-2-[4-chloro-2-[[(3S)-3-methyl-4-(phenylacetyl)-1-piperazinyl]methyl]phenoxy]-propanoic acid;
(2S)-2-[4-chloro-2-[[(3S)-3-methyl-4-[(4-methylphenyl)acetyl]-1-piperazinyl]methyl]phenoxy]-propanoic acid;
(2S)-2-[4-chloro-2-[[(3S)-4-[(4-methoxyphenyl)acetyl]-3-methyl-1-piperazinyl]methyl]phenoxy]-propanoic acid;
(2S)-2-[4-chloro-2-[[(3S)-4-[(3,4-dichlorophenyl)acetyl]-3-methyl-1-piperazinyl]methyl]phenoxy]-propanoic acid;
(2S)-2-[4-chloro-2-[[(3S)-3-methyl-4-[[4-(trifluoromethyl)phenyl]acetyl]-1-piperazinyl]methyl]phenoxy]-propanoic acid; r
(2S)-2-[4-chloro-2-[(3S)-4-[[2-fluoro-4-(trifluoromethyl)phenyl]acetyl]-3-methyl-1-piperazinyl]methylphenoxy]-propanoic acid;
(2S)-2-[4-chloro-2-[(3S)-4-[(2,4-dichlorophenyl)acetyl]-3-methyl-1-piperazinyl]methylphenoxy]-propanoic acid;
(2S)-2-[4-chloro-2-[(3S)-4-[(4-chloro-2-fluorophenyl)acetyl]-3-methyl-1-piperazinyl]methylphenoxy]-propanoic acid;
(2S)-2-[4-chloro-2-[(3S)-3-methyl-4-[[4-(1-methylethyl)phenyl]acetyl]-1-piperazinyl]methylphenoxy]-propanoic acid;
[2-[(3S)-3-methyl-4-(phenylacetyl)-1-piperazinyl]-4-(trifluoromethyl)methylphenoxy]-acetic acid;
2-[4-chloro-2-[(3S)-3-methyl-4-(phenylsulfonyl)-1-piperazinyl]methylphenoxy]-2-methyl-propanoic acid;
[4-chloro-2-[[(3S)-3-(1-methylethyl)-4-(phenylacetyl)-1-piperazinyl]methyl]phenoxy]-acetic acid;
(2S)-2-[4-chloro-2-[[3-oxo-4-(phenylmethyl)-1-piperazinyl]methyl]phenoxy]-propanoic acid;
and pharmaceutically acceptable salts thereof.

Certain compounds of formula (I) are capable of existing in stereoisomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

It will be appreciated by those skilled in the art that in the processes of the present invention certain functional groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (I) can be prepared by reaction of a compound of formula (II):

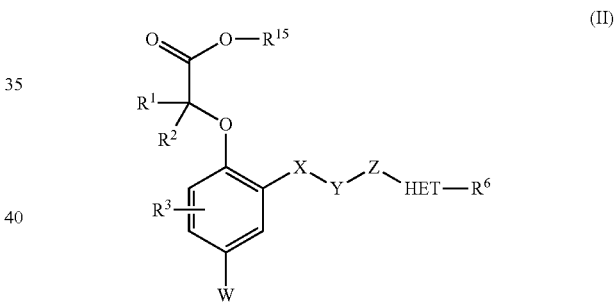

Where $R^{15}$ is methyl, ethyl or tertiary butyl, and can be removed under acidic or basic conditions for example by stirring in trifluoroacetic acid or dilute sodium hydroxide in a suitable solvent such as dichloromethane, THF or methanol. $R^1$, $R^2$, $R^3$, $R^6$, W, X, Y and Z are as defined in compounds of formula (I) or protected derivatives thereof.

Compounds of formula (II) are prepared from compounds of formula (III) as described in Route A.

When Z is $SO_2$, or C(O) the compounds of formula (III) are reacted with sulfonyl chlorides or acid chlorides of formula (IV) in which L=Chlorine. The reaction is carried out in in the presence of a base such as triethylamine, aqueous sodium hydrogen carbonate or potassium carbonate in a suitable organic solvent such as dichloromethane. When Z is alkyl compounds of formula (III) are reacted with alkyl chlorides using a suitable base such as triethylamine or sodium hydride in an organic solvent such as DMF or dichloromethane.

When L=OH and Z=C(O) the reaction is carried out using a coupling reagent such as HATU in a suitable polar organic solvent such as DMF or NMP.

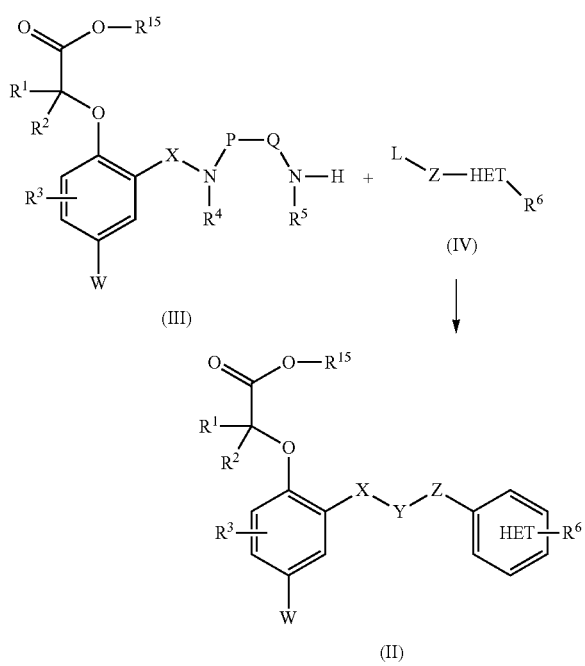

(III)

(II)

Route A

Where $R^1$, $R^2$, $R^3$, $R^4$, $R^5$, $R^6$, $R^{15}$, P, Q, W, X, Y and Z are as defined in compounds of formula (II) or protected derivatives thereof. Compounds of formula (IV) are commercially available or can be prepared readily by those skilled in the art.

Compounds of formula (III) can be prepared from compounds of formula (V) by reacting with a diamine compound of formula (VI), by a reductive amination using triacetoxy borohydride in a suitable organic solvent for example NMP, THF or dichloromethane.

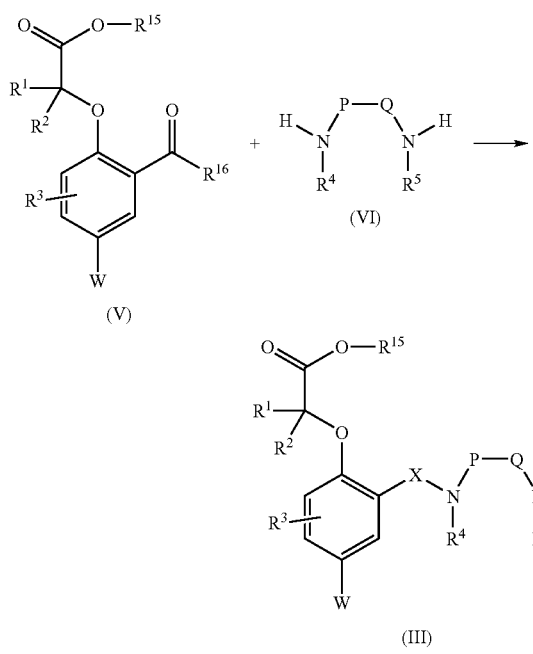

(III)

Where $R^1$, $R^2$, $R^3$, $R^4$, $R^5$, $R^{15}$, P, Q, W, X, Y and Z are as defined in compounds of formula (II) or protected derivatives thereof. $R^{16}$ is hydrogen or $C_1$-$C_6$ alkyl as defined for X in compounds of formula (I).

The diamine compound of formula (VI) is monoprotected with a suitable amine protecting group such as BOC (tert-butyl carbonyl). This protecting group is subsequently removed under acidic conditions, for example TFA.

Compounds of formula (VIa) where the amine is mono-protected with the BOC protecting group are commercially available or may be protected by reacting with compounds of formula (VI) with BOC anhydride in presence of a base for example, triethylamine in a suitable organic solvent such as dichloromethane.

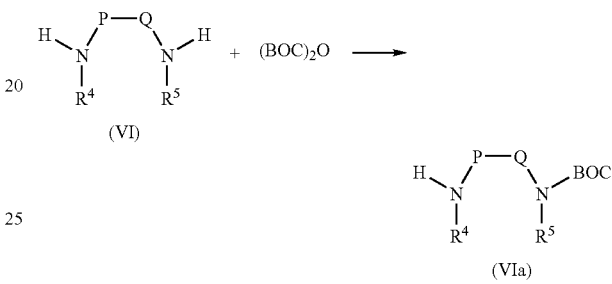

(VIa)

Certain compounds of formula (VIa) are prepared from compounds of formula (VIb).

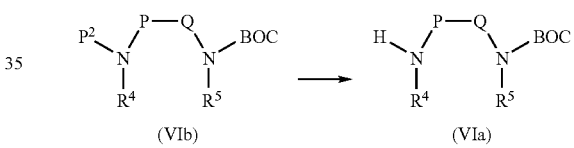

Where P2 is benzyl or trityl group. The benzyl protecting group is selectively removed by standard hydrogenation conditions Using palladium on charcoal as catalyst in a solvent such is as ethanol. The trityl protecting group can selectively be removed by reacting with acid such as dilute HCl in a suitable organic solvent such as ethanol.

Compounds of formula (VIb) can be formed as outlined in Route B:

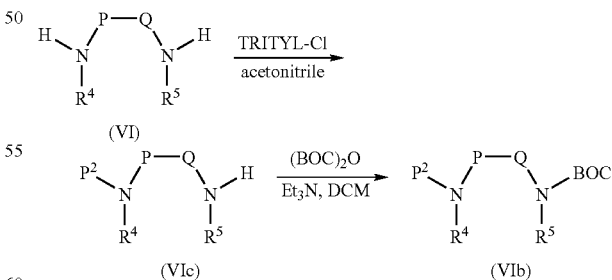

Route B

Where $R^4$, $R^5$, P, Q, and $P^2$ are as defined previously for compounds of formula (I) or protected derivatives thereof. $P^2$ is defined as for compounds of formula (VIb).

Some compounds of formula (VIb) are prepared as outlined in Route C (according to the method of WO03022835)

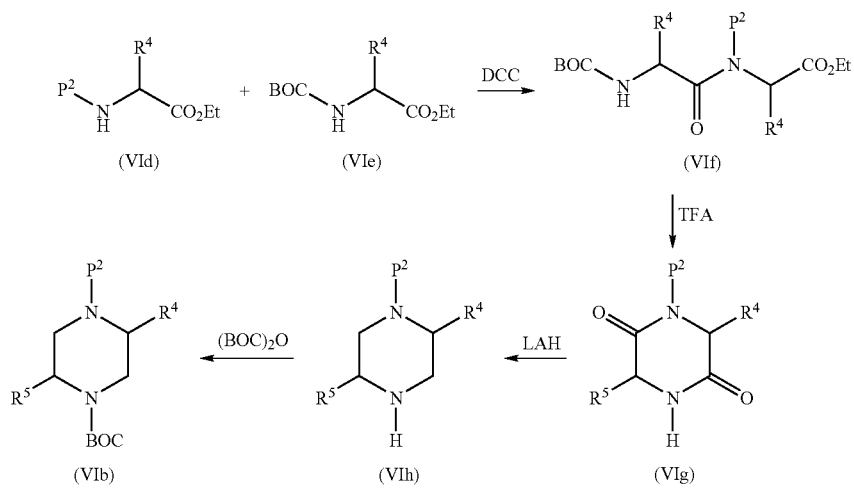

Route C

Compounds of formula (VId) and (VIe) are reacted together in the presence of a coupling reagent such as dicylohexanecarbodiimide in a suitable organic solvent such as dichloromethane at 0° C. Compounds of formula (VIf) are reacted with a strong acid such as TFA in a suitable solvent such as dichloromethane to give compounds of formula (VIg). The diketopipearazines of formula (VIg) can be reduced using lithiumaluminium hydride at 0° C. in a suitable solvent such as THF to give compounds of formula (VIh). The compounds of formula (VIh) are reprotected with the BOC group as described previously to give compounds of formula (VIb).

Compounds of formula (V) can be prepared from compounds of formula (VII), by reacting the phenolic compound of formula (V) with $L^2C(R^1, R^2)CO_2R^{15}$ in the presence of a base such as potassium carbonate in a suitable solvent such as DMF.

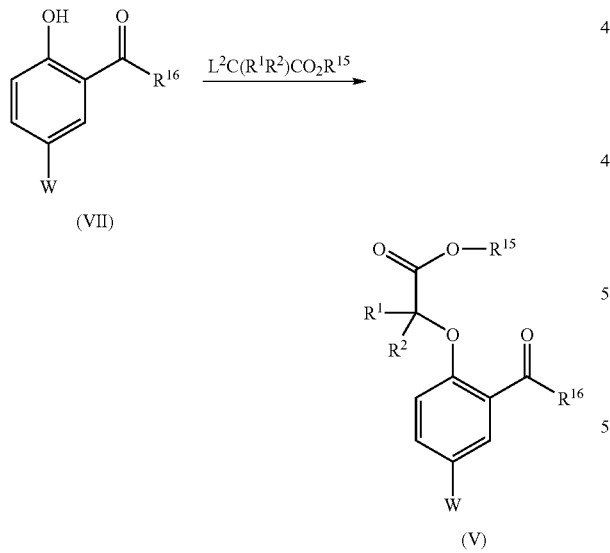

Where $R^{16}$ is hydrogen or $C_1$-$C_6$ alkyl as defined for X in compounds of formula (I) $R^1$, $R^2$, and W are as defined in compounds of formula (I) or protected derivatives thereof. $L^2$ is a leaving group such as tosylate or a halogen atom, suitably bromine or chlorine.

Compounds of formula (VII) can be prepared from compounds of formula (VIII), by ortho lithiation using a suitable base, such as butyl lithium. The reaction is carried out at −78° C. in an anhydrous solvent such as THF.

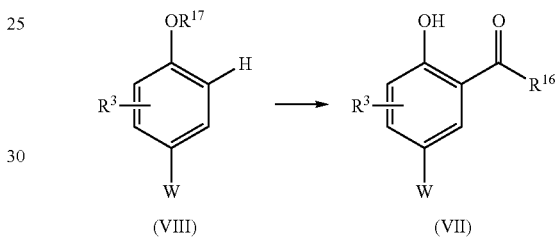

Where W and $R^3$ are as defined for compounds of formula (I). $R^{17}$ is a suitable alcohol protecting group, for example tetrahydropyran or benzyl.

Alternatively, compounds of formula (III) can be prepared as outlined in route D:

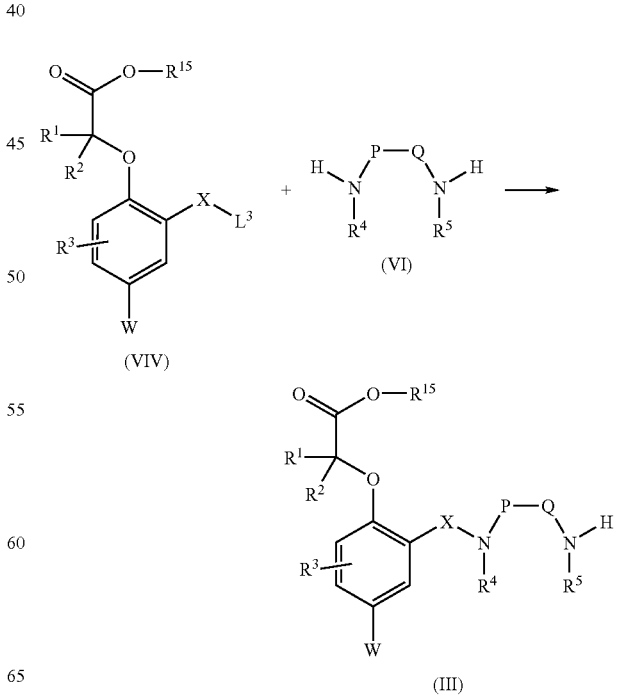

Route D

Where $R^1, R^2, R^3, R^4, R^5, R^{15}, P, Q, W$ and $X$ are as defined in compounds of formula is (II) or protected derivatives thereof. $L^3$ is a suitable leaving group such as mesylate or halogen, preferably chloro. The reaction is carried out in a suitable organic solvent such as dichloromethane in the presence of base such as triethylamine.

The sequence of any of the reactions outlined above can be reversed. For example, compounds of formula (H) may also be prepared as outlined in route E:

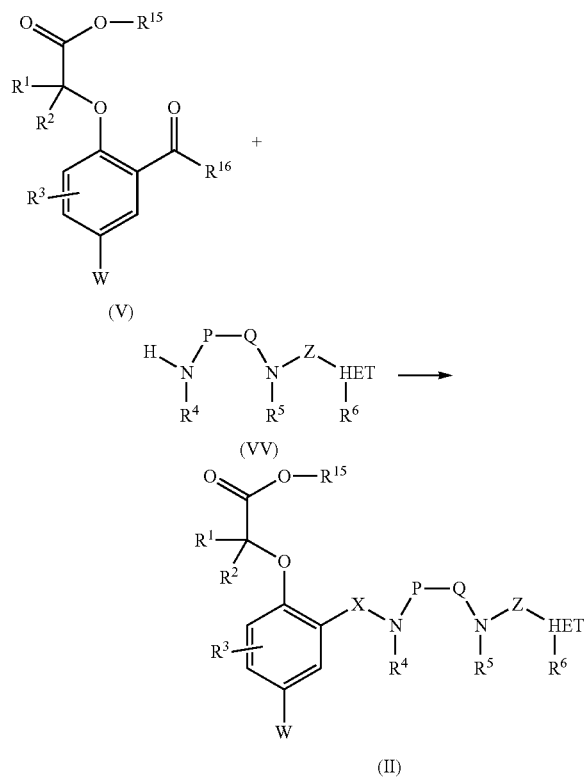

Compounds of formula (VV) can be reacted with compounds of formula (V) by reductive animation as outlined previously. Where $R^1, R^2, R^3, R^4, R^5, R^6, R^{15}, P, Q, W, X, Z$ and HET are as defined in compounds of formula (II) or protected derivatives thereof.

Compounds of formula (VV) can be prepared from compounds of formula (VI) by reacting with a compound of formula (IV) as described previously in route A.

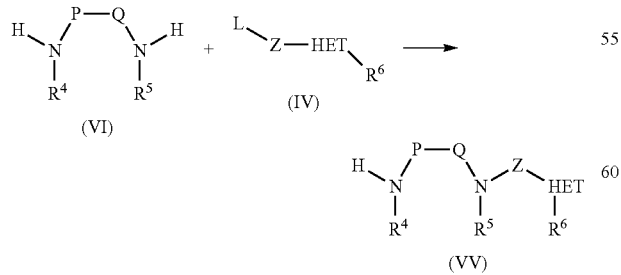

The amino group of compounds of formula (VI) may need to be protected prior to reaction with compounds of formula (IV). Suitable protecting groups are BOC, trityl or benzyl, which can be removed readily using the procedures described previously. Some protected compounds of formula (VI) are commercially available.

In a further aspect, the present invention provides the use of a compound of formula (I), a prodrug, pharmaceutically acceptable salt or solvate thereof for use in therapy.

The compounds of formula (I) have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

(1) (the respiratory tract) obstructive airways diseases including: asthma (such as bronchial, allergic, intrinsic, extrinsic and dust asthma particularly chronic or inveterate asthma (e.g. late asthma and airways hyper-responsiveness)); chronic obstructive pulmonary disease (COPD)(such as irreversible COPD); bronchitis (including eosinophilic bronchitis); acute, allergic, atrophic rhinitis or chronic rhinitis rhinitis medicamentosa, membranous rhinitis (including croupous, fibrinous and pseudomembranous rhinitis), scrofoulous rhinitis, perennial allergic rhinitis, seasonal rhinitis (including rhinitis nervosa (hay fever) and vasomotor rhinitis); nasal polyposis; sarcoidosis; farmer's lung and related diseases; fibroid lung; idiopathic interstitial pneumonia; cystic fibrosis; antitussive activity; treatment of chronic cough associated with inflammation or iatrogenic induced;

(2) (bone and joints) arthrides including rheumatic, infectious, autoimmune, seronegative, spondyloarthropathies (such as ankylosing spondylitis, psoriatic arthritis and Reiter's disease), Behcet's disease, Sjogren's syndrome and systemic sclerosis;

(3) (skin and eyes) psoriasis, atopical dermatitis, contact dermatitis, other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, chronic skin ulcers, uveitis, Alopecia areatacorneal ulcer and vernal conjunctivitis;

(4) (gastrointestinal tract) Coeliac disease, proctitis, eosinopilic gastro-enteritis, mastocytosis, Crohn's disease, ulcerative colitis, irritable bowel disease; food-related allergies which have effects remote from the gut, (such as migraine, rhinitis and eczema);

(5) (central and peripheral nervous system) Neurodegenerative diseases and dementia disorders (such as Alzheimer's disease, amyotrophic lateral sclerosis and other motor neuron diseases, Creutzfeldt-Jacob's disease and other prion diseases, HIV encephalopathy (ADDS dementia complex), Huntington's disease, frontotemporal dementia, Lewy body dementia and vascular dementia), polyneuropathies (such as Guillain-Barré syndrome, chronic inflammatory demyelinating polyradiculoneuropathy, multifocal motor neuropathy), plexopathies, CNS demyelination (such as multiple sclerosis, acute disseminated/haemorrhagic encephalomyelitis, and subacute sclerosing panencephalitis), neuromuscular disorders (such as myasthenia gravis and Lambert-Eaton syndrome), spinal disorders (such as tropical spastic paraparesis, and stiff-man syndrome), paraneoplastic syndromes (such as cerebellar degeneration and encephalomyelitis), CNS trauma, migraine and stroke.

(6) (other tissues and systemic disease) atherosclerosis, acquired Immunodeficiency Syndrome (ADDS), lupus erythematosus; systemic lupus, erythematosus; Hashimoto's thyroiditis, type I diabetes, nephrotic syndrome, eosinophilia fascitis, hyper IgE syndrome, lepromatous leprosy, idiopathic thrombocytopenia pupura; post-operative adhesions, sepsis and ischemic/reperfusion injury in the heart, brain, peripheral limbs hepatitis (alcoholic, steatohepatitis and chronic viral), glomerulonephritis, renal impairment, chronic renal failure and other organs (7) (allograft rejection) acute and chronic following, for example, transplantation of kidney, heart, liver, lung, bone marrow, skin and cornea; and chronic graft versus is host disease;

(8) Diseases associated with raised levels of $PGD_2$ or its metabolites.

(1) (respiratory tract)—obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus.

(2) (bone and joints) arthritides associated with or including osteoarthritis/osteoarthrosis, both primary and secondary to e.g. congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection-related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and is undifferentiated connective tissue disease; inflammatory myopathies including dermatomyositis and polymyositis; polymyalgia rheumatica; juvenile arthritis including idiopathic inflammatory arthritides of whatever joint distribution and associated syndromes, and rheumatic fever and its systemic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies.

(3) (skin) psoriasis, atopic dermatitis, contact dermatitis or other eczematous dermatoses, and delayed-type hypersensitivity reactions; phyto- and photodermatitis; seborrhoeic dermatitis, dermatitis herpetiformis, lichen planus, lichen sclerosus et atrophica, pyoderma gangrenosum, skin sarcoid, discoid lupus erythematosus, pemphigus, pemphigoid, epidermolysis bullosa, urticaria, angioedema, vasculitides, toxic erythemas, cutaneous eosinophilias, alopecia greata, male-pattern baldness, Sweet's syndrome, Weber-Christian syndrome, erythema multiforme; cellulitis, both infective and non-infective; panniculitis; cutaneous lymphomas, non-melanoma skin cancer and other dysplastic lesions; drug-induced disorders including fixed drug eruptions.

(4) (eyes) blepharitis; conjunctivitis, including perennial and vernal allergic conjunctivitis; iritis; anterior and posterior uveitis; choroiditis; autoimmune; degenerative or inflammatory disorders affecting the retina; ophthalmitis including sympathetic ophthalmitis; sarcoidosis; infections including viral, fungal, and bacterial.

(5) (gastrointestinal tract) glossitis, gingivitis, periodontitis; oesophagitis, including reflux; eosinophilic gastroenteritis, mastocytosis, Crohn's disease, colitis including ulcerative colitis, proctitis, pruritis ani; coeliac disease, irritable bowel syndrome, and food-related allergies which may have effects remote from the gut (for example migraine, rhinitis or eczema).

(6) (abdominal) hepatitis, including autoimmune, alcoholic and viral; fibrosis and cirrhosis of the liver; cholecystitis; pancreatitis, both acute and chronic.

(7) (genitourinary) nephritis including interstitial and glomerulonephritis; nephrotic syndrome; cystitis including acute and chronic (interstitial) cystitis and Hunner's ulcer; acute and chronic urethritis, prostatitis, epididymitis, oophoritis and salpingitis; vulvo-vaginitis; Peyronie's disease; erectile dysfunction (both male and female).

(8) (Allograft rejection) acute and chronic following, for example, transplantation of kidney, heart, liver, lung, bone marrow, skin or cornea or following blood transfusion; or chronic graft versus host disease;

(9) (CNS) Alzheimer's disease and other dementing disorders including CJD and nvCJD; amyloidosis; multiple sclerosis and other demyelinating syndromes; cerebral atherosclerosis and vasculitis; temporal arteritis; myasthenia gravis; acute and chronic pain (acute, intermittent or persistent, whether of central or peripheral origin) including visceral pain, headache, migraine, trigeminal neuralgia, atypical facial pain, joint and bone pain, pain arising from cancer and tumor invasion, neuropathic pain syndromes including diabetic, post-herpetic, and HIV-associated neuropathies; neurosarcoidosis; central and peripheral nervous system complications of malignant, infectious or autoimmune processes.

(10) Other auto-immune and allergic disorders including Hashimoto's thyroiditis, Graves' disease, Addison's disease, diabetes mellitus, idiopathic thrombocytopaenic purpura, eosinophilic fasciitis, hyper-IgE syndrome, antiphospholipid syndrome.

(11) Other disorders with an inflammatory or immunological component; including acquired immune deficiency syndrome (AIDS), leprosy, Sezary syndrome, and paraneoplastic syndromes.

(12) (Cardiovascular); atherosclerosis, affecting the coronary and peripheral circulation; is pericarditis; myocarditis, inflammatory and auto-immune cardiomyopathies including myocardial sarcoid; ischaemic reperfusion injuries; endocarditis, valvulitis, and aortitis including infective (e.g. syphilitic); vasculitides; disorders of the proximal and peripheral veins including phlebitis and thrombosis, including deep vein thrombosis and complications of varicose veins.

(13) (Oncology) treatment of common cancers including prostate, breast, lung, ovarian, pancreatic, bowel and colon, stomach, skin and brain tumors and malignancies affecting the bone marrow (including the leukaemias) and lymphoproliferative systems, such as Hodgkin's and non-Hodgkin's lymphoma; including the prevention and treatment of metastatic disease and tumour recurrences, and paraneoplastic syndromes.

(14) Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof, as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

The invention further relates to combination therapies wherein a compound of formula (1) or a pharmaceutically acceptable salt, solvate or in vivo hydrolysable ester thereof, or a pharmaceutical composition or formulation comprising a compound of formula (1) is administered concurrently or sequentially or as a combined preparation with another therapeutic agent or agents, for the treatment of one or more of the conditions listed.

In particular, for the treatment of the inflammatory diseases rheumatoid arthritis, psoriasis, inflammatory bowel disease, COPD, asthma and allergic rhinitis the compounds of the invention may be combined with agents such as tumour necrosis factor alpha (TNF-α) inhibitors such as anti-TNF monoclonal antibodies (for example Remicade, CDP-870 and adalimumab) and TNF receptor immunoglobulin molecules (such as Enbrel); non-selective cyclo-oxygenase (COX)-1/COX-2 inhibitors whether applied topically or systemically (such as piroxicam, diclofenac, propionic acids such as naproxen, flubiprofen, fenoprofen, ketoprofen and ibuprofen, fenamates such as mefenamic acid, indomethacin, sulindac, azapropazone, pyrazolones such as phenylbutazone, salicylates such as aspirin), COX-2 inhibitors (such as meloxicam, celecoxib, rofecoxib, valdecoxib, lumarocoxib, parecoxib and etoricoxib); glucocorticosteroids (whether administered by topical, oral, intramuscular, intravenous, or intra-articular routes); methotrexate, lefunomide; hydroxychloroquine, d-penicillamine, auranofin or other parenteral or oral gold preparations.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as; zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonist for leukotrienes (LT)B4, LTC4, LTD4, and LTE4. selected from the group consisting of the phenothiazin-3-1s such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a phosphodiesterase (PDE) inhibitor such as the methylxanthanines including theophylline and aminophylline; and selective PDE isoenzyme inhibitors including PDE4 inhibitors and inhibitors of the isoform PDE4D, and inhibitors of PDE5.

The present invention still further relates to the combination of a compound of the invention together with histamine type 1 receptor antagonists such as cetirizine, loratadine, desloratadine, fexofenadine, acrivastine, terfenadine, astemizole, azelastine, levocabastine, chlorpheniramine, promethazine, cyclizine, and mizolastine applied orally, topically or parenterally.

The present invention still further relates to the combination of a compound of the invention together with a gastroprotective histamine type 2 receptor antagonist.

The present invention still further relates to the combination of a compound of the invention with antagonists of the histamine type 4 receptor.

The present invention still further relates to the combination of a compound of the invention together with an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride, and ethylnorepinephrine hydrochloride.

The present invention still further relates to the combination of a compound of the invention together with anticholinergic agents including muscarinic receptor (M1, M2, and M3) antagonists such as atropine, hyoscine, glycpyrrrolate, ipratropium bromide; tiotropium bromide; oxitropium bromide; pirenzepine; and telenzepine.

The present invention still further relates to the combination of a compound of the invention together with a beta-adrenoceptor agonist (including beta receptor subtypes 1-4)

such as isoprenaline, salbutamol, formoterol, salmeterol, terbutaline, orciprenaline, bitolterol mesylate, and pirbuterol.

The present invention still further relates to the combination of a compound of the invention together with a chromone, including sodium cromoglycate and nedocromil sodium.

The present invention still further relates to the combination of a compound of the invention together with an insulin-like growth factor type I (IGF-1) mimetic.

The present invention still further relates to the combination of a compound of the invention together with an inhaled glucocorticoid, such as flunisolide, triamcinolone acetonide, beclomethasone dipropionate, budesonide, fluticasone propionate, ciclesonide, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-9 and MMP-12.

The present invention still further relates to the combination of a compound of the invention together with modulators of chemokine receptor function such as antagonists of CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the $C—X_3—C$ family.

The present invention still further relates to the combination of a compound of the invention together with a cytokine or modulator of cytokine function, including alpha-, beta-, and gamma-interferon; interleukins (IL) including IL1 to 15, and interleukin antagonists or inhibitors, including agents which act on cytokine signalling pathways.

The present invention still further relates to the combination of a compound of the invention together with an immunoglobulin (Ig) or Ig preparation or an antagonist or antibody modulating Ig function such as anti-IgE (omalizumab).

The present invention still further relates to the combination of a compound of the invention together with other systemic or topically-applied anti-inflammatory agents including thalidomide and derivatives, retinoids, dithranol, and calcipotriol.

The present invention still further relates to the combination of a compound of the invention together with an antibacterial agent including penicillin derivatives, tetracyclines, macrolides, beta-lactams, fluoroquinolones, and inhaled aminoglycosides; and antiviral agents including acyclovir, famciclovir, valaciclovir, ganciclovir, cidofovir; amantadine, rimantadine; ribavirin; zanamavir and oseltamavir; protease inhibitors such as indinavir, nelfinavir, ritonavir, and saquinavir; nucleoside reverse transcriptase inhibitors such as didanosine, lamivudine, stavudine, zalcitabine, zidovudine; non-nucleoside reverse transcriptase inhibitors such as nevirapine, efavirenz.

The present invention still further relates to the combination of a compound of the invention together with cardiovascular agents such as calcium channel blockers, beta-adrenoceptor blockers, angiotensin-converting enzyme (ACE) inhibitors, angiotensin-2 receptor antagonists; lipid lowering agents such as statins, and fibrates; modulators of blood cell morphology such as pentoxyfylline; thrombolytics, and anti-coagulants including platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, nicotine agonists, dopamine agonists and inhibitors of neuronal nitric oxide synthase), and anti-Alzheimer's drugs such as donepezil, tacrine, COX-2 inhibitors, propentofylline or metrifonate.

The present invention still further relates to the combination of a compound of the invention together with agents for the treatment of acute and chronic pain, including centrally and peripherally-acting analgesics such as opioid analogues and derivatives, carbamazepine, phenyloin, sodium valproate, amitryptiline and other antidepressant agents, and non-steroidal anti-inflammatory agents.

The present invention still further relates to the combination of a compound of the invention together with parenterally or topically-applied local anaesthetic agents such as lignocaine.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-$B.sub1.$- and $B.sub2.$-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin $NK.sub1.$ and $NK.sub3.$ receptor antagonists selected from the group consisting of NKP-608C; SB-233412 (talnetant); and D-4418; (xx) elastase inhibitors selected from the group consisting of UT-77 and ZD-0892; (xxi) TNF☐ converting enzyme inhibitors (TACE); (xxii) induced nitric oxide synthase inhibitors (iNOS) or (xxiii) chemoattractant receptor-homologous molecule expressed on TH2 cells, (CRTH2 antagonists) (xxiv) inhibitors of P38

The compounds of the present invention may also be used in combination with anti-osteoporosis agents including hormonal agents such as raloxifene, and biphosphonates such as alendronate.

The compounds of the invention may also be used in combination with existing therapeutic agents for the treatment of osteoarthritis. Suitable agents to be used in combination include standard non-steroidal anti-inflammatory agents (hereinafter NSAIDs) such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 inhibitors such as celecoxib, valdecoxib, rofecoxib and etoricoxib, analgesics, and intra-articular therapies such as corticosteroids and hyaluronic acid derivatives, and nutritional supplements such as glucosamine.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel; antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecins);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as is finasteride;

(iii) Agents which inhibit cancer cell invasion (for example metalloproteinase inhibitors like marimastat and inhibitors of urokinase plasminogen activator receptor function); (iv) inhibitors of growth factor function, for example such inhibitors include growth factor antibodies, growth factor receptor antibodies (for example the anti-erbb2 antibody trastuzumab and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab, compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention will now be illustrated by the following non-limiting examples in which, unless stated otherwise:

(i) when given, $^1$H NMR data is quoted in the form of delta values for major diagnostic protons, given in parts per million (ppm) relative to tetramethylsilane (TMS) as an internal standard;

(ii) mass spectra (MS): generally only ions which indicate the parent mass are reported, and unless otherwise stated the mass ion quoted is the positive mass ion—(M+H)$^+$;

(iii) the title compounds of the examples and methods were named using the ACD/name and ACD/name batch (version 6.0) from Advanced Chemical Development Inc, Canada;

(iv) unless stated otherwise, reverse phase HPLC was conducted using a Symmetry, NovaPak or Ex-Terra reverse phase silica column;

(v) solvents were dried with MgSO$_4$ or Na$_2$SO$_4$ (vi) the following abbreviations are used:

EtOAc Ethylacetate
DCM Dichloromethane
NMP N-methylpyrrolidine
DMF N,N-dimethylformamide
THF tetrahydrofuran
mcpba 3-chloroperoxybenzoic acid (Aldrich 77% max)
Pd(dppf)Cl$_2$ [1,1'-Bis(diphenylphosphino)ferrocene] dichloropalladium(II), complex with dichloromethane
RT room temperature
RPHPLC reverse phase high performance liquid chromatography
h hours
HCl hydrochloric acid
BOC tertiary-butylcarbonyl
HATU O-(7-Azabenzotriazol-1-yl)-N,N,N',N'-tetramethyluronium hexafluorophosphonate

EXAMPLE 1

[2-[4-[(4-Fluorophenyl)sulfonyl]-1-piperazinyl]-4-(trifluoromethyl)phenoxy]-acetic Acid a)
Tetrahydro-2-[4-(trifluoromethyl)phenoxy]-2H-pyran A solution of 4-(Trifluoromethyl)-phenol (40 g) in dichloromethane (100 ml) was added at 0° C. dropwise to a solution of dihydropyran (53 g) in dichloromethane (100 ml) and aqueous HCl (200 µl) The reaction was allowed to reach room temperature, then quenched with saturated sodium bicarbonate (×1). The organic layer was separated and dried (MgSO$_4$), concentrated in vacuo to give the sub-title compound (81 g)

$^1$H NMR (CDCl$_3$): δ 7.53 (2H, d); 7.13 (2H, d); 5.48 (1H, t); 3.9 (1H, td); 3.63 (1H, dt); 2.1-0.5 (6H, m).

b) 2-[(tetrahydro-2H-pyran-2-yl)oxy]-5-(trifluoromethyl)-benzaldehyde n-BuLi [2.5M hexanes] (31 ml) was added over 15 minutes at −78° C. under nitrogen to a solution of the product from step a) (20.8 g) in dry THF (200 ml). After stirring for 30 min DMF (9 ml) was added and the reaction mixture was allowed to reach room temperature. The reaction was quenched with water and extracted with ethyl acetate. The organic phase was washed with water (×2), brine (×1), dried (MgSO$_4$) and concentrated in vacuo to give the sub-title compound (22.75 g)

$^1$H NMR (CDCl$_3$): δ 10.55 (1H, s); 8.11 (1H, d); 7.77 (1H, dd); 7.37 (1H, d); 5.66 (1H, s); 3.9-3.65 (2H, m), 2.1-1.5 (6H, m).

c) 2-hydroxy-5-(trifluoromethyl)-benzaldehyde

The product from part b) (22.75 g) was dissolved in THF (40 ml) and treated with 2M HCl (85 ml). After 2 hours the reaction mixture was diluted with ethyl acetate and the phases separated. The organic layer was washed (brine), dried (MgSO$_4$), concentrated in vacuo to give the sub-title compound (18 g).

MS: APCI (−ve): 189 (M−1).

d) 1,1-dimethylethyl ester[2-formyl-4-(trifluoromethyl)phenoxy]-acetic Acid

Potassium carbonate (12 g) was added to a solution of phenol (11 g) and tert-butylbromoacetate (11.5 ml) in NMP (40 ml). The reaction was stirred for 2 hours, then diluted with ethyl acetate and washed with water, brine, dried (MgSO$_4$), and concentrated in vacuo to give the sub-title compound (19 g).

$^1$H NMR (CDCl$_3$): δ 10.55 (1H, s); 8.15 (1H, d); 7.78 (1H, dd); 6.96 (1H, d); 4.72 (2H, s), 1.5 (9H, s).

e) [2-(1-piperazinylmethyl)-4-(trifluoromethyl)phenoxy]-acetic acid, 1,1-dimethylethyl Ester The product of part d) (1 g) and BOC piperidine (900 mg) were dissolved in NMP (10 ml) and sodium triacetoxy borohydride (1.7 g) was added and stirred for 1.5 hours. The reaction was quenched with water and extracted with ethyl acetate. The organic layer was washed with water, brine, dried (MgSO$_4$) and concentrated in vacuo to give the sub-title compound (1.75 g).

$^1$H NMR (CDCl$_3$):: δ 7.68 (1H, s); 7.47 (1H, d); 6.76 (1H, d), 4.57 (2H, s), 3.65 (2H, s), 3.45 (4H, t), 2.46 (4H, s), 1.48 (9H, s), 1.45 (9H, s).

The crude material (1.1 g) was dissolved DCM (30 ml) and treated with TFA (2 ml) and concentrated to give the sub-title compound (1.1 g).

$^1$H NMR (CDCl$_3$): δ 7.68 (1H, s); 7.44 (1H, dd); 6.76 (1H, d), 4.57 (2H, s), 3.64 (2H, s), 2.94 (2H, s), 2.52 (4H, t), 1.48 (9H, s).

f) [2-[[4-[(4-fluorophenyl)sulfonyl]-1-piperazinyl] methyl]-4-(trifluoromethyl)phenoxy]-acetic Acid The product from part e) (210 mg) was dissolved in DCM (15 ml) and treated with triethylamine (500 µl) and 4-fluorobenzenesulfonyl chloride (150 mg), the reaction mixture was stirred overnight. The reaction was concentrated in vacuo then redissolved in ethyl acetate, washed with NaHCO$_3$, brine, dried (MgSO$_4$) and concentrated in vacuo. The residue was purified using SCX resin (washed with MeOH and eluted with ammonia). The resulting product was dissolved in DCM and TFA (2 ml) and stirred overnight, then concentrated in vacuo. The product was further purified by LCMS directed purification to give the title compound (90 mg)

MS: APCI (−ve): 475 (M−1)

The following compounds were synthesised from the product of Example 1 part e) using the method of example 1 part f)

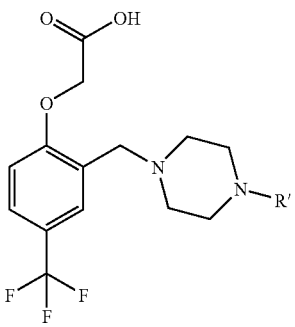

| Example number | EXAMPLE | R' | M/Z |
|---|---|---|---|
| 2 | [2-[[4-(phenylsulfonyl)-1-piperazinyl]methyl]-4-(trifluoromethyl)phenoxy]-acetic acid | 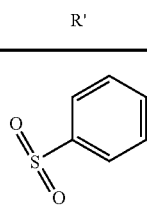 | 457 [M − H] |
| 3 | [2-[4-[[((4-cyanophenyl)sulfonyl]-1-piperazinylmethyl]]-4-(trifluoromethyl)phenoxy]-acetic acid | 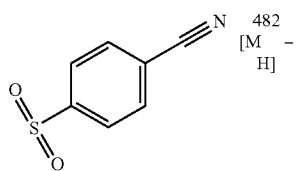 | 482 [M − H] |
| 4 | [2-[[4-[(2-fluorophenyl)sulfonyl]-1-piperazinyl]methyl)-4-(trifluoromethyl)phenoxy]-acetic acid | 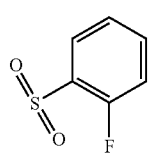 | 475 [M − H] |
| 5 | [2-[[4-[(2-methylphenyl)sulfonyl]-1-piperazinyl]methyl)-4-(trifluoromethyl)phenoxy]-acetic acid | 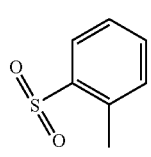 | 471 [M − H] |
| 6 | [2-[[4-[(4-nitrophenyl)sulfonyl]-1-piperazinyl)methyl)-4-(trifluoromethyl)phenoxy]-acetic acid | 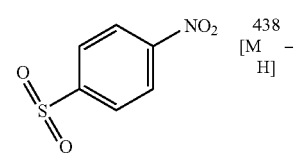 | 438 [M − H] |

Synthesis of Intermediate 7a (Used for Synthesis of Examples (7-10)

7a) [2-[(hexahydro-1H-1,4-diazepin-1-yl)methyl]-4-(trifluoromethyl)phenoxy]-1,1-dimethylethyl Ester Acetic Acid

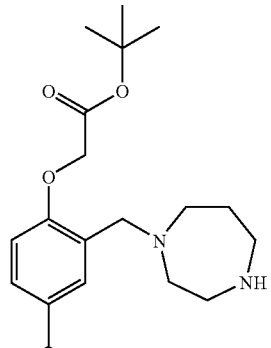

The sub-title compound was prepared by the method of Example 1 part f) using BOC-homopiperazine ([1,4]Diazepane-1-carboxylic acid tert-butyl ester) and the product from Example 1 part d)

$^1$H NMR (CDCl$_3$): δ 7.75 (1H, s); 7.45 (1H, d); 6.75 (1H, d), 4.57 (2H, s), 3.76 (2H, s), 3.6-3.45 (4H, m), 2.83-2.6 (4H, m), 1.95-1.8 (2H, m), 1.48 (18H, s).

The intermediate was dissolved in DCM (100 ml) and treated with TFA (30 ml), to give the sub-title compound.

MS: APCI (+ve): 389 (M+1)

$^1$H NMR (CDCl$_3$): δ 7.58 (1H, s); 7.49 (1H, d); 4.6 (2H, s), 3.81 (2H, s), 3.29 (4H, m), 3.21 (2H, t), 2.93 (2H, t), 2.81 (2H, t), 2.10-1.9 (2H, m), 1.48 (9H, s).

The following examples (7-10) were synthesised using intermediate 7a by the method of example 1 part f)

| Example number | EXAMPLE | R'' | M/Z [M + H] |
|---|---|---|---|
| 7 | [2-[[4-[(4-fluorophenyl)sulfonyl]hexahydro-1H-1,4-diazepin-1-yl]methyl]-4-(trifluoromethyl)phenoxy]-acetic acid | 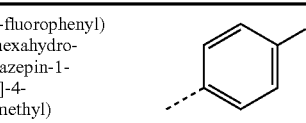 | 491.6 |

-continued

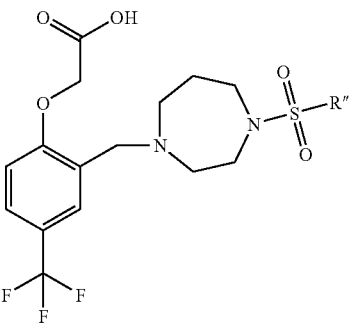

| Example number | EXAMPLE | R" | M/Z [M + H] |
|---|---|---|---|
| 8 | [2-[hexahydro-4-[[(4-methoxyphenyl)sulfonyl]-1H-1,4-diazepin-1-yl]methyl]-4-(trifluoromethyl)phenoxy]-acetic acid | 4-methoxyphenyl | 503.6 |
| 9 | [2-[[hexahydro-4-(phenylsulfonyl)-1H-1,4-diazepin-1-yl]methyl]-4-(trifluoromethyl)phenoxy]-acetic acid | phenyl | 473.6 |
| 10 | [2-[[4-[(4-cyanophenyl)sulfonyl]hexahydro-1H-1,4-diazepin-1-yl]methyl]-4-(trifluoromethyl)phenoxy]-acetic acid | 3-cyanophenyl | 498.6 |

EXAMPLE 11

[4-chloro-2-[4-(phenylsulfonyl)-1-piperazinyl]phenoxy]-acetic Acid

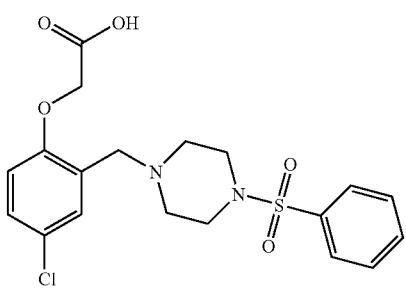

a) [4-chloro-2-(1-piperazinylmethyl)phenoxy]-acetic Acid, Ethyl Ester

The sub-title compound was prepared by the method of Example 1 part e) from (4-chloro-2-formylphenoxy)-acetic acid, ethyl ester. The sub-title compound was used directly in the following step reaction.

b) [4-chloro-2-[4-(phenylsulfonyl)-1-piperazinylmethyl]phenoxy]-acetic Acid

The product of example 11 part b (300 mg) was dissolved in THF (10 ml) and triethylamine (0.28 ml). The sulfonyl chloride (1.1 equivalents) was added and stirred for 3 h. 1M NaOH (3 ml) was added and stirred for 2 hours. Acetic acid (5 ml) was added and then the reaction mixture was concentrated in vacuo. The residue was further purified by RPHPLC to give the sub-title compound (0.19 g).

MS: APCI (−ve): 423 (M−1).

$^1$H NMR (DMSO-$d_6$) δ 7.77-7.72 (3H, m), 7.66 (2H, m), 7.22 (2H, d), 4.58 (2H, s), 3.55 (2H, s), 2.97-2.90 (4H, m), 2.57-2.50 (4H, m).

EXAMPLE 12

[4-chloro-2-[[4-[(4-fluorophenyl)sulfonyl]-1-piperazinyl]methyl]phenoxy]-acetic Acid

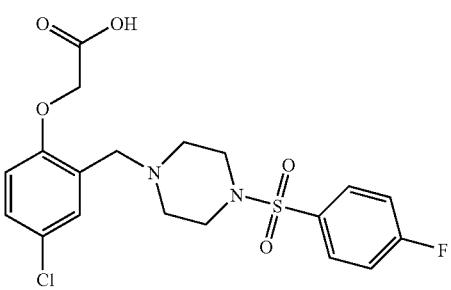 [SMILES: O=C(O)COc1ccc(Cl)cc1CN1CCN(S(=O)(=O)c2ccc(F)cc2)CC1]

The title compound was prepared from Example 11 part a) and 4-fluoro-benzene sulfonyl chloride, by the method of example 11 part b)

MS: APCI (−ve): 441 (M−1)

$^1$H NMR (DMSO-$d_6$) δ 7.81 (2H, m), 7.49 (2H, m), 7.26 (1H, m), 7.24 (1H, m), 6.94 (1H, d), 4.65 (2H, s), 3.57 (2H, s), 3.00-2.90 (4H, m), 2.61-2.51 (4H, m).

Synthesis of Intermediate Example 13b

[4-chloro-2-(1-piperazinylmethyl)phenoxy]-acetic Acid, 1,1-dimethylethyl Ester

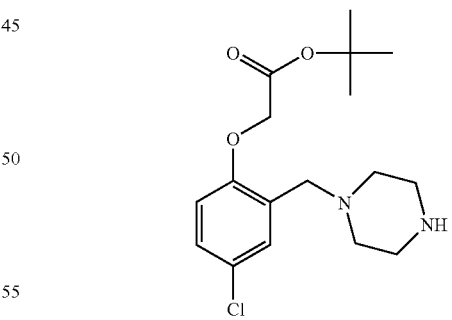

a) (4-chloro-2-formylphenoxy)-acetic Acid, 1,1-dimethylethyl Ester

The sub-title compound was prepared by the method of Example 1 part d) using 5-chloro-2-hydroxybenzaldehyde (40 g), potassium carbonate (40 g), acetone (400 ml) and tert-butyl bromoacetate (37 ml) (yield=45.5 g).

$^1$H NMR (CDCl$_3$): δ 10.5 (1H, s); 7.81 (1H, d); 7.47 (1H, dd), 6.82 (1H, d), 4.64 (2H, s), 1.48 (9H, s).

b) [4-chloro-2-(1-piperazinylmethyl)phenoxy]-acetic Acid, 1,1-dimethylethyl Ester The sub-title compound was prepared by the method of Example 1 part e) using the product of part a).

Synthesis of Examples 13-28

Examples 13-28 were synthesised using the following procedure:—

The product of example 13 part b (300 mg) was dissolved in THF (10 ml) and triethylamine (0.28 ml). The sulfonyl chloride (1.1 equivalents) was added and stirred for 3 h. 1M NaOH (3 ml) was added and stirred for 2 hours. Acetic acid (5 ml) was added and then the reaction mixture was concentrated in vacuo. The residue was further purified by RPHPLC.

| Example number | EXAMPLE | R'' | M/Z [M − H] |
|---|---|---|---|
| 13 | [4-chloro-2-[[4-[(4-chlorophenyl)sulfonyl]-1-piperazinyl]methyl]phenoxy]-acetic acid | 4-Cl-C6H4- | 457 |
| 14 | [4-chloro-2-[[4-[4-(trifluoromethyl)phenyl]methyl]sulfonyl]-1-piperazinyl]phenoxy]-acetic acid | 4-CF3-C6H4- | 491 |
| 15 | [4-chloro-2-[[4-[[4-(trifluoromethoxy)phenyl]methyl]sulfonyl]-1-piperazinyl]phenoxy]-acetic acid | 4-OCF3-C6H4- | 509 |
| 16 | [4-chloro-2-[4-[[[4-(methylsulfonyl)phenyl]sulfonyl]-1-piperazinyl]methyl]phenoxy]-acetic acid | 4-SO2Me-C6H4- | 501 |
| 17 | [4-chloro-2-[[4-[(3-fluorophenyl)sulfonyl]-1-piperazinyl]methyl]phenoxy]-acetic acid | 3-F-C6H4- | 441 |
| 18 | [4-chloro-2-[[4-[[3-(trifluoromethyl)phenyl]sulfonyl]-1-piperazinyl]methyl]phenoxy]-acetic acid | 3-CF3-C6H4- | 491 |

-continued

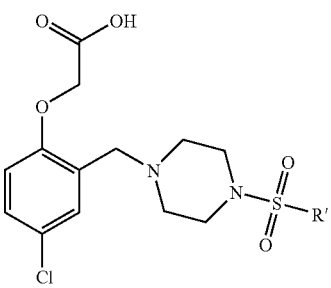

| Example number | EXAMPLE | R'' | M/Z [M − H] |
|---|---|---|---|
| 19 | [4-chloro-2-[[(3-chlorophenyl)sulfonyl]-1-piperazinyl]methyl]phenoxy]-acetic acid | 3-Cl-C6H4- | 457 |
| 20 | [4-chloro-2-[[4-[[3-(trifluoromethoxy)phenyl]sulfonyl]-1-piperazinyl]methyl]phenoxy]-acetic acid | 3-OCF3-C6H4- | 507 |
| 21 | [4-chloro-2-[[4-[[3-(difluoromethoxy)phenyl]sulfonyl]-1-piperazinyl]methyl]phenoxy]-acetic acid | 3-OCHF2-C6H4- | 489 |
| 22 | [4-chloro-2-[[4-[(3-chloro-4-fluorophenyl)sulfonyl]-1-piperazinyl]methyl]phenoxy]-acetic acid | 3-Cl-4-F-C6H3- | 474 |
| 23 | [4-chloro-2-[[4-[(3,4-dichlorophenyl)sulfonyl]-1-piperazinyl]methyl]phenoxy]-acetic acid | 3,4-Cl2-C6H3- | 492 |
| 24 | [4-chloro-2-[[4-[(3,4-difluorophenyl)sulfonyl]-1-piperazinyl]methyl]phenoxy]-acetic acid | 3,4-F2-C6H3- | 459 |
| 25 | [4-chloro-2-[[4-[(phenylmethyl)sulfonyl]-1-piperazinyl]methyl]phenoxy]-acetic acid | PhCH2- | 437 |

-continued

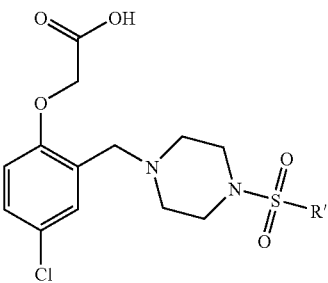

| Example number | EXAMPLE | R" | M/Z [M − H] |
|---|---|---|---|
| 26 | [4-chloro-2-[[4-[[(2-nitrophenyl)methyl]sulfonyl]-1-piperazinyl]methyl]phenoxy]-acetic acid | 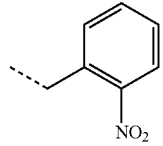 | 482 |
| 27 | [4-chloro-2-[[4-[[(3-chlorophenyl)methyl]sulfonyl]-1-piperazinyl]methyl]phenoxy]-acetic acid | 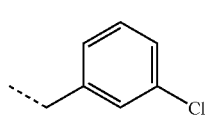 | 471 |
| 28 | [4-chloro-2-[[4-[[(4-chlorophenyl)methyl]sulfonyl]-1-piperazinyl]methyl]phenoxy]-acetic acid | 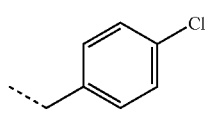 | 471 |

EXAMPLE 29

[2-[[4-(phenylacetyl)-1-piperazinyl]-methyl]-4-(trifluoromethyl)phenoxy]-acetic Acid

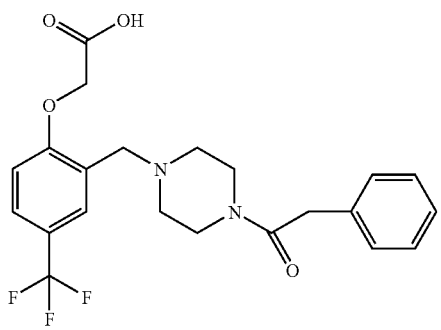 [SMILES: O=C(O)COc1ccc(C(F)(F)F)cc1CN1CCN(C(=O)Cc2ccccc2)CC1]

The product of example 1 part e) (0.1 mmol) in NMP (100 µl) and HATU (0.1 mmol) in NMP (100 µl) were added to phenylacetic acid (0.1 mmol) and stirred for 24 hours. Methanol (100 µl) was added, stirred for 5 minutes and evaporated in vacuo to dryness. TFA/DCM [1:1] (400 µl) was added and vortex mixed for 96 hours, followed by centrifugal evaporation to dryness. The product was purified by LCMS directed purification to give the title compound.

MS: APCI (−ve): 435 (M−1).

EXAMPLE 30

[4-Chloro-2-[[4-[(4-chlorophenyl)acetyl]-1-piperazinyl]methyl]phenoxy]-acetic Acid

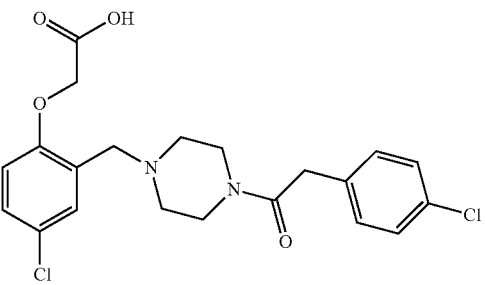 [SMILES: O=C(O)COc1ccc(Cl)cc1CN1CCN(C(=O)Cc2ccc(Cl)cc2)CC1]

The product from Example 1 part (e) (300 mg) was dissolved in THF (10 ml) and treated with triethylamine (280 followed by 4-chlorobenzeneacetyl chloride (180 mg). The reaction mixture was stirred overnight, treated with 1M NaOH (3 ml) and stirred for 3 h. The reaction was acidified with 2M HCl, diluted with ethyl acetate, washed with brine, dried (MgSO$_4$) and concentrated in vacuo. The residue was purified by RPHPLC to give the title compound (170 mg)

MS: APCI (−ve): 435 (M−1).

$^1$H NMR (DMSO-d$_6$) δ 7.35 (4H, m), 7.23 (2H, m), 7.06 (1H, d), 4.63 (2H, s), 3.73 (4H, s), 3.56 (4H, m), 2.59 (4H, m).

EXAMPLE 31

[4-Chloro-2-[[4-(1-oxo-3-phenylpropyl)-1-piperazinyl]methyl]phenoxy]-acetic Acid

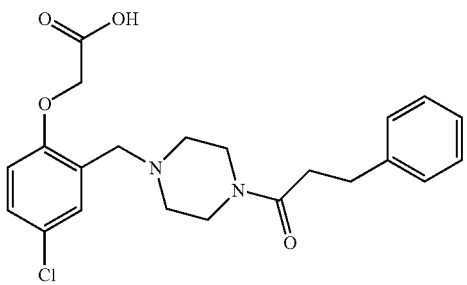 [SMILES: O=C(O)COc1ccc(Cl)cc1CN1CCN(C(=O)CCc2ccccc2)CC1]

The title compound was prepared by the method of Example 30, using the product of example 1 part (e) and benzenepropanoyl chloride.

MS: APCI (−ve): 415 (M−1).

$^1$H NMR (DMSO-d$_6$) δ 7.38 (1H, m), 7.33 (1H, m), 7.25 (4H, m), 7.18 (1H, m), 7.08 (1H, m), 4.63 (2H, s), 3.74 (2H, s), 3.53 (4H, m), 2.80 (3H, t), 2.63 (3H, t), 2.59 (4H, m).

EXAMPLE 32

[3-Chloro-2-[[4-[(4-chlorophenyl)acetyl]-1-piperazinyl]-methyl]-phenoxy]-acetic Acid

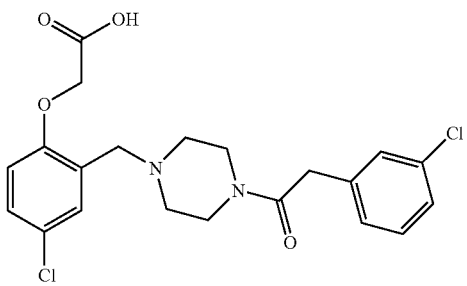 [SMILES: O=C(O)COc1ccc(Cl)cc1CN1CCN(C(=O)Cc2cccc(Cl)c2)CC1]

The product from Example 11 part (a) (300 mg) was dissolved in DMF (10 ml) and treated with HATU ((570 mg), followed by 3-chlorobenzeneacetic acid (190 mg). The reaction mixture was stirred for 18 h, treated with 1M NaOH (3 ml) and stirred for 3 h. The reaction was acidified with 2M HCl, diluted with ethyl acetate, washed with brine, dried (MgSO$_4$) and concentrated in vacuo. The residue was purified by RPHPLC to give the title compound (110 mg).

MS: APCI (−ve): 435 (M−1).

$^1$H NMR (DMSO-d$_6$) δ 7.39 (1H, d), 7.31 (4H, m), 7.18 (1H, m), 7.07 (1H, d), 4.65 (2H, s), 3.75 (4H, s), 3.58 (4H, m), 2.62 (4H, m).

EXAMPLE 33

[2-Chloro-2-[[4-[(4-chlorophenyl)acetyl]-1-piperazinyl]methyl]phenoxy]-acetic Acid

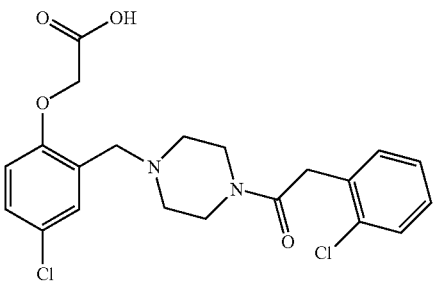 [SMILES: O=C(O)COc1ccc(Cl)cc1CN1CCN(C(=O)Cc2ccccc2Cl)CC1]

Prepared using the product of Example 11 part (a) and 2-chlorobenzeneacetic acid by the method of Example 32, to give the title compound.

MS: APCI (−ve): 435 (M−1), $^1$H NMR (DMSO-d$_6$) δ 7.41 (2H, m), 7.30 (4H, m), 7.06 (1H, d), 4.64 (2H, s), 3.82 (2H, s), 3.75 (2H, s), 3.60 (4H, m), 2.64 (4H, m).

EXAMPLE 34

[4-chloro-2-[1-[4-(phenylsulfonyl)-1-piperazinyl]methyl]phenoxy]-acetic Acid Trifluoroacetate Salt

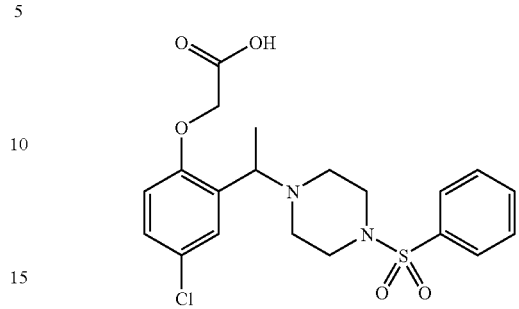

a) (2-acetyl-4-chlorophenoxy)-acetic Acid, 1,1-dimethylethyl Ester

A mixture of 1-(5-chloro-2-hydroxyphenyl)-ethanone (2 g), potassium carbonate (1.62 g) and tert-butylbromoacetate (1.73 ml) in DMF (5 ml) was stirred at ambient temperature for 16 h. Diethyl ether and water were added and the organic layer separated, it was washed with water, aqueous potassium carbonate solution, brine, dried (Na$_2$SO$_4$) and the solvent removed in vacuo to give the sub-title compound (2.84 g).

$^1$H NMR (CDCl$_3$): 7.73 (1H, d), 7.38 (1H, dd), 6.77 (1H, d), 4.60 (2H, s), 2.71 (3H, s), 1.49 (9H, s).

b) [4-chloro-2-(1-hydroxyethyl)phenoxy]-acetic Acid, 1,1-dimethylethyl Ester To the product of step a) (2.49 g) in methanol (10 ml) at 0° C. was added sodium borohydride (0.33 g) and the reaction warmed to room temperature and stirred for 2 h. Diethyl ether and water were added and the organic layer separated. It was washed with water, brine, dried (Na$_2$SO$_4$) and the solvent removed in vacuo to give the sub-title compound (2.40 g).

$^1$H NMR (CDCl$_3$): 7.34 (1H, d), 7.17 (1H, dd), 6.68 (1H, d), 5.11 (1H, quintet), 4.58 (1H, d), 4.53 (1H, d), 3.29 (1H, d), 1.53 (3H, d), 1.48 (9H, s).

c) [4-chloro-2-(1-chloroethyl)phenoxy]-acetic Acid, 1,1-dimethylethyl Ester

To the product of step b) (0.34 g) in DCM (5 ml) was added Hunigs base (1 ml) followed by methanesulfonyl chloride (0.46 ml) and the reaction stirred at room temperature for 2 h followed by heating at 45° C. for 2 h. After cooling to 0° C. the bulk of the volatiles were removed in vacuo. Diethyl ether and water were added and the organic layer separated.

It was washed with water, sat aqueous sodium bicarbonate solution, dried (Na$_2$SO$_4$) and the solvent removed in vacuo to give the sub-title compound as red oil (0.43 g).

$^1$H NMR (CDCl$_3$): 7.53 (1H, d), 7.19 (1H, dd), 6.66 (1H, d), 5.60 (1H, q), 4.57 (1H, d), 4.53 (1H, d), 1.80 (3H, d), 1.47 (9H, s).

d) [4-chloro-2-[1-[4-(phenylsulfonyl)-1-piperadinyl] ethyl]-phenoxy]-acetic Acid, 1,1-dimethylethyl Ester The product of step c) (0.23 g), potassium carbonate (0.14 g), sodium iodide (cat) and 1-(phenylsulfonyl)-piperazine (0.23 g) in DMF (2 ml) were heated at 90° C. for 15 h. After cooling to room temperature, diethyl ether and water were added and the organic layer separated. It was purified by passage through SCX resin eluting with MeCN, MeOH followed by 7M NH$_3$ in MeOH to give the product. Further purification by column chromatography (SiO$_2$, 40% diethyl ether in iso-hexane as eluent) gave the sub title product (0.12 g)

MS: APCI (+ve): 495.6 (M+1).

e) [4-chloro-2-[1-[4-(phenylsulfonyl)-1-piperazinyl]ethyl]phenoxy]-acetic Acid Trifluoroacetate Salt

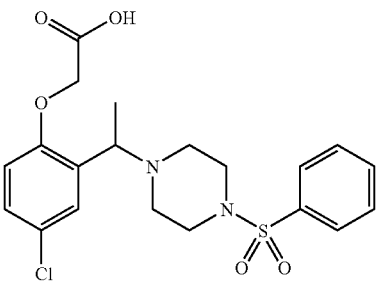 [SMILES: CC(c1cc(Cl)ccc1OCC(=O)O)N1CCN(S(=O)(=O)c2ccccc2)CC1]

The product of step d) (0.12 g) was dissolved in DCM (2 ml) and TFA (2 ml) and the reaction stirred for 64 h; then concentrated in vacuo and the resulting solid triturated with diethyl ether and concentrated in vacuo to give the sub-title compound as an off white solid (88 mg).

$^1$H NMR (DMSO-d$_6$) δ 7.77 (3H, m), 7.68 (2H, m), 7.42 (2H, m), 7.09 (1H, d), 4.81 (1H, d), 4.77 (1H, d), 4.63 (1H, s), 3.89-2.73 (8H, m), 1.52 (3H, d). MS: APCI (+ve): 437 (M+1).

EXAMPLE 35

[2-[1-(4-benzoyl-1-piperazinyl)ethyl]-4-chlorophenoxy]-acetic Acid, Trifluoroacetate Salt

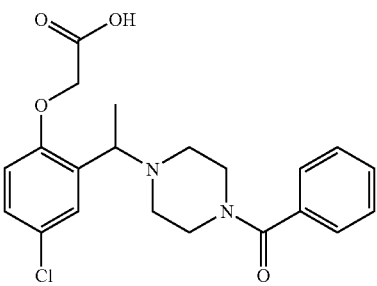 [SMILES: CC(c1cc(Cl)ccc1OCC(=O)O)N1CCN(C(=O)c2ccccc2)CC1]

Prepared from the product from Example 34 step c) and 1-benzoyl-piperazine according to the methods described in Example 34 steps d) and e) to give the sub-title compound as a white solid (35 mg).

$^1$H NMR (DMSO-d$_6$) δ 7.54 (1H, d), 7.51-7.43 (6H, m), 7.13 (1H, d), 4.84 (2H, s), 4.74 (1H, q), 4.19-2.86 (8H, m), 1.62 (3H, d).
MS: APCI (−ve): 401 (M−H).

EXAMPLE 36

[4-chloro-2-[[[1-[(phenylmethyl)sulfonyl]-3-pyrrolidinyl]amino]methyl]phenoxy]-acetic Acid

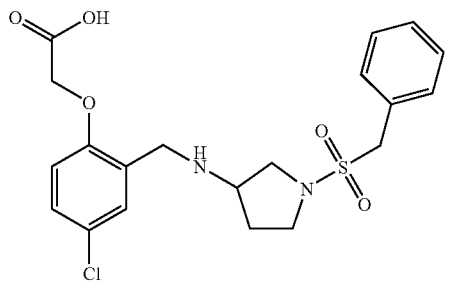 [SMILES: O=C(O)COc1ccc(Cl)cc1CNC1CCN(S(=O)(=O)Cc2ccccc2)C1]

a) [1-[(phenylmethyl)sulfonyl]-3-pyrrolidinyl]-carbamic Acid, 1,1-dimethylethyl Ester To a solution/suspension of 3-pyrrolidinyl-carbamic acid, 1,1-dimethylethyl ester (0.5 g) and triethylamine (0.38 ml) in dichloromethane (30 ml) at 0° C. was added benzenemethanesulfonyl chloride (0.51 g). The mixture was stirred at 0° C. for 30 minutes then stirred at room temperature for 2 days. The reaction was diluted with dichloromethane (20 ml) washed with water, saturated aq. NaHCO$_3$(aq), dried (MgSO$_4$) and concentrated in vacuo to give the sub-title compound (0.6 g).

$^1$H NMR (DMSO-d$_6$) δ 7.39 (5H, m), 7.15 (1H, m), 4.42 (2H, m), 4.00-3.92 (1H, m), 3.38 (1H, dd), 3.27 (1H, m), 3.15 (1H, m), 3.00 (1H, m), 1.98 (1H, m), 1.74 (1H, m), 1.39 (9H, s).

b) 1-[(phenylmethyl)sulfonyl]-3-pyrrolidinamine, Trifluoroacetic Acid Salt

The product of part (a) (0.25 g) was dissolved in dichloromethane (5 ml). The mixture was concentrated in vacuo and the residue triturated with ether to give the sub-title compound as a solid (0.23 g).

$^1$H NMR (DMSO-d$_6$) δ 8.10 (3H, s), 7.40 (5H, m), 4.49 (2H, s), 3.80 (1H, s), 1.90 (1H, m), 2.17 (1H, m), 3.24 (2H, m), 3.37 (1H, m), 3.48 (1H, m).

c) [4-chloro-2-[[[1-[(phenylmethyl)sulfonyl]-3-pyrrolidinyl]-amino]methyl]phenoxy]-acetic Acid, 1,1-dimethylethyl Ester To a solution of the product of part (b) (0.22 g) in THF (10 ml) and acetic acid (3 ml) was added the product of example 13 part (a) (0.17 g) and 3 Å molecular sieves. After 30 minutes stirring at room temperature sodium triacetoxyborohydride (0.3 g) was added and the mixture stirred for 24 h. The mixture was concentrated in vacuo and the residue dissolved in ethylacetate, washed with NaHCO$_3$ (aq), brine, dried (MgSO$_4$) and concentrated in vacuo to give a crude material. Purification by column chromatography (silica, hexane:EtOAc (1:1) as eluent) gave the sub-title compound as an oil (0.15 g).

$^1$H NMR (CDCl$_3$) δ 7.45-7.32 (5H, m), 7.22-7.15 (2H, m), 6.66 (1H, d), 4.53 (2H, d), 4.26 (2H, s), 3.74 (2H, dd), 3.43-3.17 (4H, m), 3.06 (1H, dd), 2.04-1.93 (1H, m), 1.79-1.67 (1H, m), 1.47 (9H, d).

d) [4-chloro-2-[[[1-[(phenylmethyl)sulfonyl]-3-pyrrolidinyl]amino]methyl]phenoxy]-acetic Acid To a solution of the product from part (c) (0.15 g) in dichloromethane (3 ml) was added trifluoroacetic acid (3 ml). The mixture was stirred at room temperature for 24 hours. The reaction was concentrated in vacuo and the residue triturated with ether to give the title compound as a solid (0.12 g).

$^1$H NMR (DMSO-d6) δ 7.51 (1H, d), 7.44-7.34 (6H, m), 7.11 (1H, d), 4.76 (2H, s), 4.42 (2H, s), 4.15 (2H, dd), 3.79 (1H, q), 3.60-3.52 (1H, m), 3.44-3.32 (2H, m), 3.29-3.19 (1H, m), 2.32-2.20 (1H, m), 2.05 (1H, m).
MS: APCI (−ve): 437 (M−1).

[4-chloro-2-[[[1-(phenylsulfonyl)-3-pyrrolidinyl]amino]methyl]phenoxy]-acetic Acid

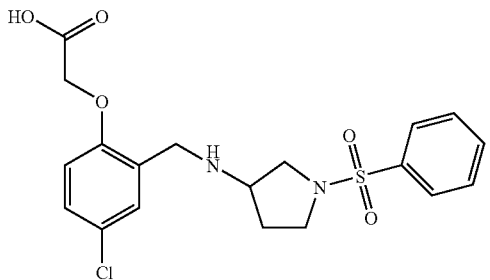 [SMILES: O=C(O)COc1ccc(Cl)cc1CNC1CCN(S(=O)(=O)c2ccccc2)C1]

a) [1-(phenylsulfonyl)-3-pyrrolidinyl]-carbamic Acid, 1,1-dimethylethyl Ester The sub-title compound was prepared by the method of Example 36 part (a) using benzenesulfonyl chloride.

$^1$H NMR (CDCl$_3$) δ 7.83 (2H, dt), 7.65-7.60 (1H, m), 7.55 (2H, dt), 4.48 (1H, s), 4.09 (1H, s), 3.46-3.32 (2H, m), 3.21 (2H, s), 2.04 (1H, dq), 1.75 (1H, s), 1.41 (9H, s).

b) 1-(phenylsulfonyl)-3-pyrrolidinamine, Trifluoroacetic Acid Salt

The sub-title compound was prepared by the method of Example 36 part (b) using the product from part (a).

$^1$H NMR (DMSO-d$_6$) δ 8.14 (3H, s), 7.84-7.80 (2H, m), 7.76 (1H, m), 7.67 (2H, t), 3.71 (1H, ddd), 3.35 (2H, m), 3.14 (2H, m), 2.05 (1H, m), 1.80 (1H, m).

c) [4-chloro-2-[[[1-(phenylsulfonyl)-3-pyrrolidinyl]amino]methyl]-phenoxy]-acetic Acid, 1,1-dimethylethyl Ester The sub-title compound was prepared by the method of Example 36 part (c) using the product from part (b).

$^1$H NMR (CDCl$_3$) δ 7.83 (2H, dt), 7.60-7.49 (3H, m), 7.15 (1H, dd), 7.11 (1H, d), 6.63 (1H, d), 4.51 (2H, s), 3.68 (2H, s), 3.46 (1H, dd), 3.39-3.19 (3H, m), 3.06 (1H, dd), 2.03-1.93 (1H, m), 1.72-1.62 (1H, m), 1.47 (9H, s).

d) [4-chloro-2-[[[1-(phenylsulfonyl)-3-pyrrolidinyl]amino]methyl]-phenoxy]-acetic Acid The title compound was prepared by the method of Example 36 part (d) using the product from part (c).

$^1$H NMR (DMSO-d6) δ 7.80 (2H, m), 7.72-7.58 (3H, m), 7.39 (1H, d), 7.34 (1H, dd), 7.05 (1H, d), 4.66 (2H, s), 3.96 (2H, s), 3.59-3.28 (3H, m), 3.25-3.12 (2H, m), 2.09 (1H, m), 1.88 (1H, m).

MS: APCI (−ve): 423 (M−1).

EXAMPLE 38

[4-chloro-2-[4-(phenylsulfonyl)-1-piperazinyl]phenoxy]-acetic Acid

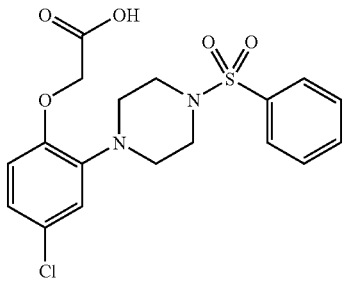 [SMILES: O=C(O)COc1ccc(Cl)cc1N1CCN(S(=O)(=O)c2ccccc2)CC1]

a) 4-chloro-2-(1-piperazinyl)-phenol 1-(5-chloro-2-methoxyphenyl)-piperazine hydrochloride (8 g) was heated in a solution of 48% aqueous HBr (200 ml) and the mixture was heated at reflux for 99 hours. The reaction mixture was concentrated in vacuo, the sub-title compound was used directly without any further purification.

MS: APCI (+ve): 213 (M+1).

b) 4-[5-chloro-2-(2-ethoxy-2-oxoethoxy)phenyl]-1-piperazinecarboxylic Acid, 1,1-dimethylethyl Ester The crude material from part a) was carefully dissolved in aqueous sodiumhydrogen is carbonate solution (200 ml), dioxan (80 ml) was added followed by BOC anhydride (10 g). The reaction was stirred for 18 hours, then extracted with ethyl acetate. The organic layer was washed (water), dried (MgSO$_4$) then concentrted in vacuo. The residue was dissolved in DMF (80 ml) and potassium carbonate was added (10 g), followed by ethyl bromoacetate (1.3 ml). After 2 hours the mixture was partitioned between ethyl acetate/water, the organics separated, dried (MgSO$_4$) and concentrated in vacuo. The residue was purified by chromatography (silica, (15-20% EtOAc/isohexane as elent)), to give the sub-title compound (6.3 g).

MS: APCI (+ve): 399/401 (M+1).

c) [4-chloro-2-(1-piperazinyl)phenoxy]-acetic Acid, Ethyl Ester Hydrochloride Salt The product of part c) (6.3 g), 4M HCl in dioxan (15 ml) and ethanol (30 ml) were stirred at room temperature for 16 hours, then the solid was filtered and washed with ether to give the sub-title compound (5.8 g).

MS: APCI (+ve): 299/301 (M+1).

d) [4-chloro-2-[4-(phenylsulfonyl)-1-piperazinyl]phenoxy]-acetic Acid

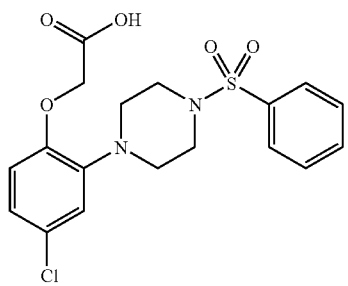 [SMILES: O=C(O)COc1ccc(Cl)cc1N1CCN(S(=O)(=O)c2ccccc2)CC1]

To a mixture of the product from step c) (0.34 g) and benzenesulfonyl chloride (0.11 ml) in THF (3 ml) was added triethylamine (0.42 ml) dropwise. After 5 min, further THF (3 ml) was added and the reaction stirred for 16 h. It was poured into 2M HCl and extracted with ethyl acetate. The organic layer was separated and washed with sat aqueous sodium bicarbonate solution, brine, dried ($Na_2SO_4$) and the solvent removed in vacuo. The residue was stirred in THF (2 ml) and 4M NaOH (4 ml) for 16 h. After acidification to pH 3, the aqueous layer was extracted with ethyl acetate. The organic layer was separated and the solvent removed in vacuo. Purification by RPHPLC (symmetry column) gave the title product as a white foam (0.12 g).

$^1$H NMR (DMSO-d6) δ 7.72 (5H, m), 6.91 (1H, dd), 6.83 (1H, d), 6.73 (1H, d), 4.39 (2H, s), 3.11 (4H, m), 3.00 (4H, m).

MS: APCI (−ve): 408 (M−1).

EXAMPLE 39

[4-chloro-2-[4-[(phenylmethyl)sulfonyl]-1-piperazinyl]phenoxy]-acetic Acid

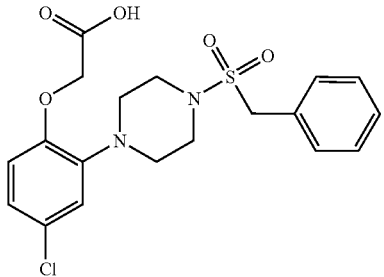 [SMILES: O=C(O)COc1ccc(Cl)cc1N1CCN(S(=O)(=O)Cc2ccccc2)CC1]

Prepared from the product from Example 38 step c) and benzenemethanesulfonyl chloride according to the procedure described in Example 38 step d) to give the sub-title compound as a white solid.

$^1$H NMR (DMSO-d6) δ 7.45-7.34 (5H, m), 6.90 (1H, dd), 6.79 (1H, d), 6.70 (1H, d), 4.46 (2H, s), 4.23 (2H, s), 3.26 (4H, m), 3.07 (4H, m).

MS: APCI (−ve): 423 (M−1).

EXAMPLE 40

[4-chloro-2-[4-(phenylacetyl)-1-piperazinyl]phenoxy]-acetic Acid

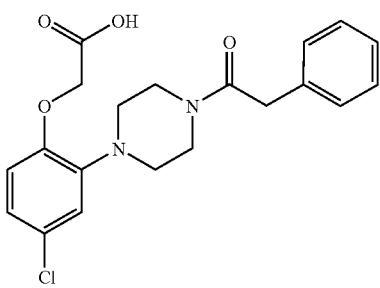 [SMILES: O=C(O)COc1ccc(Cl)cc1N1CCN(C(=O)Cc2ccccc2)CC1]

Prepared from the product from example 38 step c) and benzeneacetyl chloride by the method of Example 38 step d) to give the title compound as a white solid.

$^1$H NMR (DMSO-d6) δ 7.31 (2H, t), 7.25 (2H, d), 7.22 (1H, t), 6.88 (1H, dd), 6.74 (1H, d), 6.68 (1H, d), 4.19 (2H, s), 4.19 (2H, s), 3.60 (4H, t), 2.96 (4H, s). MS: APCI (−ve): 387 (M−1).

EXAMPLE 41

[2-[(4-benzoyl-1-piperazinyl)methyl]-4-(trifluoromethyl)phenoxy]-acetic Acid

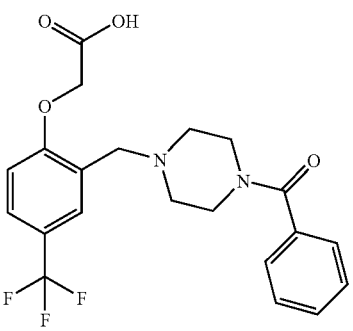 [SMILES: O=C(O)COc1ccc(C(F)(F)F)cc1CN1CCN(C(=O)c2ccccc2)CC1]

The title compound was prepared by the method of Example 32 using the product of Example 1 part e).

$^1$H NMR (DMSO-d6) δ 7.89 (1H, d), 7.63 (1H, dd), 7.47-7.37 (5H, m), 7.17 (1H, d), 4.75 (2H, s), 3.79 (2H, s), 3.7-3.3 (5H, m), 2.7-2.56 (4H, m).

MS: APCI (−ve): 421 (M−H).

EXAMPLE 42

[2-[[4-(2-thienylacetyl)-1-piperazinyl]methyl]-4-(trifluoromethyl)phenoxy]-acetic Acid

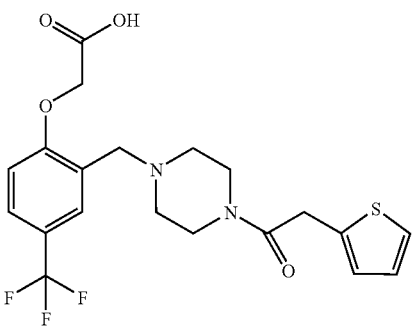 [SMILES: O=C(O)COc1ccc(C(F)(F)F)cc1CN1CCN(C(=O)Cc2cccs2)CC1]

The title compound was prepared by the method of Example 29 using the product of Example 1 part e).
MS: APCI (−ve): 441 (M−H).

EXAMPLE 43

[4-Chloro-2-[[4-[[(4-fluorophenyl)methyl]sulfonyl]-1-piperazinyl]methyl]phenoxy]acetic Acid

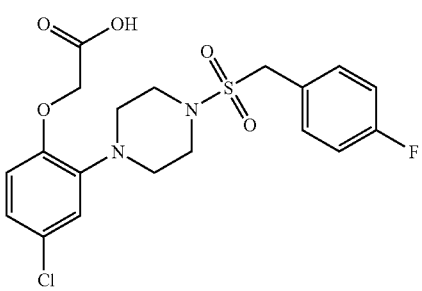 [SMILES: O=C(O)COc1ccc(Cl)cc1N1CCN(S(=O)(=O)Cc2ccc(F)cc2)CC1]

Prepared by the method of example 30, using the product of example 13 part (b) and 4-fluorobenzenemethanesulfonyl chloride to give the title compound.
MS: APCI (+ve): 457 (M+1).
$^1$H NMR (DMSO-d6) δ 7.46 (2H, m), 7.35 (1H, d), 7.30 (1H, m), 7.23 (2H, m), 7.01 (1H, d), 4.67 (2H, s), 4.45 (2H, s), 3.66 (2H, s), 3.19 (4H, m), 2.56 (4H, m).

EXAMPLE 44

[4-Chloro-2-[[4-[[(4-methylphenyl)methyl]sulfonyl]-1-piperazinyl]methyl]phenoxy]acetic Acid

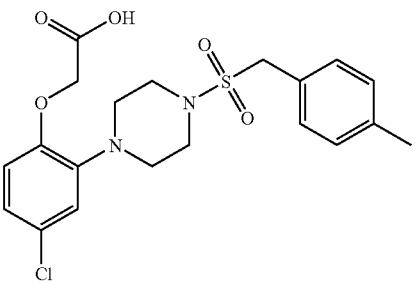 [SMILES: Cc1ccc(CS(=O)(=O)N2CCN(c3cc(Cl)ccc3OCC(=O)O)CC2)cc1]

Prepared by the method of example 30, using the product of example 13 part (b) and 4-methylbenzenemethanesulfonyl chloride to give the title compound.
MS: APCI (+ve): 453 (M+1).
$^1$H NMR (DMSO-d6) δ 7.34 (1H, m), 7.29 (3H, m), 7.18 (2H, m), 7.00 (1H, d), 4.67 (2H, s), 4.37 (2H, s), 3.65 (2H, s), 3.21-3.13 (4H, m), 2.58-2.50 (4H, m), 2.30 (3H, s).

EXAMPLE 45

[4-Chloro-2-[[4-[[(3-methylphenyl)methyl]sulfonyl]-1-piperazinyl]methyl]phenoxy]acetic Acid

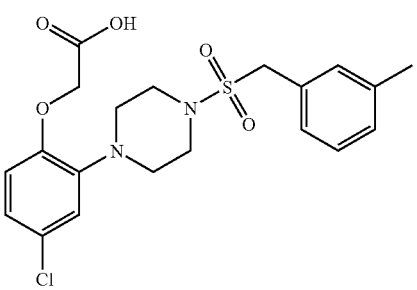 [SMILES: Cc1cccc(CS(=O)(=O)N2CCN(c3cc(Cl)ccc3OCC(=O)O)CC2)c1]

The product from example 13 part (b) (350 mg) was dissolved in THF (20 ml) and treated with triethylamine (430 μl) followed by 3-methylbenzenemethanesulfonyl chloride (190 mg). The reaction mixture was stirred for 5 h, treated with 1M NaOH (2 ml) and stirred for 20 h. Acetic acid (5 ml) was added, the mixture evaporated in vacuo, and the residue dissolved in DMSO and purified by RPHPLC to give the title compound (80 mg)
MS: APCI (−ve): 451 (M−1).
$^1$H NMR (DMSO-d6) δ 7.35 (1H, d), 7.28 (2H, m), 7.19 (3H, m), 7.00 (1H, d), 4.67 (2H, s), 4.38 (2H, s), 3.65 (2H, s), 3.22-3.15 (4H, m), 2.58-2.52 (4H, m), 2.32 (3H, s).

EXAMPLE 46

[4-Chloro-2-[[4-[(2-pyridinylmethyl)sulfonyl]-1-piperazinyl]methyl]phenoxy]acetic Acid

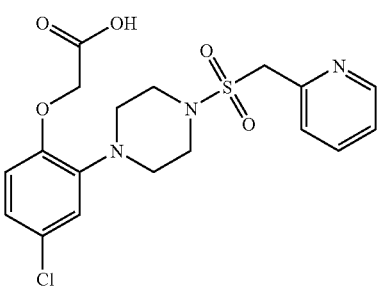 [SMILES: O=C(O)COc1ccc(Cl)cc1N1CCN(S(=O)(=O)Cc2ccccn2)CC1]

Prepared by the method of example 45, using the product of example 13 part (b) and 2-pyridinemethanesulfonyl chloride to give the title compound.
MS: APCI (−ve): 438 (M−1).
$^1$H NMR (DMSO-d6) δ 8.60 (1H, d), 7.89 (1H, t), 7.55 (1H, d), 7.43 (3H, m), 7.08 (1H, d), 4.59 (2H, s), 4.49 (2H, s), 3.42-3.33 (4H, m), 3.02-2.91 (4H, m).

EXAMPLE 47

[4-Chloro-2-[[4-[(3-pyridinylmethyl)sulfonyl]-1-piperazinyl]methyl]phenoxy]acetic Acid

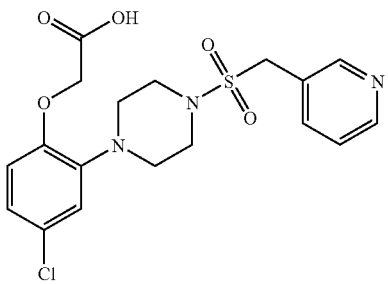 [SMILES: O=C(O)COc1ccc(Cl)cc1N1CCN(S(=O)(=O)Cc2cccnc2)CC1]

Prepared by the method of example 45, using the product of example 13 part (b) and 3-pyridinemethanesulfonyl chloride to give the title compound.

MS: APCI (−ve): 438 (M−1).

$^1$H NMR (DMSO-d6) δ 8.56 (2H, m), 7.90 (1H, d), 7.49 (3H, m), 7.21 (1H, d), 4.59 (2H, s), 4.57 (2H, s), 3.51-3.44 (4H, m), 3.17-3.10 (4H, m).

EXAMPLE 48

[4-Chloro-2-[[4-[(4-methylphenyl)acetyl]-1-piperazinyl]methyl]phenoxy]-1 acetic acid

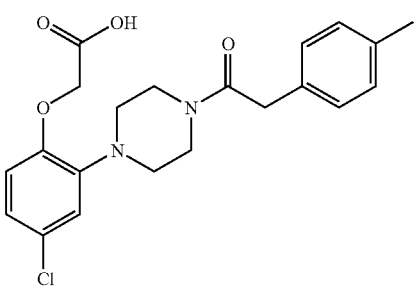 [SMILES: Cc1ccc(CC(=O)N2CCN(c3cc(Cl)ccc3OCC(=O)O)CC2)cc1]

The product from example 13 part (b) (200 mg) and 4-methylbenzeneacetic acid (63 mg) were dissolved in DMF (3 ml), Hunigs base (0.3 ml) added, followed by EDCI (100 mg). The reaction mixture was stirred for 20 h, diluted with MeOH (3 ml), treated with 1M NaOH (2 ml) and stirred for 20 h. Acetic acid (5 ml) was added, the mixture evaporated in vacuo, and the residue dissolved in DMSO and purified by RPHPLC to give the title compound (120 mg).

MS: APCI (−ve): 415 (M−1).

$^1$H NMR (DMSO-d6) δ 7.31 (1H, d), 7.23 (1H, dd), 7.09 (5H, m), 6.89 (1H, d), 4.38 (2H, s), 3.64 (2H, s), 3.60 (2H, s), 3.59-3.43 (4H, m), 2.51-2.41 (4H, m).

EXAMPLE 49

[4-Chloro-2-[[4-[(4-fluorophenyl)acetyl]-1-piperazinyl]methyl]phenoxy]acetic Acid

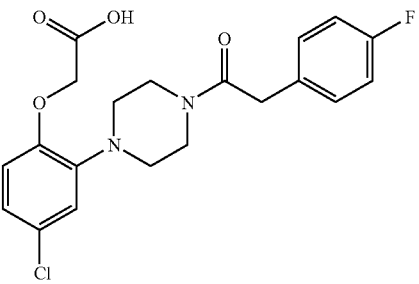 [SMILES: O=C(O)COc1ccc(Cl)cc1N1CCN(C(=O)Cc2ccc(F)cc2)CC1]

Prepared by the method of example 45, using the product of example 13 part (b) and 4-fluorobenzeneacetyl chloride to give the title compound.

MS: APCI (−ve): 419 (M−1).

$^1$H NMR (DMSO-d6) δ 7.39 (1H, d), 7.33 (1H, dd), 7.24 (2H, m), 7.12 (2H, m), 7.07 (1H, d), 4.63 (2H, s), 3.74 (2H, s), 3.72 (2H, s), 3.62-3.52 (4H, m), 2.63-2.58 (4H, m).

EXAMPLE 50

[4-Chloro-2-[[4-[(4-methoxyphenyl)acetyl]-1-piperazinyl]methyl]phenoxy]acetic Acid

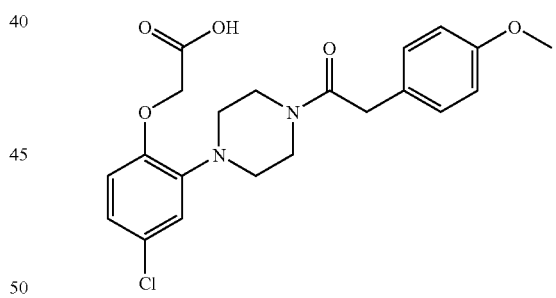

The product from example 13 part (b) (150 mg) and 4-methoxybenzeneacetic acid (60 mg) were dissolved in THF (10 ml), Hunigs base (0.23 ml) added, followed by Pybrop (130 mg). The reaction mixture was stirred for 2 h, treated with 1M NaOH (2 ml) and stirred for 20 h. Concentrated HCl (0.1 ml) added, the mixture evaporated in vacuo, and the residue dissolved in DMSO and purified by RPHPLC to give the title compound (110 mg).

MS: APCI (−ve): 431 (M−1).

$^1$H NMR (DMSO-d6) δ 7.29 (d, 1H), 7.19 (dd, 1H), 7.12 (d, 2H), 6.85 (d, 2H), 6.83 (d, 1H), 4.32 (s, 2H), 3.72 (s, 3H), 3.61 (s, 2H), 3.54 (s, 2H), 3.52-3.46 (m, 4H), 2.43-2.35 (m, 4H).

EXAMPLE 51

[4-Chloro-2-[[4-(3-pyridinylacetyl)-1-piperazinyl]methyl]phenoxy]acetic Acid

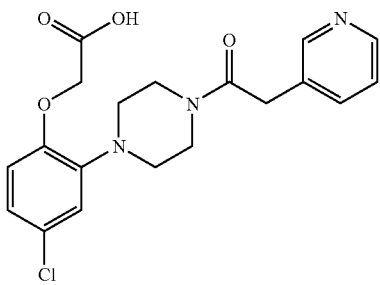

Prepared by the method of example 50, using the product of example 13 part (b) and 3-pyridineacetic acid to give the title compound.
MS: APCI (−ve): 431 (M−1).
$^1$H NMR (DMSO-d6) δ 7.29 (d, 1H), 7.19 (dd, 1H), 7.12 (d, 2H), 6.85 (d, 2H), 6.83 (d, 1H), 4.32 (s, 2H), 3.72 (s, 3H), 3.61 (s, 2H), 3.54 (s, 2H), 3.52-3.46 (m, 4H), 2.43-2.35 (m, 4H).

EXAMPLE 52

[4-Chloro-2-[[4-[(4-cyanophenyl)acetyl]-1-piperazinyl]methyl]phenoxy]acetic Acid

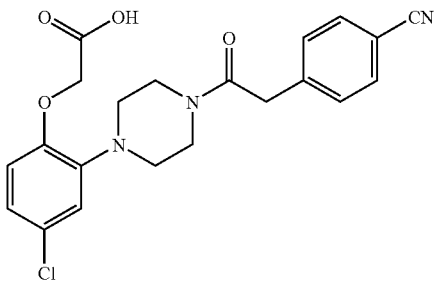 [SMILES: N#Cc1ccc(CC(=O)N2CCN(c3cc(Cl)ccc3OCC(=O)O)CC2)cc1]

Prepared by the method of example 50, using the product of example 13 part (b) and 4-cyanobenzeneacetic acid to give the title compound,
MS: APCI (−ve): 426 (M−1).
$^1$H NMR (DMSO-d6) δ 7.75 (d, 2H), 7.41 (d, 2H), 7.30 (d, 1H), 7.18 (dd, 1H), 6.82 (d, 1H), 4.31 (s, 2H), 3.82 (s, 2H), 3.57-3.45 (m, 4H), 3.55 (s, 2H), 2.45-2.38 (m, 4H).

EXAMPLE 53

[4-Chloro-2-[[2-methyl-4-(phenylsulfonyl)-1-piperazinyl]methyl]phenoxy]acetic Acid

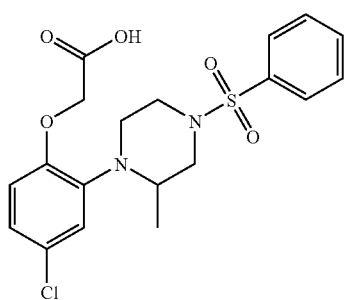 [SMILES: CC1CN(S(=O)(=O)c2ccccc2)CCN1c1cc(Cl)ccc1OCC(=O)O]

a) 4-[[5-Chloro-2-[2-(1,1-dimethylethoxy)-2-oxoethoxy]phenyl]methyl]-3-methyl-1-piperazinecarboxylic Acid, Phenyl Ester 3-Methyl-1-piperazinecarboxylic acid, phenylmethyl ester (380 mg), the product from example 13 part (a) (400 mg) and MgSO$_4$ were stirred in THF (30 ml) for 20 h. Sodium triacetoxy borohydride (510 mg) was added and stirred for 2 h. The mixture was quenched with water, extracted with EtOAc, washed with water and brine, dried (MgSO$_4$), filtered and evaporated in vacuo. The residue was purified by chromatography on silica with 20% EtOAc/isohexane as eluent to yield the sub-title compound (500 mg).
MS: APCI (+ve): 490 (M+1).
$^1$H NMR (DMSO-d6) δ 7.34 (m, 6H), 7.23 (dd, 1H), 6.88 (d, 1H), 5.08 (dd, 2H), 4.68 (s, 2H), 3.80 (m, 1H), 3.66 (m, 1H), 3.34 (m, 2H), 3.21-3.08 (m, 1H), 3.05-2.81 (m, 1H), 2.65 (m, 1H), 2.46 (m, 1H), 2.14 (m, 1H), 1.41 (s, 9H), 1.03 (d, 3H).

b) [4-Chloro-2-[(2-methyl-1-piperazinyl)methyl]phenoxy]acetic Acid, Hydrochloride The product from part (a) (500 mg) was dissolved in DCM (10 ml), TFA (5 ml) added and stirred for 20 h, then evaporated in vacuo. Concentrated HCl (20 ml) was added and heated at 80° C. for 20 h. The mixture was evaporated in vacuo and azeotoped with toluene in vacuo to yield the sub-title compound (330 mg).
MS: APCI (+ve): 299 (M+1).
$^1$H NMR (DMSO-d6) δ 7.66 (d, 1H), 7.45 (dd, 1H), 7.10 (d, 1H), 4.82 (s, 2H), 4.63-4.40 (m, 2H), 4.29-3.96 (m, 1H), 3.77-3.11 (m, 4H), 3.46 (s, 2H), 1.46 (d, 2H).

c) [4-Chloro-2-[[2-methyl-4-(phenylsulfonyl)-1-piperazinyl]methyl]phenoxy]acetic Acid Prepared by the method of example 30, using the product of part (b) and benzenesulfonyl chloride to give the title compound.
MS: APCI (−ve): 437 (M−1).
$^1$H NMR (DMSO-d6) δ 7.70 (m, 5H), 7.28 (m, 1H), 7.24 (m, 1H), 6.96 (d, 1H), 4.63 (dd, 2H), 3.91 (d, 1H), 3.48-3.18 (m, 3H), 2.83-2.27 (m, 4H), 1.10 (d, 3H).

EXAMPLE 54

[4-Chloro-2-[[2-methyl-4-[(phenylmethyl)sulfonyl]-1-piperazinyl]methyl]phenoxy]acetic Acid

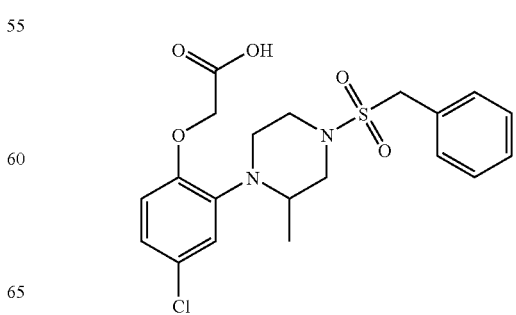

Prepared by the method of example 30, using the product of example 53 part (b) and benzenemethanesulfonyl chloride to give the title compound.

MS: APCI (−ve): 451 (M−1).

$^1$H NMR (DMSO-d6) δ 7.38 (m, 5H), 4.38 (s, 2H), 3.33 (m, 3H), 2.83 (d, 1H), 2.57 (m, 2H), 2.27 (m, 1H), 0.92 (d, 3H).

b) [4-Chloro-2-[[(2R)-2-methyl-4-(phenylsulfonyl)-1-piperazinyl]methyl]phenoxy]acetic acid

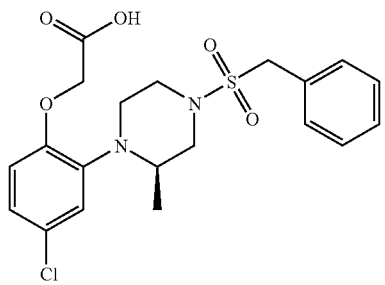 [SMILES: C[C@@H]1CN(S(=O)(=O)Cc2ccccc2)CCN1c1cc(Cl)ccc1OCC(=O)O]

The product from part (a) (200 mg), the product from example 13 part (a) (210 mg) and MgSO$_4$ were stirred in THF (30 ml) for 20 h. Sodium triacetoxy borohydride (340 mg) was added and stirred for 2 h. The mixture was quenched with water, extracted with EtOAc, washed with water and brine, dried (MgSO$_4$), filtered and evaporated in vacuo. The residue was dissolved in MeOH (10 ml), 1M NaOH (5 ml) added and stirred for 3 h. The mixture was treated with AcOH (5 ml), DMSO (3 ml) added, evaporated to 3 ml and purified by RPHPLC to give the title compound (290 mg).

MS: APCI (+ve): 453 (M+1).

$^1$H NMR (DMSO-d6) δ 7.38 (m, 6H), 7.28 (dd, 1H), 7.00 (d, 1H), 4.63 (dd, 2H), 4.43 (s, 2H), 3.99 (d, 1H), 3.48 (d, 1H), 3.33 (m, 1H), 3.03 (m, 1H), 2.88-2.67 (m, 2H), 2.46-2.24 (m, 1H), 1.11 (d, 3H).

EXAMPLE 56

[4-Chloro-2-[[3-methyl-4-[(phenylmethyl)sulfonyl]-1-piperazinyl]methyl]phenoxy]acetic Acid

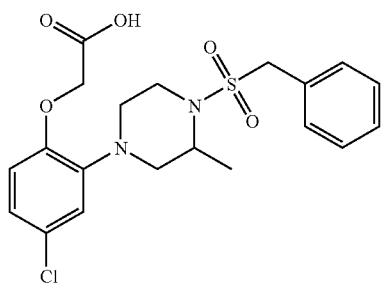 [SMILES: CC1CN(c2cc(Cl)ccc2OCC(=O)O)CCN1S(=O)(=O)Cc1ccccc1]

a) [4-Chloro-2-[(3-methyl-1-piperazinyl)methyl]phenoxy]acetic Acid, 1,1-dimethylethyl Ester 2-Methyl-1-piperazine (600 mg), the product from example 13 part (a) (810 mg) and MgSO$_4$ were stirred in THF (50 ml) for 20 h. Sodium triacetoxy borohydride (2×850 mg) was added and stirred for 2 h. The mixture was quenched with water, extracted with EtOAc, washed with water and brine, dried (MgSO$_4$), filtered and evaporated in vacuo. The residue was purified by chromatography on silica with 20% EtOAc/isohexane as eluent to yield the sub-title compound (850 mg).

MS: APCI (+ve): 355 (M+1).

$^1$H NMR (DMSO-d6) δ 7.35 (m, 1H), 7.22 (m, 1H), 6.87 (m, 1H), 4.68 (s, 2H), 3.81 (m, 1H).

b) [4-Chloro-2-[[3-methyl-4-[(phenylmethyl)sulfonyl)-1-piperazinyl]methyl]phenoxy]acetic Acid Prepared by the method of example 30, using the product from part (a) and benzenemethanesulfonyl chloride to give the title compound.

MS: APCI (−ve): 451 (M−1).

$^1$H NMR (DMSO-d6) δ 7.37 (m, 6H), 7.25 (dd, 1H), 6.93 (d, 1H), 4.67 (s, 2H), 4.39 (dd, 2H), 3.82-3.73 (m, 1H), 3.51 (s, 2H), 3.23-3.09 (m, 1H), 2.74-2.53 (m, 2H), 2.14-1.96 (m, 3H), 1.24 (d, 3H).

EXAMPLE 57

[4-Chloro-2-[[3-methyl-4-(phenylsulfonyl)-1-piperazinyl]methyl]phenoxy]acetic Acid

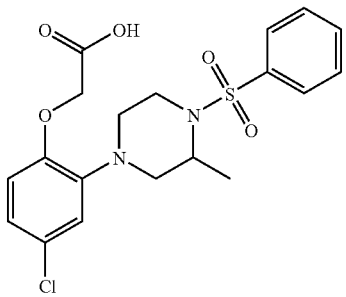 [SMILES: CC1CN(c2cc(Cl)ccc2OCC(=O)O)CCN1S(=O)(=O)c1ccccc1]

Prepared by the method of example 30, using the product from example 56 part (a) and is benzenesulfonyl chloride to give the title compound.

MS: APCI (−ve): 437 (M−1).

$^1$H NMR (DMSO-d6) δ 7.79 (d, 2H), 7.63 (m, 3H), 7.30 (d, 1H), 7.23 (m, 1H), 6.90 (d 1H), 4.66 (s, 2H), 3.98 (m, 1H), 3.56 (m, 1H), 3.44 (s, 2H), 3.18 (m, 1H), 2.72 (m, 1H), 2.56 (m, 1H), 2.03 (m, 1H), 1.94 (m, 1H), 1.09 (d, 3H).

EXAMPLE 58

[4-Chloro-2-[[3-methyl-4-(phenylacetyl)-1-piperazinyl]methyl]phenoxy]acetic Acid

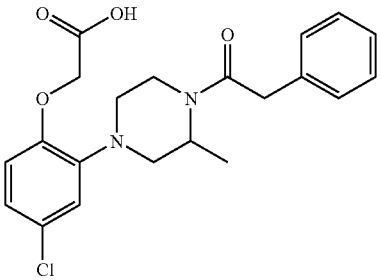 [SMILES: CC1CN(c2cc(Cl)ccc2OCC(=O)O)CCN1C(=O)Cc1ccccc1]

Prepared by the method of example 30, using the product from example 56 part (a) and benzeneacetyl chloride to give the title compound.

MS: APCI (+ve): 417 (M+1).

$^1$H NMR (DMSO-d6) δ 7.58-7.40 (m, 2H), 7.30 (m, 2H), 7.26-7.16 (m, 3H), 7.08 (m, 1H), 4.79 (s, 2H), 3.73 (s, 2H), 4.91-4.66 (m, 1H), 4.53-3.88 (m, 3H), 3.78-2.88 (m, 3H), 1.16 (d, 3H).

EXAMPLE 59

[4-Chloro-2-[[(3S)-3-methyl-4-(phenylsulfonyl)-1-piperazinyl]methyl]phenoxy]acetic Acid

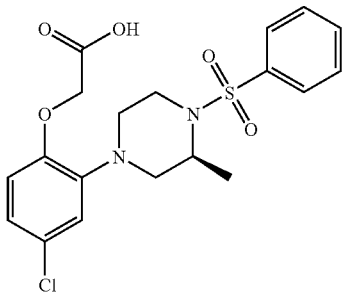 [SMILES: C[C@H]1CN(c2cc(Cl)ccc2OCC(=O)O)CCN1S(=O)(=O)c1ccccc1]

a) 3-Methyl-4-[(phenylmethyl)sulfonyl]-(3S)-1-piperazinecarboxylic Acid, 1,1-dimethylethyl Ester 3-Methyl-(3S)-1-piperazinecarboxylic acid, 1,1-dimethylethyl ester (1.0 g) was dissolved in DCM (30 ml) and treated with triethylamine (2.1 ml), followed by benzenesulfonyl chloride (0.77 ml). The reaction mixture was stirred for 20 h, quenched with water, extracted with DCM, dried (MgSO$_4$) and concentrated in vacuo. The residue was purified by chromatography on silica with 25% EtOAc/isohexane as eluent to give the sub-title compound (1.6 g)

MS: APCI (−ve): 341 (M−1).

$^1$H NMR (CDCl$_3$) δ 7.81 (m, 2H), 7.54 (m, 3H), 4.18-3.58 (m, 4H), 3.16-2.68 (m, 3H), 1.43 (s, 9H), 1.01 (d, 3H).

b) 2-Methyl-1-(phenylsulfonyl)-(2S)-piperazine, Trifluoroacetate Salt

The product from part (a) was dissolved in DCM (10 ml), treated with TFA (3 ml) and stirred for 3 h. Toluene (20 ml) was added and the mixture evaporated in vacuo to give the sub-title compound (1.7 g).

MS: APCI (−ve): 241 (M−1).

$^1$H NMR (CDCl$_3$) δ 7.81 (m, 2H), 7.64 (m, 1H), 7.56 (m, 2H), 4.34 (m, 1H), 3.86 (m, 1H), 3.46 (m, 1H), 3.35 (m, 1H), 3.15 (m, 2H), 2.99 (m, 1H), 1.22 (d, 3H)

c) [4-Chloro-2-[[(3S)-3-methyl-4-(phenylsulfonyl)-1-piperazinyl]-methyl]phenoxy]-acetic Acid Prepared by the method of example 55 part (b), using the product from part (b) (500 mg) and the product from example 13 part (a) (490 mg) to give the title compound (490 mg).

MS: APCI (−ve): 439 (M−1).

$^1$H NMR (DMSO-d6) δ 7.79 (d, 2H), 7.64 (m, 3H), 7.30 (d, 1H), 7.22 (dd, 1H), 6.90 (d, 1H), 4.65 (s, 2H), 3.98 (m, 1H), 3.56 (m, 1H), 3.43 (s, 2H), 3.18 (m, 1H), 2.72 (m, 1H), 2.55 (m, 1H), 2.03 (m, 1H), 1.93 (m, 1H), 1.09 (d, 1H).

EXAMPLE 60

[4-Chloro-2-[[(3R)-3-methyl-4-(phenylsulfonyl)-1-piperazinyl]methyl]phenoxy]acetic Acid

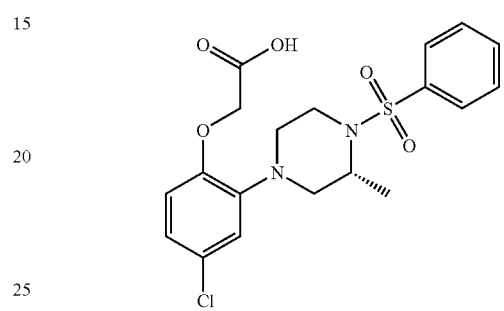

Prepared by the method of example 59 parts (a) to (c) using 3-methyl-(3R)-1-piperazinecarboxylic acid, 1,1-dimethylethyl ester to give the title compound.

MS: APCI (−ve): 439 (M−1).

$^1$H NMR (DMSO-d6) δ 7.79 (d, 2H), 7.63 (m, 3H), 7.29 (d, 1H), 7.22 (dd, 1H), 6.89 (d, 1H), 4.63 (s, 2H), 3.98 (m, 1H), 3.56 (m, 1H), 3.43 (s, 2H), 3.18 (m, 1H), 2.72 (m, 1H), 2.55 (m, 1H), 2.03 (m, 1H), 1.93 (m, 1H), 1.09 (d, 3H).

EXAMPLE 61

[4-Chloro-2-[[(3R)-3-methyl-4-[(phenylmethyl)sulfonyl]-1-piperazinyl]methyl]phenoxy]acetic Acid

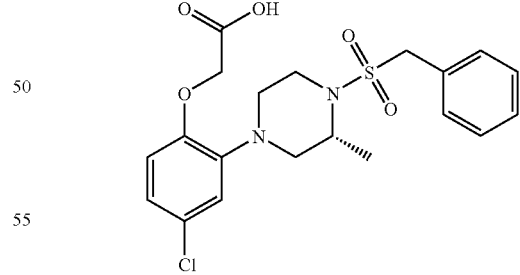

Prepared by the method of example 59 parts (a) to (c) using 3-methyl-(3R)-1-piperazinecarboxylic acid, 1,1-dimethylethyl ester and benzenemethanesulfonyl chloride to give the title compound.

MS: APCI (−ve): 451 (M−1).

$^1$H NMR (DMSO-d6) δ 7.37 (m, 6H), 7.25 (dd, 1H), 6.94 (d, 1H), 4.69 (s, 2H), 4.39 (dd, 2H), 3.84-3.08 (m, 3H), 3.51 (s, 2H), 2.75-2.51 (m, 2H), 2.16-1.93 (m, 2H), 1.24 (d, 3H).

EXAMPLE 62

[4-Chloro-2-[[(3S)-3-methyl-4-[(phenylmethyl)sulfonyl]-1-piperazinyl]methyl]phenoxy]acetic Acid

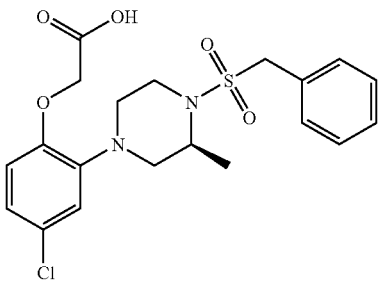 [SMILES: C[C@H]1CN(c2cc(Cl)ccc2OCC(=O)O)CCN1S(=O)(=O)Cc1ccccc1]

a) 2-Methyl-4-(1,1-dimethylethyl)-(2S)-1,4-piperazinedicarboxylic Acid, 1-(9H-fluoren-9-ylmethyl) ester FMOC chloride (500 mg) was added dropwise over 5 min to a vigorously stirred is mixture of 3-methyl-(3S)-1-piperazinecarboxylic acid, 1,1-dimethylethyl ester (350 mg) and NaHCO$_3$ (840 mg) in DCM (10 ml) and water (10 ml). After 2 h the layers were separated, the organics dried (MgSO$_4$), filtered and evaporated in vacuo. The residue was purified by chromatography on silica with 20% EtOAc/isohexane as eluent to give the sub-title compound (540 mg).

MS: APCI (+ve): 423 (M+1).

$^1$H NMR (CDCl$_3$) δ 7.77 (d, 2H), 7.56 (d, 2H), 7.40 (t, 2H), 7.32 (t, 2H), 4.48 (m, 2H), 4.31-3.70 (m, 4H), 4.24 (t, 1H), 3.05 (m, 1H), 3.02-2.65 (m, 2H), 1.47 (s, 9H), 1.09 (d, 3H).

b) 2-Methyl-(2S)-1-piperazinecarboxylic Acid, 9H-fluoren-9-ylmethyl Ester, Trifluoroacetate Salt The product from part (a) was dissolved in DCM (5 ml), treated with TFA (2 ml) and stirred for 3 h. Toluene (20 ml) was added and the mixture evaporated in vacuo to give the sub-title compound (520 mg).

MS: APCI (+ve): 423 (M+1).

$^1$H NMR (DMSO-d6) δ 9.30-9.14 (m, 1H), 8.80-8.60 (m, 1H), 7.90 (d, 2H), 7.64 (m, 2H), 7.43 (t, 2H), 7.35 (t, 2H), 4.46 (d, 2H), 4.29 (t, 1H), 4.25-4.15 (m, 1H), 3.87-3.80 (m, 1H), 3.23-2.97 (m, 4H), 2.90-2.78 (m, 1H), 1.09 (d, 3H).

c) 4-[[2-(Carboxymethoxy)-5-chlorophenyl]methyl]-2-methyl-(2S)-1-piperazinecarboxylic Acid, 1-(9H-fluoren-9-ylmethyl)ester The product from part (b) (500 mg), the product from example 13 part (a) (350 mg) and MgSO$_4$ were stirred in THF (50 ml) for 20 h. Sodium triacetoxy borohydride (480 mg) was added and stirred for 2 h. The mixture was quenched with water, extracted with EtOAc, washed with water and brine, dried (MgSO$_4$), filtered and evaporated in vacuo. The residue was purified by chromatography on silica with 20% EtOAc/isohexane as eluent to yield the sub-title compound (510 mg).

MS: APCI (+ve): 578 (M+1).

$^1$H NMR (CDCl$_3$) δ 7.76 (d, 2H), 7.57 (d, 2H), 7.44 (d, 1H), 7.39 (t, 2H), 7.31 (t, 2H), 7.15 (dd, 1H), 6.65 (d, 1H), 4.50 (s, 2H), 4.43 (m, 2H), 4.28-4.17 (m, 1H), 4.24 (t, 1H), 3.90-3.81 (m, 1H), 3.56 (s, 2H), 3.19 (m, 1H), 2.80 (d, 1H), 2.65 (d, 1H), 2.23 (dd, 1H), 2.10 (td, 1H), 1.48 (s, 9H), 1.27 (d, 1H).

d) [4-Chloro-2-[[(3S)-3-methyl-1-piperazinyl]methyl]-phenoxy]acetic Acid

The product from part (c) (500 mg) was dissolved in DCM (5 ml), pyrrolidine (1.0 ml) added and stirred for 20 h. Toluene added and evaporated in vacuo. Purified by chromatography on silica with 5-10% (0.1% NH$_3$-MeOH)/DCM as eluent to give the sub-title compound (300 mg).

MS: APCI (+ve): 355 (M+1).

$^1$H NMR (CDCl$_3$) δ 7.36 (d, 1H), 7.15 (dd, 1H), 6.65 (d, 1H), 4.50 (s, 2H), 3.59 (s, 2H), 3.11-2.94 (m, 3H), 2.84 (m, 2H), 2.29 (m, 1H), 1.99 (m, 1H), 1.47 (s, 9H), 1.17 (d, 3H).

e) [4-Chloro-2-[[(3S)-3-methyl-4-[(phenylmethyl)sulfonyl]-1-piperazinyl]methyl]phenoxy]acetic Acid Benzenemethanesulfonyl chloride (100 mg) was added dropwise over 5 min to a vigorously stirred mixture of the product from part d) (150 mg) and NaHCO$_3$ (110 mg) in DCM (10 ml) and water (10 ml). After 2 h the layers were separated, the organics dried (MgSO$_4$), filtered and evaporated in vacuo. The residue was purified by RVHPLC to give the title compound (140 mg).

MS: APCI (−ve): 451 (M−1).

$^1$H NMR (DMSO-d6) δ 7.43-7.32 (m, 6H), 7.23 (dd, 1H), 6.90 (d, 1H), 4.61 (s, 2H), 4.39 (dd, 2H), 3.77 (m, 1H), 3.50 (s, 2H), 3.30 (m, 1H), 3.14 (m, 1H), 2.71 (m, 1H), 2.56 (m, 1H), 2.10 (m, 1H), 2.00 (m, 1H), 1.24 (d, 3H).

EXAMPLE 63

[4-Chloro-2-[[(3R)-3-methyl-4-(phenylacetyl)-1-piperazinyl]methyl]phenoxy]acetic Acid

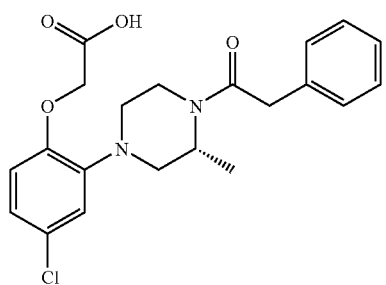 [SMILES: C[C@@H]1CN(c2cc(Cl)ccc2OCC(=O)O)CCN1C(=O)Cc1ccccc1]

Prepared by the method of example 59 parts (a) to (c) using 3-methyl-(3R)-1-piperazinecarboxylic acid, 1,1-dimethylethyl ester and benzeneacetyl chloride to give the title compound (130 mg).

MS: APCI (−ve): 415 (M−1).

$^1$H NMR (DMSO-d6) δ 7.35 (d, 1H), 7.30 (m, 2H), 7.21 (m, 4H), 6.87 (d, 1H), 4.54 (m, 1H), 4.51 (s, 2H), 4.20 (m, 1H), 3.80-2.62 (m, 3H), 3.68 (s, 2H), 3.50 (s, 2H), 2.07 (m, 1H), 1.94 (m, 1H), 1.17 (d, 3H).

EXAMPLE 64

[4-Chloro-2-[[(3S)-3-methyl-4-(phenylacetyl)-1-piperazinyl]-methyl]phenoxy]acetic Acid

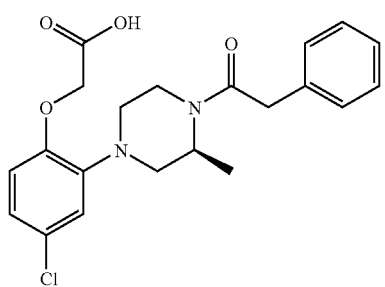

a) 3-Methyl-4-(phenylacetyl)-(3S)-1-piperazinecarboxylic Acid, 1,1-dimethylethyl Ester 3-Methyl-(3S)-1-piperazinecarboxylic acid, 1,1-dimethylethyl ester (250 mg), benzeneacetic acid (210 mg) and Hunigs base (450 □l) were dissolved in DMF (10 ml) and HATU (720 mg) added portionwise over 2 min. The reaction mixture was stirred for 3 h, diluted with EtOAc, washed with water and brine, dried (MgSO$_4$) and concentrated in vacuo. The residue was purified by chromatography on silica with 25% EtOAc/isohexane as eluent to give the sub-title compound (330 mg)

MS: APCI (+ve): 319 (M+1).

$^1$H NMR (CDCl$_3$) δ 7.27 (m, 5H), 4.87-4.38 (m, 1H), 4.18-3.49 (m, 3H), 3.74 (s, 2H), 3.26-2.49 (m, 4H), 1.44 (s, 9H), 1.11 (m, 3H).

b) 2-Methyl-1-(phenylacetyl)-(2S)-piperazine, Trifluoroacetate Salt

The product from part (a) was dissolved in DCM (10 ml), treated with TEA (3 ml) and stirred for 3 h. Toluene (20 ml) was added and the mixture evaporated in vacuo to give the sub-title compound (330 mg).

MS: APCI (+ve): 219 (M+1).

$^1$H NMR (CDCl$_3$) δ 7.28 (m, 5H), 5.27-4.20 (m, 3H), 4.86 (s, 2H), 3.57-2.45 (m, 4H), 1.30 (d, 3H).

c) [4-Chloro-2-[[(3S)-3-methyl-4-(phenylacetyl)-1-piperazinyl]methyl]phenoxy]acetic Acid Prepared by the method of example 55 part (b), using the product from part (b) (300 mg) and the product from example 13 part a) (300 mg) to give the title compound (400 mg).

MS: APCI (−ve): 415 (M−1).

$^1$H NMR (DMSO-d6) δ 7.37 (d, 1H), 7.30 (m, 2H), 7.23 (m, 4H), 6.92 (d, 1H), 4.65 (s, 2H), 4.57 (m, 1H), 4.21 (m, 1H), 3.79-2.64 (m, 3H), 3.68 (s, 2H), 3.52 (s, 2H), 2.09 (m, 1H), 1.95 (m, 1H), 1.17 (d, 3H).

EXAMPLE 65

[4-Chloro-2-[[(3S)-4-[(4-chlorophenyl)acetyl]-3-methyl-1-piperazinyl]methyl]phenoxy]acetic Acid

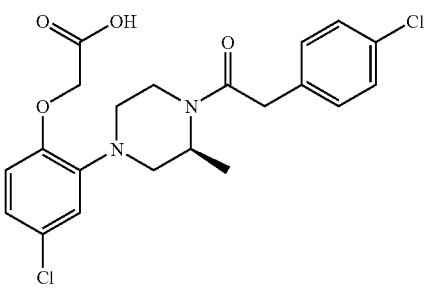 [SMILES: C[C@H]1CN(c2cc(Cl)ccc2OCC(=O)O)CCN1C(=O)Cc1ccc(Cl)cc1]

Prepared by the method of example 62 part (e) using the product from example 62 part (d) and 4-chlorobenzeneacetyl chloride to give the title compound.

MS: APCI (−ve): 449 (M−1).

$^1$H NMR (DMSO-d6) δ 7.40-7.32 (m, 3H), 7.28-7.19 (m, 3H), 6.93 (d, 1H), 4.65 (s, 2H), 4.54 (m, 1H), 4.20 (m, 1H), 3.69 (s, 2H), 3.53 (s, 2H), 3.24 (m, 1H), 2.84 (m, 1H), 2.69 (m, 1H), 2.12 (m, 1H), 1.98 (m, 1H), 1.19 (m, 3H).

EXAMPLE 66

[2-[(4-Benzoyl-3-methyl-1-piperazinyl)methyl]-4-chlorophenoxy]acetic Acid

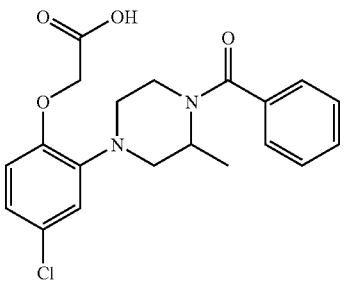 [SMILES: CC1CN(c2cc(Cl)ccc2OCC(=O)O)CCN1C(=O)c1ccccc1]

Prepared by the method of example 30, using the product from example 56 part (a) and benzoyl chloride to give the title compound.

MS: APCI (−ve): 401 (M−1).

$^1$H NMR (DMSO-d6) δ 7.44 (m, 3H), 7.36 (m, 3H), 7.22 (dd, 1H), 6.88 (d, 1H), 4.56 (s, 2H), 3.54 (s, 2H), 3.49-3.10 (m, 3H), 2.89-2.65 (m, 2H), 2.24-2.03 (m, 2H), 1.30 (d, 3H).

EXAMPLE 67

[4-chloro-2-[[2,5-dimethyl-4-(phenylacetyl)-1-piperazinyl]methyl]-phenoxy]-acetic Acid

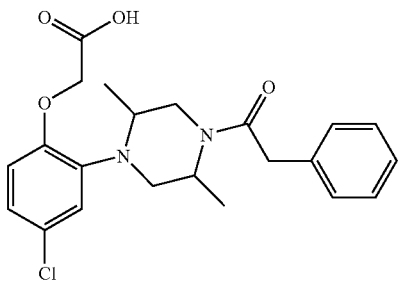 [SMILES: CC1CN(c2cc(Cl)ccc2OCC(=O)O)C(C)CN1C(=O)Cc1ccccc1]

a) 2,5-dimethyl-1-(phenylacetyl)-piperazine

Diisopropylethylamine (0.38 ml) was added to a solution of trans-2,5-dimethyl-piperazine (1.50 g), phenyl acetic acid (0.59 g) and HATU (1.55 g) in DMF (10 ml). The reaction mixture was stirred overnight at ambient temperature. The solution was diluted with water, then extracted with ethyl acetate. The organic extracts were dried (MgSO$_4$) then concentrated in vacuo to give the sub-title compound (1.8 g).

MS: APCI (+ve): 233 (M+1).

b) [4-chloro-2-[[2,5-dimethyl-4-(phenylacetyl)-1-piperazinyl]methyl]phenoxy]-acetic Acid, 1,1-dimethylethyl Ester The product from step a) (370 mg) was dissolved in THF (50 ml) and the product from example 13 part a) (430 mg) was added followed by MgSO$_4$ and the suspension was stirred for 3 h under nitrogen. Sodium triacetoxyborohydride (340 mg) was added and stirred overnight. The reaction mixture was diluted with water and extracted with EtOAc. The organic phase was dried (MgSO$_4$) then concentrated in vacuo.

The residue was purified by chromatography on silica with 50% diethyl ether/isohexane as eluent to give the sub-title compound (240 mg).

MS: APCI (+ve): 487 (M+1).

c) [4-chloro-2-[[2,5-dimethyl-4-(phenylacetyl)-1-piperazinyl]methyl]phenoxy]-acetic Acid The product from part b) (0.24 g), TFA (5 ml) and dichloromethane (10 ml) were stirred is for 16 h at ambient temperature. The solution was concentrated in vacuo and purified to reverse phase HPLC to give the title compound (40 mg).

MS: APCI (+ve): 431 (M+1).

$^1$H NMR (DMSO-d6) δ 7.39 (1H, s), 7.29-7.16 (6H, m), 6.90 (1H, d), 4.59 (2H, s), 4.37 (1H, s), 3.8 (1H, d), 3.73-3.49 (4H, dd), 3.24 (1H, d), 2.95 (1H, s), 2.7-2.26 (2H, dd), 1.15 (3H, d), 0.87 (3H, d).

EXAMPLE 68

[4-Chloro-2-[[4-(1-oxo-2-phenylpropyl)-1-piperazinyl]methyl]phenoxy]-acetic Acid

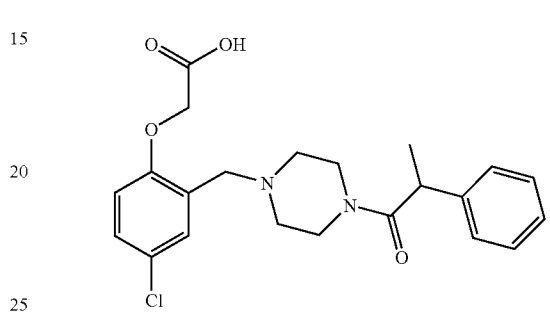

a) 4-(1-Methyl-2-oxo-2-phenylethyl)-1-piperazinecarboxylic acid, 1,1-dimethylethyl Ester To N-BOC-piperazine (0.373 g) in DMF (10 ml) was added HATU (1.14 g) followed by 2-phenylpropionic acid (0.30 ml) and the reaction stirred at RT for 16 h followed by 60° C. for 1 h. The reaction was cooled to RT, then diluted with diethyl ether, washed with water (×3), 2M HCl (×2), saturated aq. NaHCO$_3$ (aq) (×2), dried (Na$_2$SO$_4$) and concentrated in vacuo to give the sub-titled compound (0.25 g).

$^1$H NMR (CDCl$_3$) δ 7.49-7.22 (5H, m), 3.85 (1H, q), 3.82 (1H, m), 3.66-3.14 (6H, m), 2.70 (1H, m), 1.45 (3H, d), 1.42 (9H, s).

b) [4-Chloro-2-[[4-(1-oxo-2-phenylpropyl)-1-piperazinyl]methyl]phenoxy]-acetic Acid The product of example 68 part a) (250 mg) was dissolved in DCM (5 ml) and TFA (5 ml) and stirred for 1 h, and then the reaction mixture was concentrated in vacuo. The residue was dissolved in THF (5 ml), the product from example 13 part b (179 mg) and MgSO$_4$ (xs) added and the reaction stirred for 1 h. Sodium triacetoxy borohydride (0.62 g) was added and the reaction stirred for 16 h. The reaction was quenched with water and extracted with ethyl acetate. The organic layer was dried (MgSO$_4$) and concentrated in vacuo. It was purified by passage through SCX resin eluting with MeCN, MeOH followed by 7M NH$_3$ in MeOH. Treatment with TFA (10 ml) for 16 h and purification by RPHPLC to give the title compound as a white foam (0.103 g)

MS: APCI (+ve): 417 (M+1).

$^1$H NMR (DMSO-d$_6$) 7.34-7.19 (7H, m), 6.94 (1H, d), 4.47 (2H, s), 4.09 (1H, q), 3.57 (2H, s), 3.55 (4H, m), 3.29 (1H, m), 2.44 (2H, m), 2.09 (1H, m), 1.27 (3H, d).

EXAMPLE 69

[4-Chloro-2-[[(3S)-3-ethyl-4-(phenylsulfonyl)-1-piperazinyl]-methyl]-phenoxy]-acetic Acid

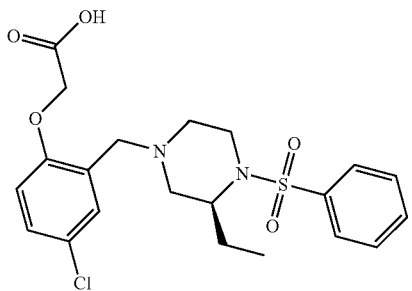 [SMILES: CC[C@H]1CN(Cc2cc(Cl)ccc2OCC(=O)O)CCN1S(=O)(=O)c1ccccc1]

a) (3S)-3-Ethyl-1-(phenylmethyl)-2,5-piperazinedione

To a solution of DCC (5.07 g) in DCM (140 mL) at 0° C. was added N—BOC-L-☐-aminobutyric acid (5 g) followed by ethyl JV-benzylglycinate (4.6 mL) dropwise. The resulting solution was stirred at 0° C. for 2 h and RT 1 h, filtered and the concentrated to give an oil. This was dissolved in DCM (100 mL) and TFA (100 ml) and stirred for 1 h. The solution was concentrated under reduced pressure. The residue was stirred in saturated aq NaHCO3 (125 ml) and EtOAc (125 ml) for 6 h. The organics were separated, dried (Na$_2$SO$_4$), and concentrated to give the sub title compound as a white solid. (5.68 g).

$^1$H NMR (CDCl$_3$) δ 7.37-7.31 (3H, m), 7.26 (2H, m), 6.80 (1H, s), 4.70 (1H, d), 4.50 (1H, d), 4.05 (1H, s), 3.87 (1H, d), 3.80 (1H, d), 1.93 (2H, m), 0.98 (3H, t).

b) (3S)-3-Ethyl-1-(phenylmethyl)-piperazine

To a solution of the product of example 69 part a) (5.68 g) in THF (30 ml) at 0° C. was added LAH (100 ml, 1.0M in THF) dropwise. The resulting solution was heated at reflux overnight. The reaction mixture was cooled to RT and quenched by cautious sequential addition of water (3.8 ml), 15% aq NaOH (3.8 ml), and water (11.4 ml). The precipitous solution was diluted with EtOAc and filtered through Celite. The residue was washed with EtOAc (3×100 ml) and the combined organics concentrated in vacuo. The crude product was dissolved in DCM, filtered through Celite and the solvent removed in vacuo to give the sub-titled product as a yellow oil (4.74 g).

$^1$H NMR (CDCl$_3$) δ 7.41-7.19 (5H, m), 3.53 (1H, d), 3.46 (1H, d), 2.99-2.61 (5H, m), 2.01 (1H, dt), 1.69 (1H, t), 1.35 (2H, dquintet), 0.90 (3H, t).

c) (2S)-2-Ethyl-4-(phenylmethyl)-1-piperazinecarboxylic acid, 1,1-dimethylethyl ester To a solution of the product from example 69 part b) (4.74 g) in DCM (150 ml) was added (BOC)$_2$O (5.52 g) and the reaction stirred at RT for 48 h. The reaction was concentrated under reduced pressure. The crude product was purified by chromatography (silica, (0-10% EtOAc/isohexane as eluent)), to give the sub-titled compound as a colourless oil (6.09 g).

$^1$H NMR (CDCl$_3$) δ 7.33-7.22 (5H, m), 3.89 (2H, m), 3.53 (1H, d), 3.38 (1H, d), 3.04 (1H, t), 2.71 (2H, dd), 2.02 (2H, ddd), 1.83 (1H, m), 1.64 (1H, m), 1.45 (9H, s), 0.80 (3H, t).

d) (2S)-2-Ethyl-1-piperazinecarboxylic acid, 1,1-dimethylethyl ester

A solution of the product from example 69 part c) (6.09 g) and 10% Pd/C (1.14 g) in EtOH (85 mL) was hydrogenated at 3.8 bar for 16 h. The reaction mixture was filtered through Celite and the filtrate concentrated in vacuo to give the sub-title compound as an oil (3.65 g).

$^1$H NMR (CDCl$_3$) δ 3.87 (2H, m), 2.87 (4H, m), 2.68 (1H, d), 1.76 (1H, m), 1.59 (1H, m), 1.46 (9H, s), 0.89 (3H, t).

e) (2S)-4-[[5-chloro-2-[2-(1,1-dimethylethoxy)-2-oxoethoxy]phenyl]methyl]-2-ethyl-1-piperazinecarboxylic Acid, 1,1-Dimethylethyl Ester The product from example 69 part d) (1 g), the product from example 13 part b) (1.263 g) and MgSO$_4$ (xs) were stirred in THF (50 ml) for 16 h. Sodium triacetoxy borohydride (3.96 g) was added and the reaction stirred for 16 h. The reaction was quenched with water and extracted with ethyl acetate. The organic layer was dried (Na$_2$SO$_4$) and concentrated in vacuo. It was purified by chromatography (silica, (20% EtOAc/isohexane as eluent)), to give the sub-titled compound as a colourless oil (2.03 g).

MS: APCI (+ve): 469 (M+1).

f) [4-Chloro-2-[[(3S)-3-ethyl-1-piperazinyl]methyl]phenoxy]-acetic Acid, 1,1-dimethylethyl Ester Trifluoroacetate Salt To a solution of the product from example 69 part e) (2 g) in dichloromethane (100 ml) was added trifluoroacetic acid (100 ml). The mixture was stirred at RT for 24 h. Toluene (100 ml) was added and reaction was concentrated (bath temp <40° C.) in vacuo to give the sub-titled compound as a yellow oil (3.10 g).

$^1$H NMR (DMSO-d6) δ 7.55 (1H, d), 7.44 (1H, m), 7.06 (1H, d), 4.80 (2H, m), 4.17 (2H, m), 3.65-3.07 (5H, m), 2.95 (1H, m), 2.77 (1H, m), 1.61 (2H, m), 1.44 (9H, s), 0.92 (3H, t).

g) [4-Chloro-2-[[(3S)-3-ethyl-4-(phenylsulfonyl)-1-piperazmyl]methyl]phenoxy]-acetic Acid To a vigorously stirred solution/suspension of the product from example 69 part f) (0.393 g) and solid sodium bicarbonate (0.342 g) in DCM (3 ml) and water (3 ml) was added benzenesulfonyl chloride (0.21 ml) dropwise. The mixture was stirred for 16 h. The organic layer and 1 further DCM extract were combined and purified by passage through SCX resin eluting with MeCN, MeOH followed by 7M NH$_3$ in MeOH. The basic fractions were concentrated in vacuo, dissolved in DCM (3 ml) and treated with TFA (20 ml) for 16 h. Concentration in vacuo and purification by RPHPLC gave the title product as a white foam (45 mg).

$^1$H NMR (DMSO-d6) δ (90° C.) 7.81 (2H, d), 7.66 (1H, t), 7.59 (2H, t), 7.24 (1H, d), 7.18 (1H, dd), 6.81 (1H, d), 4.45 (2H, s), 3.73 (1H, m), 3.64 (1H, d), 3.33 (2H, s), 3.19 (1H, m), 2.61 (2H, d), 1.74 (2H, dt), 1.69 (1H, q), 1.62 (1H, q), 0.78 (3H, t).

MS: APCI (−ve): 451 (M−H).

EXAMPLE 70

[4-chloro-2-[[(3S)-3-ethyl-4-(phenylacetyl)-1-piperazinyl]methyl]phenoxy]-acetic acid

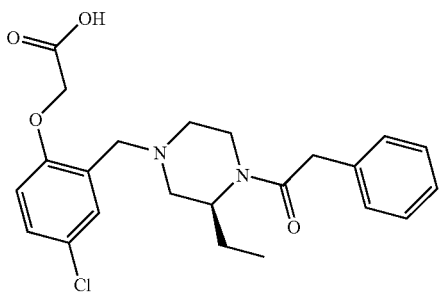 [SMILES: CC[C@H]1CN(Cc2cc(Cl)ccc2OCC(=O)O)CCN1C(=O)Cc1ccccc1]

Prepared from the product from example 69 part f) and phenylacetyl chloride according to the procedure described in example 69 part g) to give the title compound as a white solid (30 mg).

$^1$H NMR (DMSO-d6) δ 7.34-7.19 (7H, m), 6.86 (1H, d), 4.50 (2H, s), 3.48 (2H, s), 4.39-3.12 (5H, m), 2.78 (2H, q), 1.94 (2H, m), 1.82-1.56 (2H, m), 0.73 (3H, t).

MS: APCI (−ve): 429 (M−H).

EXAMPLE 71

(Cis)-[4-chloro-2-[[2,3-dimethyl-4-(phenylacetyl)-1-piperazinyl]methyl]phenoxy]-acetic Acid

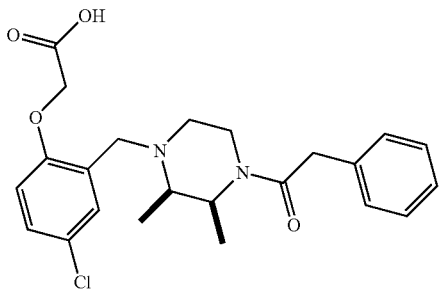 [SMILES: C[C@@H]1[C@H](C)N(C(=O)Cc2ccccc2)CCN1Cc1cc(Cl)ccc1OCC(=O)O]

a) [4-Chloro-2-[(2,3-dimethyl-1-piperazinyl)methyl]phenoxy]-acetic Acid, 1,1-dimethylethyl Ester (cis)-2,3-Dimethylpiperazine (0.115 g), the product from example 13 part b) (0.260 g) and MgSO$_4$ (1 g) were stirred in THF (3 ml) for 2 h. Sodium triacetoxy borohydride (0.65 g) was added and the reaction stirred for 16 h. The reaction was quenched with water and extracted with ethyl acetate. The organic layer was dried (NaaSCU) and concentrated in vacuo. It was purified by passage through SCX resin eluting with MeCN, MeOH followed by 7M NH$_3$ in MeOH. The basic fractions were concentrated in vacuo to give the sub-titled product as a yellow oil (0.188 g).

$^1$H NMR (DMSO-d6) δ 7.39 (1H, s), 7.21 (1H, d), 6.87 (1H, d), 4.68 (2H, s), 3.53 (4H, m), 3.08-2.33 (3H, m), 2.23 (1H, m), 1.41 (9H, s), 1.00 (3H, d), 0.91 (3H, m).

b) (Cis)-[4-chloro-2-[[2,3-dimethyl-4-(phenylacetyl)-1-piperazinyl]methyl]phenoxy]-acetic acid, 1,1-dimethylethyl Ester To a vigorously stirred solution/suspension of the product from example 71 part a) (0.189 g) and solid sodium bicarbonate (0.215 g) in DCM (2 ml) and water (2 ml) was added phenylacetyl chloride (0.14 ml) dropwise. The mixture was stirred for 2 h. The organic layer and 1 further DCM extract were combined, dried (Na$_2$SO$_4$) and purified by passage through SCX resin eluting with MeCN, MeOH followed by 7M NH$_3$ in MeOH. The basic fractions were concentrated in vacuo to give the sub-titled product as a white foam (0.205 g).

MS: APCI (+ve): 487 (M+H).

c) (Cis)-[4-chloro-2-[[2,3-dimethyl-4-(phenylacetyl)-1-piperazinyl]methyl]phenoxy]-acetic Acid The product from example 71 part b) treated with TFA (10 ml) for 16 h. Concentration in vacuo and purification by RPHPLC gave the title product as a white foam (39 mg).

$^1$H NMR (DMSO-d6) (90° C.) δ 7.37 (1H, d), 7.31-7.16 (6H, m), 6.90 (1H, d), 4.55 (2H, s), 4.21 (1H, bs), 3.89 (2H, d), 3.70 (1H, d), 3.64 (1H, d), 3.19 (1H, d), 2.99 (1H, bs), 2.69 (1H, d), 2.38 (1H, m), 2.00 (1H, td), 1.09 (3H, d), 1.03 (3H, d).

MS: APCI (−ve): 429 (M−H).

EXAMPLE 72

[4-chloro-2-[[(3S)-4-(phenylsulfonyl)-3-propyl-1-piperazinyl]methyl]phenoxy]-acetic Acid

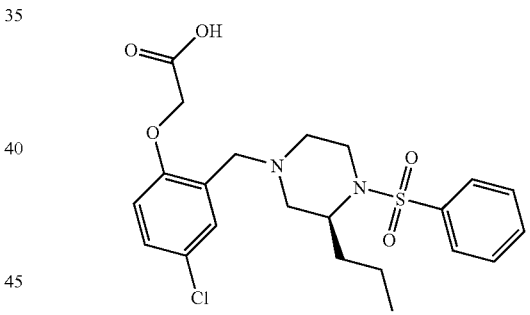

a) (3S)-1-(Phenylmethyl)-3-propyl-2,5-piperazinedione

Prepared from N-BOC-L-norvaline (2.5 g) according to the procedure described in example 69 part a) for the ethyl analogue to give the sub-titled compound as a white solid (2.42 g).

$^1$H NMR (CDCl$_3$) δ 7.33 (3H, m), 7.25 (2H, m), 7.16 (1H, s), 4.66 (1H, d), 4.53 (1H, d), 4.06 (1H, td), 3.86 (1H, d), 3.79 (1H, d), 1.85 (2H, m), 1.42 (2H, sextet), 0.95 (3H, t).

b) (3S)-1-(Phenylmethyl)-3-propyl-piperazine

Prepared from example 72 part a) (2.4 g) according to the procedure described in example 69 part b) for the ethyl analogue to give the sub-titled compound as a yellow oil (1.81 g).

$^1$H NMR (CDCl$_3$) δ 7.33-7.22 (5H, m), 3.52 (1H, d), 3.46 (1H, d), 2.95 (1H, dt), 2.89 (1H, td), 2.76 (2H, m), 2.00 (1H, td), 1.70 (1H, t), 1.42-1.26 (5H, m), 0.89 (3H, t).

c) (2S)-4-(Phenylmethyl)-2-propyl-1-piperazinecarboxylic acid, 1,1-dimethylethyl Ester Prepared from example 72 part b) (1.8 g) according to the procedure described in example 69 part c) for the ethyl analogue to give the sub-titled compound as a colourless oil (1.95 g).

$^1$H NMR (CDCl$_3$) δ 7.32-7.21 (5H, m), 4.02 (1H, s), 3.86 (1H, d), 3.53 (1H, d), 3.38 (1H, d), 3.05 (1H, td), 2.74 (1H, d), 2.66 (1H, d), 2.06 (1H, dd), 2.01 (1H, td), 1.76 (1H, m), 1.60 (1H, m), 1.21 (2H, sextet), 0.91 (3H, t).

d) (2S)-2-Propyl-1-piperazinecarboxylic Acid, 1,1-dimethylethyl Ester

Prepared from example 72 part c) (1.9 g) according to the procedure described in example 69 part d) for the ethyl analogue to give the sub-titled compound as a dark oil (1.38 g).

$^1$H NMR (CDCl$_3$) δ 4.01 (1H, s), 3.84 (1H, d), 2.93 (2H, t), 2.84 (2H, d), 2.67 (1H, td), 1.73 (1H, m), 1.56 (1H, m), 1.46 (9H, s), 1.29 (2H, m), 0.94 (3H, t).

e) (2S)-4-[[5-chloro-2-[2-(1,1-dimethylethoxy)-2-oxoethoxy]phenyl]methyl]-2-propyl-1-piperazinecarboxylic Acid, 1,1-dimethylethyl Ester Prepared from example 72 part d) (0.68 g) and the product from example 13 part b) (0.812 g) according to the procedure described in example 69 part e) for the ethyl analogue to give the sub-titled compound as a white oily solid (1.43 g).

$^1$H NMR (CDCl$_3$) δ 7.43 (1H, d), 7.13 (1H, dd), 6.64 (1H, d), 4.49 (2H, s), 4.04 (1H, s), 3.88 (1H, d), 3.54 (2H, s), 3.08 (1H, t), 2.74 (2H, t), 2.14 (2H, dt), 1.73 (3H, m), 1.47 (9H, s), 1.45 (9H, s), 1.27 (1H, m), 0.94 (3H, t).

f) [4-Chloro-2-[[(3S)-3-propyl-1-piperazinyl]methyl]phenoxy]-acetic Acid, 1,1-dimethylethyl Ester Trifluoroacetate Salt Prepared from example 72 part e) (1.43 g) according to the procedure described in example 69 part f) for the ethyl analogue to give the sub-titled compound as a yellow oil (1.43 g).

MS: APCI (+ve): 327 (M+H-tBu).

g) [4-Chloro-2-[[(3S)-4-(phenylsulfonyl)-3-propyl-1-piperazinyl]methyl]phenoxy]-acetic Acid Prepared from example 72 part f) (0.70 g) and benzenesulfonyl chloride according to the procedure described in example 69 part g) for the ethyl analogue to give the title compound as a white solid (0.154 g).

$^1$H NMR (DMSO-d6) δ 7.80 (2H, m), 7.66 (1H, m), 7.59 (2H, m), 7.25 (1H, d), 7.20 (1H, dd), 6.85 (1H, d), 4.55 (2H, s), 3.81 (1H, s), 3.63 (1H, d), 3.35 (2H, s), 3.19 (1H, dt), 2.61 (2H, m), 1.75 (2H, m), 1.65 (1H, m), 1.52 (1H, m), 1.18 (2H, m), 0.84 (3H, t).

MS: APCI (+ve): 467 (M+H).

EXAMPLE 73

[4-Chloro-2-[[(3S)-4-(phenylacetyl)-3-propyl-1-piperazinyl]methyl]-phenoxy]-acetic Acid

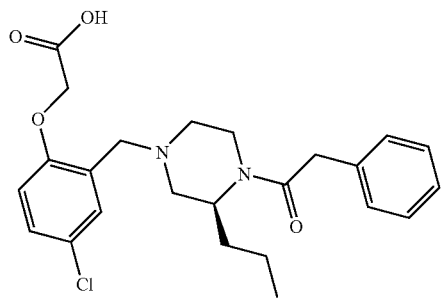 [SMILES: CCC[C@H]1CN(Cc2cc(Cl)ccc2OCC(=O)O)CCN1C(=O)Cc1ccccc1]

Prepared from the product from example 72 part (f) (0.70 g) and phenylacetyl chloride according to the procedure described in example 69 part (g) to give the title compound as a white solid (214 mg).

$^1$H NMR (DMSO-d6) (90° C.) δ 7.36-7.12 (7H, m), 6.88 (1H, d), 4.48 (2H, s), 3.70 (1H, d), 3.64 (1H, d), 3.48 (2H, s), 3.06 (1H, s), 2.75 (2H, m), 1.96 (2H, m), 1.73 (1H, s), 1.55 (1H, s), 1.15 (2H, m), 0.85 (3H, t).

MS: APCI (+ve): 445 (M+H).

EXAMPLE 74

[4-chloro-2-[[(3R,5S)-3,5-dimethyl-4-(phenylacetyl)-1-piperazinyl]-methyl]phenoxy]-acetic Acid

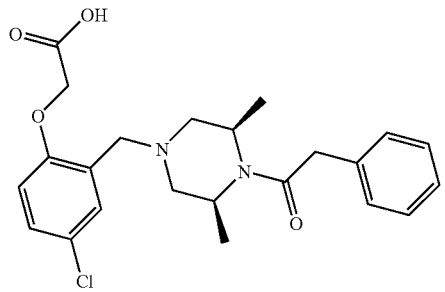 [SMILES: C[C@@H]1CN(Cc2cc(Cl)ccc2OCC(=O)O)C[C@H](C)N1C(=O)Cc1ccccc1]

a) (3R,5S)-3,5-dimethyl-4-(phenylacetyl)-1-piperazinecarboxylic Acid, 1,1-dimethylethyl Ester Prepared by the method of example 67 part (a) using (3R, 5S)-3,5-dimethyl-1-piperazinecarboxylic acid, 1,1-dimethylethyl ester and phenyl acetyl chloride to give the sub-title compound.

MS: ESI (+ve): 333 (M+H).

b) (2R,6S)-2,6-dimethyl-1-(phenylacetyl)-piperazine

TFA (10 ml) was added to a solution of the product from part a) (2.25 g) in DCM (20 ml), and stirred for 18 h, then evaporated in vacuo. The residue was triturated with and ether, filtered to give the sub-title compound (700 mg).

MS: ESI (+ve): 233 (M+H).

c) [4-chloro-2-[[(3R,5S)-3,5-dimethyl-4-(phenylacetyl)-1-piperazinyl]methyl]phenoxy]-acetic Acid, 1,1-dimethylethyl Ester Triethylamine (0.25 ml) was added to a mixture of the product from example 13 part b) (500 mg), and the product from part b) (700 mg) in 1,2-dichloroethane (10 ml). After 1 h sodium triacetoxyborohydride (530 mg) was added and the reaction stirred for a further 20 h. The mixture was partitioned between EtOAc and aqueous NaHCO$_3$. The organic phase was separated and washed with water, dried (MgSO$_4$) and evaporated in vacuo. The residue was purified by chromatography on silica with 20% EtOAc/isohexane as eluent to yield the sub-title compound (600 mg).
MS: ESI (+ve): 489 (M+H).

d) [4-chloro-2-[[(3R,5S)-3,5-dimethyl-4-(phenylacetyl)-1-piperazinyl]methyl]phenoxy]-acetic Acid The title compound was prepared by the method of example 67 part (c) using the product from part (c).
MS: ESI (−ve): 429 (M−H).
$^1$H NMR (DMSO-d6) δ 7.64 (1H, s), 7.37 (1H, d), 7.3-7.18 (5H, m), 7.04 (1H, d), 4.74 (2H, s), 4.5 (2H, s), 4.07 (2H, s), 3.71 (2H, s), 3.1 (2H, d), 2.76 (2H, s), 1.31 (6H, d).

EXAMPLE 75

[4-chloro-2-[[hexahydro-4-(phenylsulfonyl)-1H-1,4-diazepin-1-yl]methyl]phenoxy]-acetic Acid

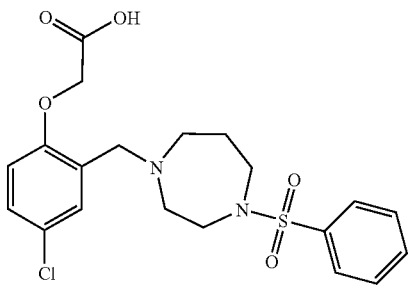 [SMILES: O=C(O)COc1ccc(Cl)cc1CN1CCCN(S(=O)(=O)c2ccccc2)CC1]

a) 1H-1,4-diazepine-1-carboxylic acid, 4-[[5-chloro-2-[2-(1,1-dimethylethoxy)-2-oxoethoxy]phenyl]methyl]hexahydro-1,1-dimethylethyl Ester A solution of the product from example 13 part a), N-(tert-butoxycarbonyl) homopiperazine (0.74 g) and MgSO$_4$ (2 g) in dry tetrahydrofuran (20 ml) was stirred at room temperature for 20 h. Sodium triacetoxyborohydride (2.35 g) was added portionwise over 4 h and the reaction mixture quenched with water, extracted with ethyl acetate (×3), washed with brine (×1), dried (MgSO$_4$), filtered and concentrated in vacuo. Purification by column chromatography (gradient of 20-100% EtOAc in isohexane) gave the sub-title compound as a white solid (1.01 g).
$^1$H NMR (300 MHz, CDCl$_3$) δ 7.44 (1H, d), 7.14 (1H, dd), 6.64 (1H, d), 4.49 (2H, s), 3.72 (2H, s), 3.57-3.41 (4H, m), 2.76-2.62 (4H, m), 1.93-1.71 (2H, m), 1.48 (9H, s), 1.47 (9H, s).

b) [4-Chloro-2-[(hexahydro-1H-1,4-diazepin-1-yl)methyl]phenoxy]-acetic acid, 1,1-dimethylethyl Ester Trifluoroacetic acid (20 ml) was added to a stirred solution of the product of step (a) (1.01 g) in DCM (80 ml). The reaction mixture was stirred for 3 h, diluted with toluene (50 ml) and concentrated in vacuo to give a yellow oil (1.67 g) which was used directly in the next step without further purification.
$^1$H NMR (300 MHz, DMSO-$d6$) δ 7.62 (1H, d), 7.51 (1H, dd), 7.11 (1H, d), 4.81 (2H, s), 4.18 (2H, s), 3.64-3.42 (4H, m), 3.31-3.21 (4H, m), 2.14-2.03 (2H, m), 1.44 (9H, s).

c) Acetic acid, [4-chloro-2-[[hexahydro-4-(phenylsulfonyl)-1H-1,4-diazepin-1-yl]methyl]phenoxy]-,1,1-dimethylethyl Ester Benzene sulphonyl chloride (0.49 ml) was added dropwise over 2 min to a vigorously stirred solution of the product of step (b) (0.56 g) and NaHCO$_3$ (0.34 g) in DCM (3 ml) and water (3 ml). The reaction mixture was vigorously stirred for 2.5 days then diluted with DCM, washed with water (×1) then brine (×1), dried (MgSO$_4$), filtered and concentrated in vacuo. The residue was purified using SCX resin (washed with MeOH and eluted with methanolic ammonia) to give a pale yellow oil (0.23 g).
$^1$H NMR (300 MHz, CDCl$_3$) δ 7.80 (2H, dd), 7.59-7.50 (3H, m), 7.36 (1H, s), 7.13 (1H, dd), 6.63 (1H, d), 4.48 (2H, s), 3.69 (2H, s), 3.41 (4H, t), 2.79-2.68 (4H, m), 1.90-1.79 (2H, m), 1.47 (9H, s).

d) Acetic acid, [4-chloro-2-[[hexahydro-4-(phenylsulfonyl)-1H-1,4-diazepin-1-yl]methyl]phenoxy]

Trifluoroacetic acid (15 ml) was added to the product of step (c) and the reaction mixture stirred for 14 h. Toluene (15 ml) was added and the mixture concentrated in vacuo. The residue was purified using RPHPLC to give the title compound (158 mg) as a white solid.
MS: APCI (+ve): 439 (M+).
$^1$H NMR (300 MHz, DMSO-$d6$) δ 7.80 (2H, dd), 7.74-7.59 (3H, m), 7.36 (1H, s), 7.38 (1H, d), 7.33 (1H, dd), 7.09 (1H, d), 4.51 (2H, s), 4.48 (2H, s), 3.47-3.41 (2H, m), 3.30 (2H, t), 2.99-2.90 (4H, m), 1.98-1.88 (2H, m).

Examples 75 to 77 were synthesised from the product of example 75 part (b) using the method of example 75 parts (c) and (d)

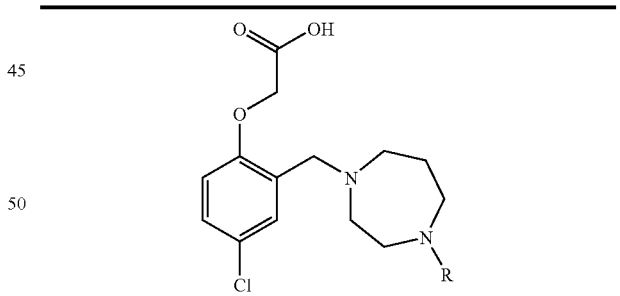

| Example number | EXAMPLE | R | M/Z |
|---|---|---|---|
| 76 | Acetic acid, [4-chloro-2-[[hexahydro-4-[(phenylmethyl)sulfonyl]-1H-1,4-diazepin-1-yl]methyl]phenoxy]- | | 453 [M+] |
| 77 | Acetic acid, [4-chloro-2-[[hexahydro-4-(phenylacetyl)-1H-1,4-diazepin-1-yl]methyl]phenoxy]- | | 417 [M+] |

EXAMPLE 78

[4-Fluoro-2-[4-(phenyl)acetyl-1-piperazipynmethyl]phenoxy]-acetic Acid

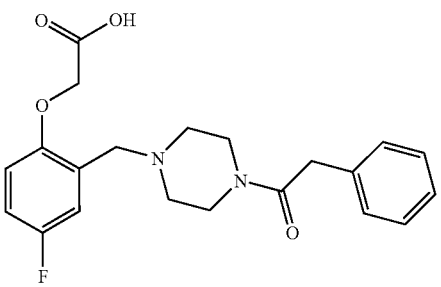 [SMILES: O=C(O)COc1ccc(F)cc1CN1CCN(C(=O)Cc2ccccc2)CC1]

a) 2-Chloromethyl-4-fluoro-1-methoxy-benzene

A solution of 4-fluoromethoxybenzene (5.04 g), formalin (3.6 ml) in concentrated hydrochloric acid (28 ml) and 4M hydrochloric acid in dioxan (16 ml) was stirred at 50° C. for 18 h. The mixture was extracted with ether (×3) and the organics washed with aqueous sodium bicarbonate then brine, dried ($Na_2SO_4$) and evaporated in vacuo to a colourless oil which solidified (6.0 g).
$^1$H NMR (CDCl$_3$) δ 7.10 (1H, dd), 6.99 (1H, m), 6.81 (1H, dd), 4.61 (2H, s), 3.86 (3H, s).

b) 4-[(5-fluoro-2-methoxyphenyl)methyl]-1-piperazinecarboxylic Acid, 1,1-dimethylethyl Ester A mixture of product from part a), 1-BOC-piperazine (5.3 g) and anhydrous potassium carbonate (7.1 g) was stirred in ethanol (20 ml) at room temperature for 18 h. Water was added to the reaction and extracted with dichloromethane (×3), dried ($Na_2SO_4$) and evaporated to give title compound as a viscous oil (8.6 g).
MS: APCI (+ve): 268 (M+H-56).

c) 1-[(5-fluoro-2-methoxyphenyl)methyl]-piperazine

The product from part b) was dissolved (8.6 g) in a mixture of dichloromethane (10 ml) and trifluoroacetic acid (20 ml) to be stirred at 40° C. overnight. The solvents were removed under reduced pressure, using toluene as azeotrope. The resulting solid was dissloved in ethyl acetate and shaken with saturated aqueous sodium bicarbonate (100 ml) and extracted further with ethyl acetate. The combined organics were dried ($Na_2SO_4$) and evaporated to give a solid (8.3 g).
MS: APCI (+ve): 225 (M+H).

d) 1-[(5-fluoro-2-methoxyphenyl)methyl]-4-(phenylacetyl)-piperazine

The product from part c) (1.6 g) was dissolved in dichloromethane (60 ml) and cooled to 0° C., phenylacetyl chloride (1.1 g) and triethylamine (1.2 ml) were added drpwise. The reaction mixture was stirred at room temperature for 4 h then poured into water, extracted with dichloromethane (×3), dried ($Na_2SO_4$), and evaporated to give an orange gum (2.2 g).
MS: APCI (+ve): 343 (M+H).

e) 1-[(5-fluoro-2-hydroxyphenyl)methyl]-4-(phenylacetyl)-piperazine

The product from part d) (1.0 g) was dissolved in dry dichloromethane (30 ml), cooled to 0° C. and 1.0M boron tribromide in dichloromethane (16 ml) then added. The reaction mixture was quenched after 50 minutes with ice-water and the organic layer was separated. The aqueous layer was basified with aqueous potassium carbonate and then extracted with ethyl acetate (×3), the combined organics were washed with brine, dried ($Na_2SO_4$) to give the sub-title compound as a white solid (0.61 g).
MS: APCI (+ve): 365 (M+H).

f) [4-fluoro-2-[[4-(phenylacetyl)-1-piperazinyl]methyl]phenoxy]-acetic Acid, 1,1-dimethylethyl Ester The product from part e) (0.33 g) was suspended in acetonitrile (20 ml) and to it was added anhydrous potassium carbonate (0.15 g) and f-butyl bromoacetate (0.22 g), the reaction was heated to reflux for 24 hours. Then cooled to room temperature, the mixture was concentrated in vacuo and water added. The pH was adjusted to 6 by addition of aqueous ammonium chloride and extracted with ethyl acetate (×3), washed with brine, dried ($Na_2SO_4$), and concentrated in vacuo to give the sub-title compound (0.29 g).
MS: APCI (+ve): 443 (M+H).

g) [4-Fluoro-2-[4-(phenyl)acetyl-1-piperazinyl]methyl]phenoxy]-acetic Acid

The product from part f) (0.22 g) was dissolved in trifluoroacetic acid (2 ml) and stirred under nitrogen for 24 hours. The solvents were removed under reduced pressure using toluene as azeotrope and the residue purified by reverse phase HPLC to give the title compound as a white solid (44 mg).
MS: APCI (−ve): 385 (M−1).
$^1$H NMR (DMSO-d6) δ 7.22 to 7.37 (5H, m), 7.08 (1H, dd), 6.99 (1H, m), 6.83 (1H, dd), 4.73 (2H, s), 3.90 (2H, bs), 3.71 (2H, s), 3.68 (2H, t), 3.65 (2H, s), 2.75 (2H, bs), 2.44 (2H, bs).

EXAMPLE 79

[4-Fluoro-2-[[4-[(phenyl)sulfonyl]-1-piperazinyl]methyl]phenoxy]-acetic Acid

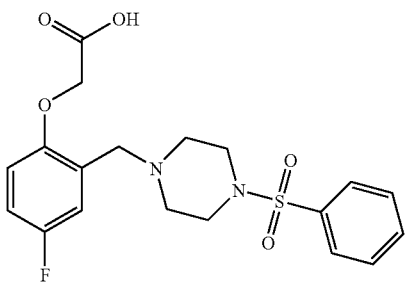

a) 2-[[(4-Phenyl)sulphonyl1-piperazinyl]-4-fluoro-1-methoxybenzene

The product from Example 43 part c) (1.6 g) was dissolved in dichloromethane (60 ml) at room temperature before addition of benzenesulfonyl chloride (1.3 g) and triethylamine (1.2 ml) was made. Stirred at room temperature for 4 hours and poured into water, extracted with dichloromethane (×3), dried ($Na_2SO_4$), and concentrated in vacuo to give the sub-title compound (2.1 g).
MS: APCI (+ve): 365 (M+H).

b) 2-[[(4-Phenyl)sulphonyl1-piperazinyl]-4-fluorophenol

The product from part a) (2.1 g) was dissolved in dry dichloromethane (50 ml), cooled to 0° C. A solution of 1.0M boron tribromide in dichloromethane (12 ml) was added. After 50 minutes the reaction was quenched with ice-water and the organics separated. The aqueous layer was basified with aqueous potassium carbonate and extracted with ethyl acetate (×3) and the combined organics were washed with brine, then dried ($Na_2SO_4$) to give the sub-title compound (1.4 g).
MS: APCI (+ve): 351 (M+H).

c) [4-Fluoro-2-[4-(phenyl)sulfonyl-1-piperazinyl] methyl]-phenoxy]-acetic Acid t-butyl Ester Anhydrous potassium carbonate (0.23 g) and t-butyl bromoacetate (0.33 g) were added to a suspension of the product from part b) (0.53 g) in acetonitrile (30 ml). The reaction heated to reflux for 24 hours, cooled to room temperature and concentrated in vacuo. Water was added and the pH was adjusted to 6 by addition of aqueous ammonium chloride and extracted with ethyl acetate (×3), shaken with brine, dried ($Na_2SO_4$), and concentrated in vacuo to give a gum (0.37 g).
MS: APCI (+ve): 465 (M+H).

d) [4-Fluoro-2-[[4-[(phenyl)sulfonyl]-1-piperazinyl] methyl]phenoxy]-acetic Acid The product from part c) (0.27 g) was dissolved in trifluoroacetic acid (2 ml) and stirred under nitrogen for 48 hours. The solvents were removed under reduced pressure using toluene as azeotrope and the residue purified reverse phase HPLC using to give the title compound (0.14 g).
MS: APCI (−ve) 407 (M−1).
$^1$H NMR (DMSO-d6) δ 7.73 (2H, d), 7.62 (1H, t), 7.54 (2H, t), 7.06 (1H, m), 6.95 (1H, m), 6.90 (1H, dd), 4.67 (2H, s), 3.73 (2H, s), 3.34 (4H, bs), 2.85 (4H, bs).

EXAMPLE 80

[4-Fluoro-2-[[4-[(phenylmethyl)sulfonyl]-1-piperazinyl]methyl]phenoxy]-acetic Acid

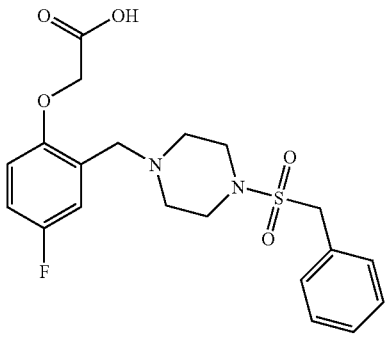 [SMILES: O=C(O)COc1ccc(F)cc1CN1CCN(S(=O)(=O)Cc2ccccc2)CC1]

a) 1-[(5-fluoro-2-methoxyphenyl)methyl]-4-[(phenylmethyl)sulfonyl]-piperazine Phenylmethanesulfonyl chloride (0.7 g) and triethylamine (0.6 ml) were added dropwise to a solution of the product from Example 43 part c) (0.8 g) in dichloromethane (30 ml) at room temperature. The reaction mixture was stirred at room temperature for 4 hours then poured into water, extracted with dichloromethane (×3), dried ($Na_2SO_4$), and concentrated in vacuo to give a solid (0.98 g).
MS: APCI (+ve): 379 (M+H).

b) 1-[(5-fluoro-2-hydroxyphenyl)methyl]-4-[(phenylmethyl)sulfonyl]-piperazine The sub-title compound was prepared by the method of example 78 part e) from the product from part a).
MS: APCI (+ve): 365 (M+H).

c) [4-fluoro-2-[[4-[(phenylmethyl)sulfonyl]-1-piperazinyl]methyl]phenoxy]-acetic Acid, 1,1-dimethylethyl Ester The sub-title compound was prepared by the method of example 78 part f) from the product from part b).
MS: APCI (+ve): 479 (M+H).

d) [4-fluoro-2-[[4-[(phenylmethyl)sulfonyl]-1-piperazinyl]methyl]phenoxy]-acetic Acid The title compound was prepared by the method of example 78 part g) from the product from part c).
MS: APCI (−ve): 407 (M−1).
$^1$H NMR (DMSO-d6) δ 7.35 to 7.44 (5H, m), 7.28 (1H, m), 7.23 (1H, m), 7.10 (1H, dd), 4.78 (2H, s), 4.52 (2H, s), 4.19 (2H, s), 3.32 (4H, bs), 3.09 (4H, bs).

EXAMPLE 81

(2S)-2-[4-fluoro-2-[[4-(phenylacetyl)-1-piperazinyl]methyl]phenoxy]-propanoic Acid

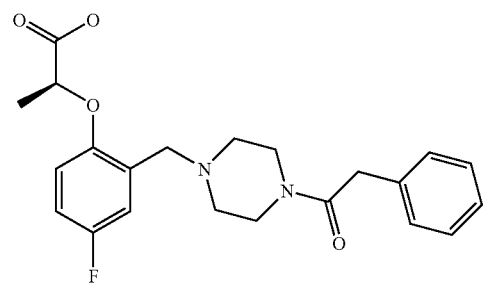 [SMILES: C[C@H](Oc1ccc(F)cc1CN1CCN(C(=O)Cc2ccccc2)CC1)C(=O)O]

a) (2S)-2-[4-fluoro-2-[[4-(phenylacetyl)-1-piperazinyl]methyl]phenoxy]-propanoic Acid, 1,1-dimethylethyl Ester The product from Example 78 part e) (0.44 g) was suspended in anhydrous THF (5 ml) (+)-tert-butyl D-lactate (0.22 g) and triphenylphosphine (0.42 g) were added and the reaction was then cooled to 0° C. Diisopropyl azodicarboxylate (0.35 ml) was added dropwise and the resulting mixture was allowed to stir at room temperature overnight, then concentarted in vacuo. The residue was purified by silica flash chromatography using 10:1 dichloromethane/methanol as eluent to give the sub-title compound as a gum (0.31 g).
MS: APCI (+ve): 401 (M+1-56).

b) (2S)-2-[4-fluoro-2-[[4-(phenylacetyl)-1-piperazinyl]methyl]phenoxy]-propanoic Acid The title compound was prepared by the method of example 78 part g) using the product form part a).

MS: APCI (+ve): 401 (M+1).

¹H NMR (DMSO-d6) δ 9.40 (1H, bs), 7.33 (2H, t), 7.27 (1H, t), 7.22 (2H, d), 7.03 (2H, m), 6.86 (1H, m), 4.95 (1H, q), 4.29 (1H, d), 3.97 (1H, bs), 3.89 (1H, bs), 3.79 (2H, bs), 3.69 (2H, t), 3.17 (1H, d), 2.83 (2H, bs), 2.62 (2H, bs), 1.62 (3H, d).

EXAMPLE 82

(2S)-2-[4-fluoro-2-[[4-(phenylsulfonyl)-1-piperazinyl]methyl]phenoxy]-propanoic Acid

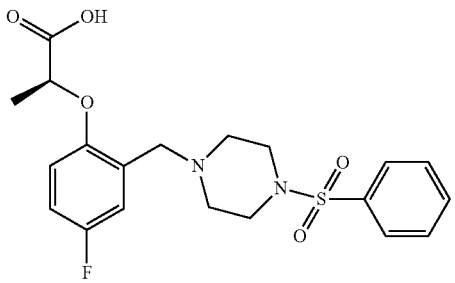 [SMILES: C[C@H](Oc1ccc(F)cc1CN1CCN(S(=O)(=O)c2ccccc2)CC1)C(=O)O]

a) (2S)-2-[4-fluoro-2-[[4-(phenylsulfonyl)-1-piperazinyl]methyl]phenoxy]-propanoic Acid, 1,1-dimethylethyl Ester The sub-title compound was prepared by the method of example 81 part a) using the product from example 79 part b)
MS: APCI (+ve): 479 (M+1).

b) (2S)-2-[4-fluoro-2-[[4-(phenylsulfonyl)-1-piperazinyl]methyl]phenoxy]-propanoic Acid The title compound was prepared by the method of example 78 part g) using the product form part a).
MS: APCI (−ve): 421 (M−1)

¹H NMR (DMSO-d6) δ 7.72 (2H, d), 7.63 (1H, t), 7.54 (2H, t), 7.02 (1H, m), 6.93 (1H, m), 6.88 (1H, m), 4.88 (1H, m), 4.23 (1H, d), 3.04 (1H, d), 2.82 (4H, bs), 2.82 (4H, bs), 1.62 (3H, d).

EXAMPLE 83

(2S)-2-[4-fluoro-2-[[4-[(phenylmethyl)sulfonyl]-1-piperazinyl]methyl]phenoxy]-propanoic Acid

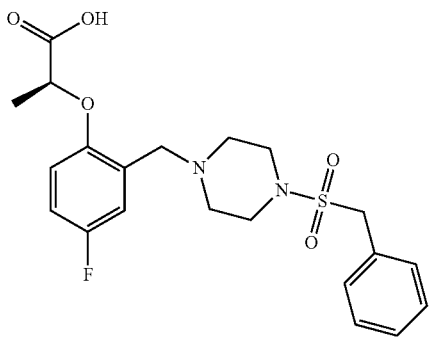 [SMILES: C[C@H](Oc1ccc(F)cc1CN1CCN(S(=O)(=O)Cc2ccccc2)CC1)C(=O)O]

a) (2S)-2-[4-fluoro-2-[[4-[(phenylmethyl)sulfonyl]-1piperazinyl]methyl]phenoxy]-propanoic Acid, 1,1-dimethylethyl Ester The sub-title compound was prepared by the method of example 81 part a) using the product from example 80 part b).
MS: APCI (+ve): 492 (M+1).

b) (2S)-2-[4-fluoro-2-[[4-[(phenylmethyl)sulfonyl]-1piperazinyl]methyl]phenoxy]-propanoic Acid The title compound was prepared by the method of example 78 part g) using the product from part a).
MS: APCI (−ve): 437 (M−1).

¹H NMR (DMSO-d6) δ 7.41 (5H, m), 7.06 (1H, m), 6.99 (1H, m), 6.86 (1H, dd), 4.893 (1H, q), 4.23 (4H, m), 3.31 (4H, bs), 2.71 (4H, bs), 1.65 (3H, d).

EXAMPLE 84

[4-chloro-2-[[methyl[1-(phenylsulfonyl)-3-pyrrolidinyl]amino]methyl]phenoxy]-acetic Acid, Trifluoroacetate

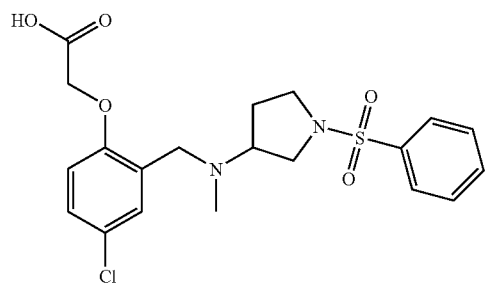 [SMILES: CN(Cc1cc(Cl)ccc1OCC(=O)O)C1CCN(S(=O)(=O)c2ccccc2)C1]

(a) [1-(phenylsulfonyl)-3-pyrrolidinyl]-carbamic acid, 1,1-dimethylethyl Ester

To a solution of 3-(tert-butoxycarbonylamino)pyrrolidine (0.7 g) in THF (20 ml) cooled to 0° C. was added triethylamine (0.52 ml) followed by the addition of benzenesulfonyl chloride (0.48 ml) dropwise over 5 minutes. After stirring for 2 hours the mixture was poured into water and the organics extracted into ether. The ether extractions were combined, washed with brine, dried (MgSO₄) and concentrated in vacuo to give crude material. Trituration with ether gave subtitle compound as a colourless solid (0.9 g).

¹H NMR (CDCl₃) δ 7.85-7.82 (2H, m), 7.65-7.60 (1H, m), 7.58-7.53 (2H, m), 4.48 (1H, s), 4.09 (1H, s), 3.45-3.33 (2H, m), 3.21 (2H, s), 2.04 (1H, m), 1.75 (1H, s), 1.41 (9H, s).

(b) methyl[1-(phenylsulfonyl)-3-pyrrolidinyl]-carbamic Acid, 1,1-dimethylethyl Ester To a suspension of sodium hydride (60% dispersion in mineral oil) (49 mg) in tetrahydrofuran (10 ml) was added the product from part (a) (400 mg) as a solution in tetrahydrofuran (5 ml). After 30 minutes methyl iodide (90 ul) was added and the reaction stirred overnight. The mixture was poured into water and the organics extracted into ether. The ether extractions were combined, washed with brine, dried (MgSO₄) and concentrated in vacuo to give crude product.

Purification by column chromatography (eluent 20% EtOAc/Hexane) gave the subtitle compound as an oil (235 mg).
MS: APCI (+ve): 341 (M+H⁺).

(c) N-methyl-1-(phenylsulfonyl)-3-pyrrolidmamine, Trifluoroacetate

To a solution of the product from part (b) (231 mg) in dichloromethane (5 ml) was added trifluoroacetic acid (5 ml). After stirring at room temperature for 2 hours the reaction was concentrated hi vacuo and the residue triturated with ether to give subtitle compound as a solid (220 mg).
¹H NMR (d6-DMSO) δ 8.79 (2H, s), 7.84-7.64 (5H, m), 3.67 (1H, m), 3.40-3.31 (2H, m), 3.24 (1H, m), 3.09 (1H, m), 2.54 (3H, s), 2.10 (1H, m), 1.88 (1H, m).
MS: APCI (+ve): 241 (M+H⁺).

(d) [4-chloro-2-(hydroxymethyl)phenoxy]-acetic Acid, 1,1-dimethylethyl Ester

To a solution of (4-chloro-2-formylphenoxy)-acetic acid, 1,1-dimethylethyl ester (2.1 g) in ethanol (20 ml) was added sodium borohydride (0.29 g). After stirring for 10 minutes the reaction was concentrated in vacuo and water added to the residue. The organics were extracted into ethylacetate, washed with brine, dried (MgSO₄) and concentrated in vacuo to give the subtitle compound as an oil (2 g).
¹H NMR (CDCl₃) 7.29 (1H, d), 7.20 (1H, dd), 6.72 (1H, d), 4.68 (2H, s), 4.57 (2H, s), 2.04 (1H, s), 1.48 (9H, s).

(e) [4-chloro-2-[[(methylsulfonyl)oxy]methyl]phenoxy]-acetic Acid, 1,1-dimethylethyl Ester A solution of the product of part (d) (1 g) and triethylamine (0.51 ml) in dichloromethane (10 ml) was cooled to 0° C. Methanesulfonyl chloride (0.29 ml) was then added dropwise and the reaction was allowed to reach room temperature. After stirring for 3 hours the reaction was diluted with dichloromethane, washed with water, NaHCO₃ (aq), brine, dried (MgSO₄) and concentrated in vacuo to give the subtitle compound as an oil (1.13 g).
¹H NMR (CDCl₃) δ 7.40 (1H, s), 7.29 (1H, d) 6.71 (1H, d), 5.31 (2H, s), 4.56 (2H, s), 3.05 (3H, s), 1.47 (9H, s).

(f) [4-chloro-2-[[methyl[1-(phenylsulfonyl)-3-pyrrolidinyl]amino]methyl]phenoxy]-acetic Acid, 1,1-dimethylethyl Ester A solution of the product from part (c) (217 mg), part (e) (213 mg) and triethylamine (0.17 ml) in DMF (5 ml) was stirred overnight at room temperature. The reaction was diluted with water, pH adjusted to 9 using NaHCO₃ (aq) and the organics extracted into ether. The ether extractions were combined, washed with brine, dried (MgSO₄) and concentrated in vacuo to give a crude material. Purification using column chromatography (eluent 33% EtOAc/Hexane) gave the subtitle compound as an oil (93 mg).
Used without Characterisation in Step (g)

(g) [4-chloro-2-[[methyl[1-(phenylsulfonyl)-3-pyrrolidinyl]amino]methyl]phenoxy]-acetic Acid, Trifluoroacetate To a solution of the product from part (f) (93 mg) in dichloromethane (3 ml) was added trifluoroacetic acid (3 ml). After 2 hours the reaction was concentrated in vacuo and the residue triturated with ether to give title compound as a white solid (70 mg).
¹H NMR (d6-DMSO at 90° C.) δ 7.82 (2H, d), 7.73-7.60 (3H, m), 7.41 (1H, d), 7.35 (1H, dd), 7.05 (1H, d), 4.69 (2H, s), 3.93 (2H, s), 3.59-3.09 (5H, m), 2.40 (3H, s), 2.16 (1H, m), 1.99 (1H, m).
MS: APCI (−ve): 437 (M−H).

EXAMPLE 85

[4-Cyano-2-[[(3S)-3-methyl-4-(phenylacetyl)-1-piperazinyl]methyl]phenoxy]acetic Acid

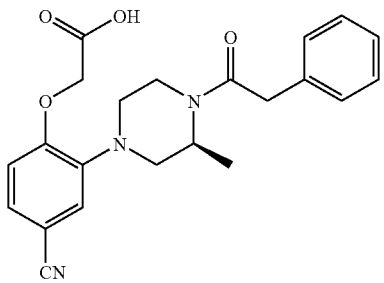 [SMILES: C[C@H]1CN(c2cc(C#N)ccc2OCC(=O)O)CCN1C(=O)Cc1ccccc1]

a) (4-Cyano-2-formylphenoxy)acetic Acid, 1,1-dimethylethyl Ester

Prepared by the method of example 1 part (d) using 3-formyl-4-hydroxy-benzonitrile to give the title compound (1.4 g).
MS: APCI (+ve): 262 (M+1).
¹H NMR (CDCl₃) δ 10.51 (1H, s), 8.16 (1H, d), 7.80 (1H, dd), 6.94 (1H, d), 4.73 (2H, s), 1.49 (9H, s).

b) [4-Cyano-2-[[(3S)-3-methyl-4-(phenylacetyl)-1-piperazinyl]methyl]phenoxy]acetic Acid Prepared by the method of example 55 part (b), using the product from part (a) (250 mg) and the product from example 64 part (b) (330 mg) to give the title compound (90 mg).
MS: APCI (−ve): 406 (M−1).
¹H NMR (DMSO-d6) δ 7.73 (1H, d), 7.69 (1H, dd), 7.30 (2H, m), 7.21 (3H, m), 7.04 (1H, d), 4.73 (2H, s), 4.61-4.51 (1H, m), 4.26-4.12 (1H, m), 3.68 (2H, s), 3.52 (2H, s), 3.29-3.16 (1H, m), 2.93-2.72 (1H, m), 2.72-2.62 (1H, m), 2.09 (1H, m), 1.93 (1H, m), 1.18 (3H, d).

EXAMPLE 86

[4-Methyl-2-[[(3S)-3-methyl-4-(phenylacetyl)-1-piperazinyl]methyl]phenoxy]acetic Acid

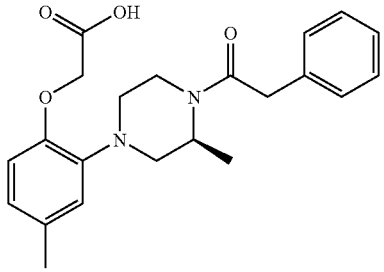 [SMILES: Cc1ccc(OCC(=O)O)c(N2CCN(C(=O)Cc3ccccc3)[C@@H](C)C2)c1]

a) (2-Formyl-4-methylphenoxy)acetic Acid

Prepared by the method of example 1 part (d) using 2-hydroxy-5-methyl-benzaldehyde to give the title compound.

MS: APCI (+ve): 251 (M+1).

$^1$H NMR (CDCl$_3$) δ 10.54 (1H, s), 7.66 (1H, d), 7.33 (1H, dd), 6.75 (1H, d), 4.61 (2H, s), 2.32 (3H, s), 1.48 (9H, s).

b) [4-Methyl-2-[[(3S)-3-methyl-4-(phenylacetyl)-1-piperazinyl]methyl]phenoxy]acetic Acid Prepared by the method of example 55 part (b), using the product from part (a) (240 mg) and the product from example 64 part (b) (330 mg) to give the title compound (100 mg).

MS: APCI (−ve): 397 (M−1).

$^1$H NMR (DMSO-d6) δ 7.31 (2H, m), 7.22 (3H, m), 7.14 (1H, d), 7.02 (1H, dd), 6.82 (1H, d), 4.56 (2H, dd), 4.30-4.16 (1H, m), 3.85-3.48 (2H, m), 3.69 (2H, s), 3.57 (2H, s), 2.90-2.72 (2H, m), 2.28-2.16 (1H, m), 2.12-1.98 (1H, m), 1.17 (3H, d).

EXAMPLE 87

[2-[[(3S)-3-Methyl-4-(phenylacetyl)-1-piperazinyl]methyl]-4-(trifluoromethyl)phenoxy]acetic Acid

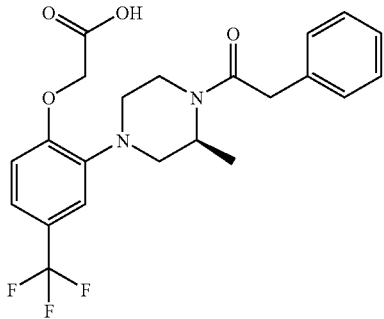 [SMILES: C[C@H]1CN(c2cc(C(F)(F)F)ccc2OCC(=O)O)CCN1C(=O)Cc1ccccc1]

Prepared by the method of example 55 part (b), using the product from example 1 part (d) (300 mg) and the product from example 64 part (b) (330 mg) to give the title compound (130 mg).

MS: APCI (−ve): 451 (M−1).

$^1$H NMR (DMSO-d6) δ 7.71 (1H, s), 7.56 (1H, d), 7.30 (2H, m), 7.21 (3H, m), 7.05 (1H, d), 4.72 (2H, s), 4.56 (1H, m), 4.22 (1H, m), 3.81-3.52 (1H, m), 3.68 (2H, s), 3.56 (2H, s), 3.23 (1H, m), 2.93-2.59 (2H, m), 2.02 (2H, m), 1.17 (3H, d).

EXAMPLE 88

Sodium[4-(1-methylethyl)-2-[[4-(phenylsulfonyl)-1piperazinyl]methyl]phenoxy]-acetate

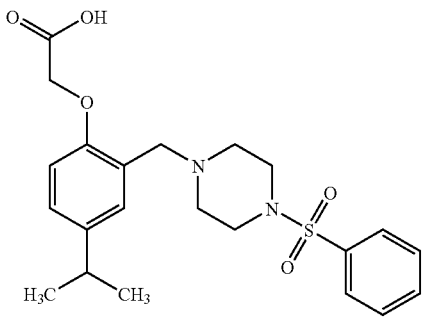 [SMILES: CC(C)c1ccc(OCC(=O)O)c(CN2CCN(S(=O)(=O)c3ccccc3)CC2)c1]

a) 1,1-Dimethylethyl 4-[[2-methoxy-5-(1-methylethyl)phenyl]methyl]-1-piperazinecarboxylate A mixture of 2-(chloromethyl)-1-methoxy-4-(1-methylethyl)benzene (2.55 g) 1,1-dimethylethyl 1-piperazinecarboxylate (2.41 g) and potassium carbonate (3.17 g) in ethanol (20 ml) was stirred for 20 h. Water was added and the mixture was extracted with dichloromethane. The organic extracts were dried (MgSO$_4$), evaporated in vacuo and purified by chromatography (silica, petrol—ether as eluent) to give the sub-title compound (2.17 g).

MS: APCI (+ve): 349 (M+H$^+$).

b) 1-[[2-Methoxy-5-(1-methylethyl)phenyl]methyl]-piperazine

A solution of the product from step (a) (1.98 g) in TFA (4 ml) and dichloromethane (2 ml) was stirred for 2 h. The solvent was removed in vacuo and the residue azeotroped with toluene. Aq. potassium carbonate was added and the mixture was extracted with dichloromethane. The organic extracts were dried (MgSO$_4$) and evaporated in vacuo to give the sub-title compound (1.79 g).

MS: APCI (+ve): 249 (M+H$^+$).

c) 1-[[2-Methoxy-5-(1-methylethyl)phenyl]methyl]-4-(phenylsulfonyl)-piperazine

Phenylsulfonyl chloride (0.24 ml) was added to a solution of the product from step (b) (396 ml) and triethylamine (0.44 ml) in dichloromethane (3 ml) and the mixture was stirred for 3 h. Water was added and the mixture was extracted with dichloromethane. The organic extracts were dried (MgSO$_4$), evaporated in vacuo and purified by chromatography (silica, petrol—ether as eluent) to give the sub-title compound (431 mg).

MS: APCI (+ve): 389 (M+H$^+$).

d) 1-[[2-Hydroxy-5-(1-methylethyl)phenyl]methyl]-4-(phenylsulfonyl)-piperazine

Boron tribromide (2.3 ml, 1 M in DCM) was added to a solution of the product fromm step c) (431 mg) in DCM at 0° C. Aq sodium bicarbonate was added after 20 min and the mixture was extracted with dichloromethane. The organic extracts were dried (MgSO$_4$) and, evaporated in vacuo to give the sub-title compound (553 mg).

MS: APCI (+ve): 375 (M+H$^+$).

e) Ethyl[4-(1-methylethyl)-2-[[4-(phenylsulfonyl)-1-piperazinyl]methyl]phenoxy]-acetate A mixture of the product from step (d) (244 mg), ethyl bromoacetate (0.1 ml) and potassium carbonate (185 mg) in acetone was heated under reflux for 2 days. Water was added and the mixture was extracted with diethyl ether. The organic extracts were dried (MgSO$_4$), evaporated in vacuo and purified by chromatography (silica, petrol—ether as eluent) to give the sub-title compound (113 mg).

MS: APCI (+ve): 461 (M+H$^+$).

f) Sodium[4-(1-methylethyl)-2-[[4-(phenylsulfonyl)-1-piperazinyl]methyl]phenoxy]-acetate A solution of the product from step (e) (113 mg) in NaOH (0.25 ml, 1M), THF (1.5 ml) and MeOH (1 ml) was stirred for 4 h. The solvent was removed in vacuo and the residue triturated with ether to give the title compound (97 mg)

MS: APCI (−ve): 431 (M−1).

¹H NMR (DMSO-d6) δ 7.61-7.64 (5H, m), 6.99 (1H, s), 6.97 (1H, d), 6.67 (1H, d), 4.09 (2H, s), 3.49 (2H, s), 2.91 (4H, s), 2.76 (1H, heptet), 2.52 (4H, s), 1.12 (6H, d).

EXAMPLE 89

[4-chloro-2-[[(3S)-4-[(4-fluorophenyl)acetyl]-3-methyl-1-piperazinyl]methyl]phenoxy]-acetic Acid

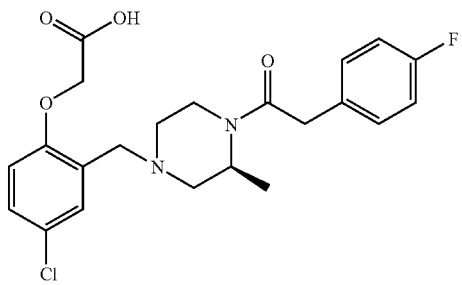 [SMILES: C[C@H]1CN(Cc2cc(Cl)ccc2OCC(=O)O)CCN1C(=O)Cc1ccc(F)cc1]

a) (3S)-3-methyl-1-(triphenylmethyl)-piperazine (S)+-2-methylpiperazine (10 g) was dissolved in acetonitrile (140 ml) and cooled to 5-10° C. whereupon triethylamine (35 ml) was added, followed by drop wise addition of a solution of trityl chloride 27.9 (g) in DCM (80 ml). The reaction was stirred for 1 h at room temperature. The resulting slurry was cooled to approximately 0° C. then filtered. The filtrate was evaporated in vacuo and the residue was purified by chromatography (silica, 1-4% MeOH/DCM as eluent) to give the sub-title compound (29 g).

b) (2S)-1-piperazinecarboxylic Acid, 2-methyl-4-(triphenylmethyl)-1,1-dimethylethyl Ester Triethylamine (24 ml) was added to a solution of the product from part a) (29 g) in methanol (350 ml). BOC-anhydride (18.9 g) was then added to the reaction mixture and stirred overnight. The solvents were evaporated in vacuo and the residue partitioned between ethyl acetate and saturated brine. The organic layer was separated and washed with brine, dried (Na₂SO₄) the concentrated in vacuo to give the sub-title compound (41 g).

¹H NMR (CDCl₃) δ 7.49-7.16 (15H, m), 4.13 (1H, t), 3.74 (1H, d), 3.33 (1H, t), 2.97 (4H, m), 1.68 (3H, dd) and 1.33 (9H, s).

c) (2S)-2-methyl-1-piperazinecarboxylic acid-1,1-dimethylethyl Ester

2M HCl (50 ml) was added drop wise to a solution of the product of part (b) (31.8 g) in ethanol (1500 ml), the reaction was stirred for 1.5 h. Solid sodium hydrogen carbonate (8.4 g) was added and stirred for 1 h, then concentrated in vacuo. The residue was purified by chromatography (silica, 0-2-5% MeOH/DCM as eluent) to remove the by-products, then eluted with 10% MeOH/DCM to give the sub-title compound (9.3 g).

¹H NMR (CDCl₃) δ 4.51 (1H, t), 4.05 (1H, d), 3.41 (2H, m), 3.20 (1H, d), 3.09 (1H, dd), 2.87 (1H, t) and 1.44 (12H, m).

d) (2S)-4-[[5-chloro-2-[2-(1,1-dimethylethoxy)-2-oxoethoxy]phenyl]methyl]-2-methyl-,1-piperazinecarboxylic Acid, 1,1-dimethylethyl Ester The product of example 13 part (a) (9.1 g), the product of part c) MgSO₄ (18 g) and anhydrous THF (350 ml) were charged to a flask and stirred overnight. Sodium triacetoxy borohydride (11.7 g) was added portion wise and the mixture stirred overnight then concentrated in vacuo. The residue was partitioned between ethyl acetate and water; the organic phase was washed with ethyl acetate. The combined organic extracts were dried (Na₂SO₄) and concentrated in vacuo. The residue was purified by chromatography (silica, 80% isohexane/ethyl acetate as eluent) to give the sub-title compound (9.2 g).

MS: ESI (+ve): 455 (M+1).

¹H NMR (CDCl₃) δ 7.44 (1H, d), 7.12 (1H, dd), 6.64 (1H, d), 4.49 (2H, s), 4.2 (1H, s), 3.8 (1H, d) 3.55 (2H, s), 3.1 (1H, t), 2.65 (1H, d), 2.25 (1H, d), 2.21 (1H, d), 2.09 (1H, t) and 1.28 (3H, d).

e) (2S)-4-[[5-chloro-2-[2-(1,1-dimethylethoxy)-2-oxoethoxy]phenyl]methyl]-2-methyl-1-piperazinecarboxylic Acid, 1,1-dimethylethyl Ester TFA Salt TFA (13 ml) was added to a solution of the product of step (d) (3.8 g) in DCM (40 ml) and stirred for 50 min. Toluene was added and the mixture was concentrated in vacuo to give the sub-title compound.

MS: ESI (+ve): 355 (M+H).

¹H NMR (CDCl₃) δ 7.41 (2H, m), 7.25-6.98 (4H, m), 6.78 (1H, d), 4.66 (2H, d), 4.05 (1H, broad s), 3.77 (3H, broad s), 3.66 (3H, broad s), 2.36 (1H, t), 2.65 (1H, d), 2.25 (1H, d), 2.21 (1H, d), 2.09 (1H, t) and 1.28 (1H, d).

f) [4-chloro-2-[[(3S)-4-[(4-fluorophenyl)acetyl]-3-methyl-1-piperazinyl]methyl]phenoxy]-acetic Acid, 1,1-dimethylethyl Ester The product of part (e) (0.39 g) was dissolved in DCM (10 ml) and a solution of sodium hydrogen carbonate (0.42 g) in water (10 ml) was added. 4-fluorophenylacetyl chloride (0.18 g) was added drop wise and stirred overnight at room temperature. The reaction mixture was washed with DCM (×3). The combined organic extracts were dried (Na₂SO₄) and evaporated to give the sub-title compound (0.18 g).

g) [4-chloro-2-[[(3S)-4-[(4-fluorophenyl)acetyl]-3-methyl-1-piperazinyl]methyl]phenoxy]-acetic Acid The product from part (f) (180 mg) and TFA (2 ml) were charged to a flask and stirred for 5 h. Toluene was added and the reaction mixture concentrated in vacuo. The residue was purified by reverse phase HPLC to give the title compound (60 mg).

MS: APCI (+ve): 435 (M+H).

¹H NMR (CDCl₃ at 50° C.) δ 7.28 (2H, m), 7.17 (2H, m), 7.00 (2H, m), 6.9 (1H, d), 4.59 (2H, d), 4.5 (1H, broad s), 3.91 (1H, broad s), 3.69 (1H, d), 3.66 (2H, s), 3.44 (1H, broad s), 3.40 (1H, broad s), 2.38 (1H, d), 2.09 (1H, t) and 1.33 (3H, d).

EXAMPLE 90

[4-chloro-2-[[(3S)-4-[(2,4-difluorophenyl)acetyl]-3-methyl-1-piperazinyl]methyl]phenoxy]-acetic Acid

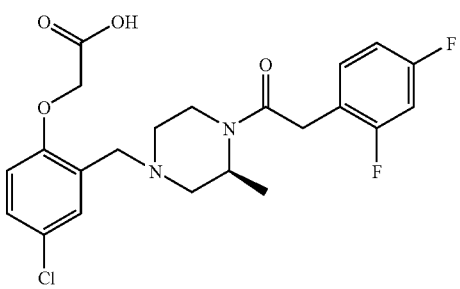 [SMILES: C[C@H]1CN(Cc2cc(Cl)ccc2OCC(=O)O)CCN1C(=O)Cc1ccc(F)cc1F]

a) 2,4-difluoro-benzeneacetyl Chloride 2,4-difluoroacetic acid (0.3 g) and DCM (10 ml) were charged to a flask. Oxalyl chloride (0.2 ml) was added followed by DMF (catalytic amount), and stirred for 1 h. Toluene was added and the reaction mixture was concentrated in vacuo to give the sub-title compound—used directly without characterisation.

b) [4-chloro-2-[[(3S)-4-[(2,4-difluorophenyl)acetyl]-3-methyl-1-piperazinyl]methyl]phenoxy]-acetic acid The title compound was prepared by the methods of example 89 part (f) and example 89 part (g) using the product of part (a) and the product of example 89 part (e).

MS: APCI (+ve): 453 (M+H).

$^1$H NMR (CDCl$_3$ at 50° C.) δ 7.33-7.21 (3H, m), 7.16 (1H, d), 6.95 (1H, d), 6.83 (2H, m), 4.6 (1H, broad s), 3.71 (1H, d), 3.64 (2H, s), 3.52 (1H, d), 3.45 (1H, broad s), 3.01 (1H, d), 2.88 (1H, d), 2.44 (1H, d), 2.19 (1H, t) and 1.34 (3H, d).

EXAMPLE 91

[4-chloro-2-[[(3S)-4-[(3-fluorophenyl)acetyl]-3-methyl-1-piperazinyl]methyl]phenoxy]-acetic Acid

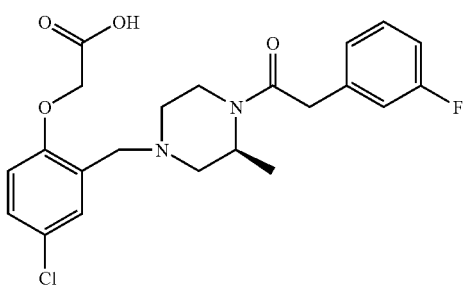 [SMILES: C[C@H]1CN(Cc2cc(Cl)ccc2OCC(=O)O)CCN1C(=O)Cc1cccc(F)c1]

a) 3-fluoro-benzeneacetyl Chloride

The sub-title compound was prepared by the method of example 90 part (a) using 3-fluorophenyl acetic acid.

b) [4-chloro-2-[[(3S)-4-[(3-fluorophenyl)acetyl]-3-methyl-1-piperazinyl]methyl]phenoxy]-acetic Acid The title compound was prepared by the methods of example 89 part (f) and example 2589 part (g) using the product of part (a) and the product of example 89 part (e).

MS: APCI (+ve): 435 (M+H).

$^1$H NMR (CDCl$_3$ at 50° C.) δ 7.33-7.27 (2H, m), 7.16 (1H, d), 7.00-6.86 (4H, m), 3.73 (1H, d), 3.7 (2H, s), 3.55 (1H, d), 3.46 (1H, broad s), 3.01 (1H, d), 2.92 (1H, d), 2.41 (1H, d), 2.15 (1H, t) and 1.34 (3H, d).

EXAMPLE 92

[4-chloro-2-[[(3S)-4-[(3-chlorophenyl)acetyl]-3-methyl-1-piperazinyl]-methyl]phenoxy]-acetic Acid

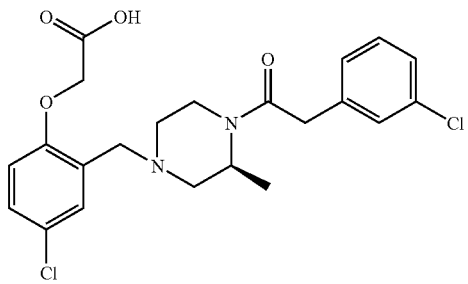 [SMILES: C[C@H]1CN(Cc2cc(Cl)ccc2OCC(=O)O)CCN1C(=O)Cc1cccc(Cl)c1]

a) 3-chloro-benzeneacetyl Chloride

The sub-title compound was prepared by the method of example 90 part (a) using 3-chlorophenyl acetic acid.

b) [4-chloro-2-[[(3S)-4-[(3-chlorophenyl)acetyl]-3-methyl-1-piperazinyl]methyl]phenoxy]-acetic Acid The title compound was prepared by the method of example 89 part (f) and example 89 part (g) using the product of part (a) and the product of example 89 part (e).

MS: APCI (+ve): 451 (M+H).

$^1$H NMR (CDCl$_3$ at 50° C.) δ 7.39-7.15 (6H, m), 6.92 (1H, dd), 4.8 (1H, d), 4.61 (1H, d), 4.57 (1H, broad s), 4.01 (1H, broad s), 3.86 (2H, s), 3.72 (1H, d), 3.51 (1H, d), 3.44 (1H, broad, s), 3.01 (1H, d), 2.94 (1H, d), 2.47 (1H, d), 2.19 (1H, t) and 1.33 (3H, d).

EXAMPLE 93

[4-chloro-2-[[(3S)-4-[(2-chlorophenyl)acetyl]-3-methyl-1-piperazinyl]methyl]phenoxy]-acetic Acid

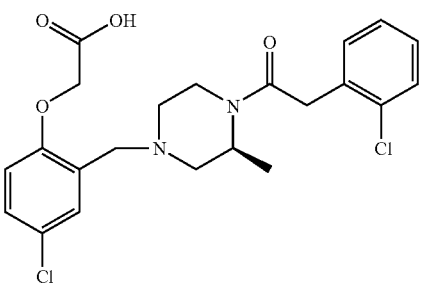 [SMILES: C[C@H]1CN(Cc2cc(Cl)ccc2OCC(=O)O)CCN1C(=O)Cc1ccccc1Cl]

a) 2-chloro-benzeneacetyl Chloride

The sub-title compound was prepared by the method of example 90 part (a) using 2-chlorophenyl acetic acid.

b) [4-chloro-2-[[(3S)-4-[(2-chlorophenyl)acetyl]-3-methyl-1-piperazinyl]methyl]phenoxy]-acetic Acid The title compound was prepared by the methods of example 89 part (f) and example 89 part (g) using the product of part (a) and the product of example 89 part (e).

MS: APCI (+ve): 451 (M+H).

$^1$H NMR (CDCl$_3$ at 50° C.) δ 7.32-7.23 (4H, m), 7.14 (1H, d), 7.1 (1H, t), 6.9 (1H, d), 4.79 (1H, d), 4.59 (1H, d), 4.50 (1H, broad s), 3.97 (1H, broad s), 3.67 (2H, s), 3.67 (1H, d), 3.49 (1H, d), 3.4 (1H, broad s), 2.96 (1H, d), 2.88 (1H, d), 2.37 (1H, d), 2.1 (1H, t) and 1.31 (3H, d).

EXAMPLE 94

[4-chloro-2-[[(3S)-4-[[2-fluoro-4-(trifluoromethyl)phenyl]acetyl]-3-methyl-1-piperazinyl]methyl]phenoxy]-acetic Acid

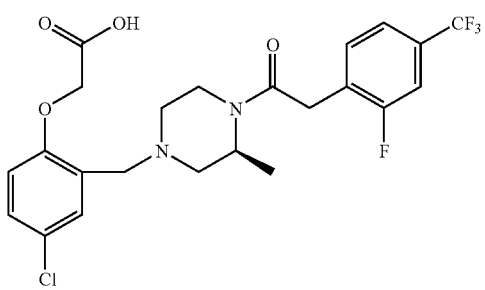 [SMILES: C[C@H]1CN(Cc2cc(Cl)ccc2OCC(=O)O)CCN1C(=O)Cc1ccc(C(F)(F)F)cc1F]

a) 2-fluoro-4-(trifluoromethyl)-benzeneacetyl Chloride

The sub-title compound was prepared by the methods of example 90 part (a) using 2-fluoro-4-trifluoromethylphenyl acetic acid.

b) [4-chloro-2-[[(3S)-4-[[2-fluoro-4-(trifluoromethyl)phenyl]acetyl]-3-methyl-1-piperazinyl]methyl]phenoxy]-acetic Acid The title compound was prepared by the method of example 89 part (f) and example 89 part (g) using the product of part (a) and the product of example 89 part (e).

MS: APCI (+ve): 503 (M+H).

$^1$H NMR (CDCl$_3$ at 50° C.) δ 9.65 (1H, broad, s), 7.39 (2H, m), 7.3 (1H, d), 7.24 (2H, m), 6.84 (1H, d), 4.6 (2H, q), 4.51 (1H, broad, s), 3.99 (1H, d), 3.72 (2H, s), 3.65 (2H, q), 3.38 (1H, t), 2.99 (1H, d), 2.46 (1H, d), 2.26 (1H, t), and 1.33 (3H, d).

EXAMPLE 95

[4-chloro-2-[[(3S)-4-[(3,4-dichlorophenyl)acetyl]-3-methyl-1-piperazinyl]methyl]phenoxy]-acetic Acid

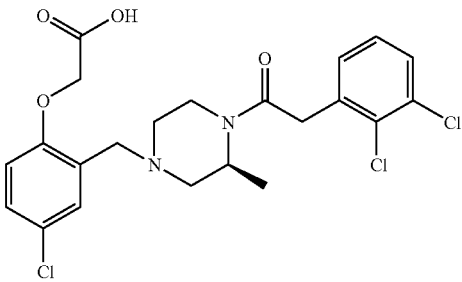 [SMILES: C[C@H]1CN(Cc2cc(Cl)ccc2OCC(=O)O)CCN1C(=O)Cc1cccc(Cl)c1Cl]

a) 3,4-dichloro-benzeneacetyl Chloride

The sub-title compound was prepared by the method of example 90 part (a) using 3,4-dichlorophenyl acetic acid.

b) [4-chloro-2-[[(3S)-4-[(3,4-dichlorophenyl)acetyl]-3-methyl-1-piperazinyl]methyl]phenoxy]-acetic Acid The title compound was prepared by the methods of example 89 part (f) and example 89 part (g) using the product of part (a) and the product of example 89 part (e).

MS: APCI (+ve): 485 (M+H).

$^1$H NMR (CDCl$_3$ at 50° C.) δ 9.45 (1H, m), 7.32 (1H, d), 7.24 (2H, m), 7.06 (1H, dd), 6.86 (1H, d), 4.6 (2H, q), 4.51 (1H, broad, s), 3.97 (1H, broad, s), 3.67 (2H, q), 3.64 (2H, s), 3.39 (1H, broad s), 3.03 (1H, d), 2.51 (1H, d), 2.27 (1H, t), and 1.32 (3H, d).

EXAMPLE 96

[4-chloro-2-[[(3S)-4-[(2,4-dichlorophenyl)acetyl]-3-methyl-1-piperazinyl]methyl]phenoxy]-acetic Acid

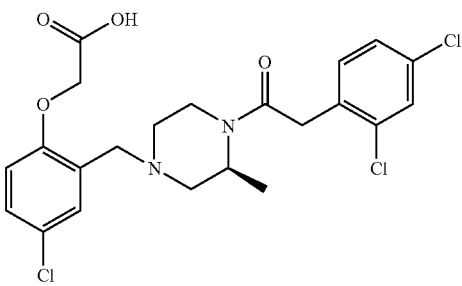 [SMILES: C[C@H]1CN(Cc2cc(Cl)ccc2OCC(=O)O)CCN1C(=O)Cc1ccc(Cl)cc1Cl]

a) 2,4-dichloro-benzeneacetyl Chloride

The sub-title compound was prepared by the method of example 90 part (a) using 2,4-dichlorphenyl acetic acid.

b) [4-chloro-2-[[(3S)-4-[(2,4-dichlorophenyl)acetyl]-3-methyl-1-piperazinyl]methyl]phenoxy]-acetic Acid The title compound was prepared by the methods of example 89 part (f) and example 589 part (g) using the product of part (a) and the product of example 89 part (e).

MS: APCI (+ve): 485 (M+H).

$^1$H NMR (CDCl$_3$ at 50° C.) δ 9.42 (1H, broad s), 7.38 (1H, s), 7.26 (4H, m), 6.88 (1H, d), 4.62 (2H, q), 4.59 (1H, broad s), 3.89 (1H, broad, s), 3.78 (2H, s), 3.73 (2H, q), 3.44 (1H, broad s), 3.05 (1H, d), 2.94 (1H, d), 2.53 (1H, d), 2.32 (1H, t) and 1.36 (3H, d).

EXAMPLE 97

[4-chloro-2-[[(3S)-3-methyl-4-[[4-(trifluoromethyl)phenyl]acetyl]-1-piperazinyl]methyl]phenoxy]-acetic Acid

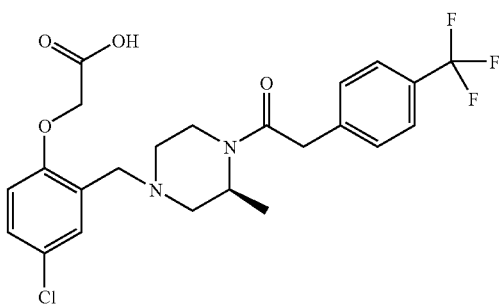 [SMILES: C[C@H]1CN(Cc2cc(Cl)ccc2OCC(=O)O)CCN1C(=O)Cc1ccc(C(F)(F)F)cc1]

a) 4-(trifluoromethyl)-benzeneacetyl Chloride

The sub-title compound was prepared by the method of example 90 part (a) using 4-trifluoromethylphenyl acetic acid.

b) [4-chloro-2-[[(3S)-3-methyl-4-[[4-(trifluoromethyl)phenyl]acetyl]-1-piperazinyl]methyl]phenoxy]-acetic Acid The title compound was prepared by the methods of example 89 part (f) and example 89 part (g) using the product of part (a) and the product of example 89 part (e).

MS: APCI (+ve): 485 (M+H).

$^1$H NMR (CDCl$_3$ at 50° C.) δ 9.35 (1H, broad s), 7.58 (2H, d), 7.26 (2H, m), 7.21 (1H, d), 6.88 (1H, d), 4.62 (2H, q), 4.43 (1H, broad, s), 3.95 (1H, broad s), 3.76 (2H, s), 3.62 (2H, q), 3.4 (1H, broad s), 3.00 (1H, d), 2.9 (1H, d), 2.46 (1H, d), 2.21 (1H, t) and 1.31 (3H, d).

EXAMPLE 98

[4-chloro-2-[[(3S)-3-methyl-4-[(4-methylphenyl)acetyl]-1-piperazinyl]methyl]phenoxy]-acetic Acid

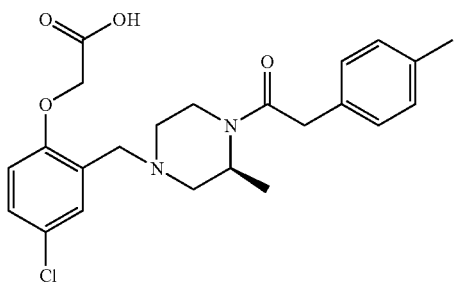 [SMILES: Cc1ccc(CC(=O)N2CCN(Cc3cc(Cl)ccc3OCC(=O)O)C[C@@H]2C)cc1]

a) 4-methyl-benzeneacetyl Chloride

The sub-title compound was prepared by the method of example 90 part (a) using 4-methylphenyl acetic acid.

b) [4-chloro-2-[[(3S)-3-methyl-4-[(4-methylphenyl)acetyl]-1-piperazinyl]methyl]phenoxy]-acetic Acid The title compound was prepared by the method of example 89 part (f) and example 89 part (g) using the product of part (a) and the product of example 89 part (e).

MS: APCI (+ve): 431 (M+H).

$^1$H NMR (CDCl$_3$ at 50° C.) δ 8.6 (1H, broad s), 7.26 (1H, dd), 7.16 (1H, d), 7.1 (4H, m), 6.87 (1H, d), 3.66 (3H, broad s), 3.57 (2H, q), 3.35 (1H, broad s), 2.97 (1H, d), 2.89 (1H, d), 2.41 (1H, broad s), 2.32 (3H, s), 2.12 (1H, t), and 1.28 (3H, d).

EXAMPLE 99

[4-chloro-2-[[(3S)-4-[(4-chloro-2-fluorophenyl)acetyl]-3-methyl-1-piperazinyl]methyl]phenoxy]-acetic Acid

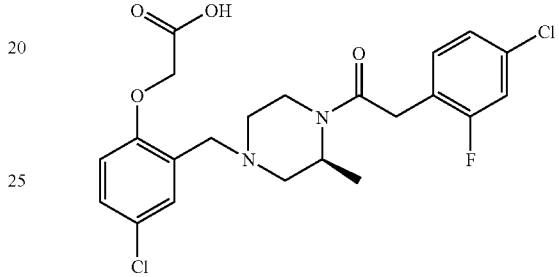

a) 4-chloro-2-fluoro-benzeneacetyl Chloride

The sub-title compound was prepared by the method of example 90 part (a) using 4-chloro-2-fluoro-phenyl acetic acid.

b) [4-chloro-2-[[(3S)-4-[(4-chloro-2-fluorophenyl)acetyl]-3-methyl-1-piperazinyl]methyl]phenoxy]-acetic Acid The title compound was prepared by the method of example 89 part (f) and example 89 part (g) using the product of part (a) and the product of example 89 part (e).

MS: APCI (+ve): 467 (M+H).

$^1$H NMR (CDCl$_3$ at 50° C.) δ 8.96 (1H, broad s), 7.26 (3H, m), 7.09 (2H, m), 6.9 (1H, d), 4.63 (2H, q), 4.5 (1H, broad s), 3.97 (1H, broad s), 3.76 (2H, q), 3.64 (2H, s), 3.44 (1H, broad s), 3.06 (1H, d), 2.93 (1H, d), 2.53 (1H, d), 2.3 (1H, t) and 1.33 (3H; d).

EXAMPLE 100

[4-chloro-2-[[(3S)-4-[(3-fluoro-4-methylphenyl)acetyl]-3-methyl-1-piperazinyl]methyl]phenoxy]-acetic Acid

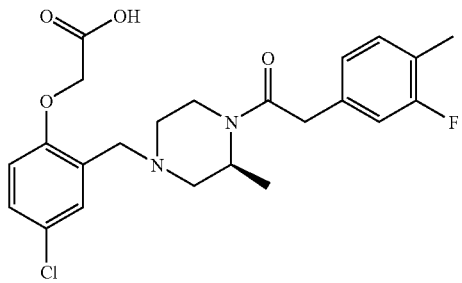 [SMILES: Cc1ccc(CC(=O)N2CCN(Cc3cc(Cl)ccc3OCC(=O)O)C[C@@H]2C)cc1F]

a) 3-fluoro-4-methyl-benzeneacetyl Chloride

The sub-title compound was prepared by the method of example 90 part (a) using 3-fluoro-4-methylphenyl acetic acid.

b) [4-chloro-2-[[(3S)-4-[(3-fluoro-4-methylphenyl)acetyl]-3-methyl-1-piperazinyl]methyl]phenoxy]-acetic Acid The title compound was prepared by the methods of example 89 part (f) and example 89 part (g) using the product of part (a) and the product of example 89 part (e).

MS: APCI (+ve): 449 (M+H).

$^1$H NMR (CDCl$_3$ at 50° C.) δ 8.52 (1H, broad s), 7.24 (2H, m), 7.1 (1H, t), 6.87 (3H, m), 4.6 (2H, q), 4.48 (1H, broad s), 3.97 (1H, broad s), 3.73 (2H, q), 3.64 (2H, s), 3.36 (1H, broad s), 2.99 (1H, d), 2.89 (1H, d), 2.44 (1H, d), 2.24 (3H, s), 2.2 (1H, t) and 1.29 (3H, d).

EXAMPLE 101

[4-chloro-2-[[(3S)-4-[[3-fluoro-4-(trifluoromethyl)phenyl]acetyl]-3-methyl-1-piperazinyl]methyl]phenoxy]-acetic Acid

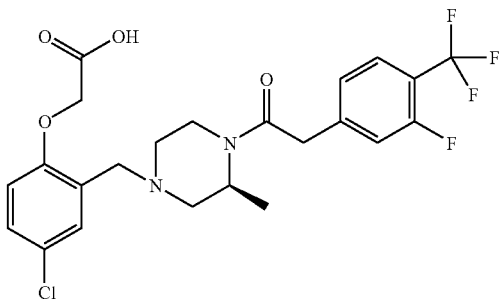 [SMILES: C[C@H]1CN(Cc2cc(Cl)ccc2OCC(=O)O)CCN1C(=O)Cc1ccc(C(F)(F)F)c(F)c1]

a) 3-fluoro-4-(trifluoromethyl)-benzeneacetyl Chloride

The sub-title compound was prepared by the method of example 90 part (a) using 3-fluoro-4-trifluormethylphenyl acetic acid.

b) [4-chloro-2-[[(3S)-4-[[3-fluoro-4-(trifluoromethyl)phenyl]acetyl]-3-methyl-1-piperazinyl]methyl]phenoxy]-acetic Acid The title compound was prepared by the methods of example 89 part (f) and example 89 part (g) using the product of part (a) and the product of example 89 part (e).

MS: APCI (+ve): 449 (M+H).

$^1$H NMR (CDCl$_3$ at 50° C.) δ 7.65 (1H, broad s), 7.54 (1H, t), 7.28 (1H, m), 7.09 (2H, d), 4.6 (2H, q), 6.88 (1H, d), 4.69 (2H, q), 4.5 (1H, broad s), 3.97 (1H, broad s), 3.76 (2H, q), 3.72 (2H, s), 3.44 (1H, broad s), 3.04 (1H, d), 2.89 (1H, d), 2.4 (1H, d), 2.28 (1H, t) and 1.33 (3H, d).

EXAMPLE 102

[4-chloro-2-[[(3S)-3-methyl-4-[[4-(trifluoromethoxy)phenyl]acetyl]-1-piperazinyl]methyl]phenoxy]-acetic Acid

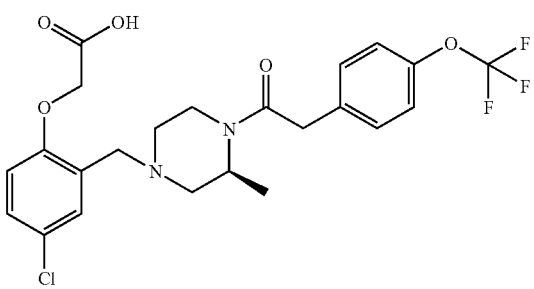 [SMILES: C[C@H]1CN(Cc2cc(Cl)ccc2OCC(=O)O)CCN1C(=O)Cc1ccc(OC(F)(F)F)cc1]

a) 4-(trifluoromethoxy)-benzeneacetyl Chloride

The sub-title compound was prepared by the method of example 90 part (a) using 3-trifluoromethoxyphenyl acetic acid.

b) [4-chloro-2-[[(3S)-3-methyl-4-[[4-(trifluoromethoxy)phenyl]acetyl]-1-piperazinyl]methyl]phenoxy]-acetic Acid The title compound was prepared by the methods of example 89 part (f) and example 89 part (g) using the product of part (a) and the product of example 89 part (e).

MS: APCI (+ve): 499 (M+H).

$^1$H NMR (CDCl$_3$ at 50° C.) δ 8.12 (1H, broad s), 7.24 (6H, m), 6.87 (1H, d), 4.61 (2H, q), 4.49 (1H, broad s), 3.96 (1H, broad s), 3.71 (2H, s), 3.61 (2H, q), 3.4 (1H, broad s), 3.00 (1H, d), 2.89 (1H, d), 2.44 (1H, d), 2.2 (1H, t) and 1.30 (3H, d).

EXAMPLE 103

[4-chloro-2-[[(3S)-4-[2-(4-chlorophenyl)-2-methyl-1-oxopropyl]-3-methyl-1-piperazinyl]methyl]phenoxy]-acetic Acid

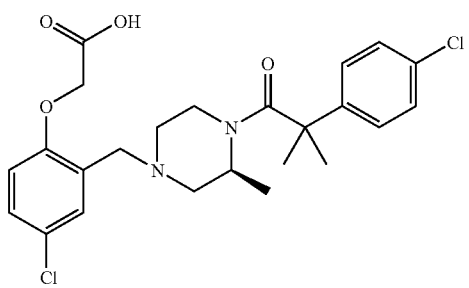 [SMILES: C[C@H]1CN(Cc2cc(Cl)ccc2OCC(=O)O)CCN1C(=O)C(C)(C)c1ccc(Cl)cc1]

a) 4-chloro-α,α-dimethyl-benzeneacetyl Chloride

The sub-title compound was prepared by the method of example 90 part (a) using 4-chloro-α,α-dimethyl-benzeneacetic acid.

b) [4-chloro-2-[[(3S)-4-[2-(4-chlorophenyl)-2-methyl-1-oxopropyl]-3-methyl-1-piperazinyl]methyl]phenoxy]-acetic Acid The title compound was prepared by the methods of example 89 part (f) and example 89 part (g) using the product of part (a) and the product of example 89 part (e).

MS: APCI (−ve): 477 (M−H).

$^1$H NMR (CDCl$_3$ at 50° C.) δ 8.39 (1H, broad s), 7.25 (1H, dd), 7.29 (1H, d), 7.17 (1H, d), 7.14 (1H, d), 6.86 (1H, d), 4.58 (2H, q), 3.62 (2H, q), 3.4 (1H, broad s), 3.13 (1H, t), 2.82 (2H, broad s), 2.45 (1H, broad), 1.99 (1H, broad, s), 1.48 (6H, 2×s) and 1.24 (3H, broad s).

EXAMPLE 104

[4-chloro-2-[[(3S)-4-[(4-methoxyphenyl)acetyl]-3-methyl-1-piperazinyl]methyl]phenoxy]-acetic Acid

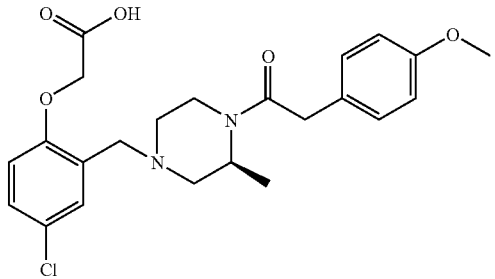 [SMILES: COc1ccc(CC(=O)N2CCN(Cc3cc(Cl)ccc3OCC(=O)O)C[C@@H]2C)cc1]

The title compound was prepared by the methods of example 89 part (f) and example 89 part (g) using the product of example 89 part (e) and 4-methoxy-benzeneacetyl chloride.

MS: APCI (−ve): 447 (M−H).

$^1$H NMR (CDCl$_3$ at 50° C.) δ 8.36 (1H, broad s), 7.24 (2H, m), 7.07 (2H, m), 6.82 (3H, m), 4.58 (2H, q), 4.45 (1H, broad, s), 3.95 (1H, broad s), 3.78 (3H, s), 3.61 (2H, d), 3.59 (2H, q), 3.35 (1H, broad s), 2.97 (1H, d), 2.87 (1H, d), 2.42 (1H, d), 2.16 (1H, t) and 1.28 (3H, d).

EXAMPLE 105

[2-[[(3S)-4-[(4-chlorophenyl)acetyl]-3-methyl-1-piperazinyl]methyl]-4-(trifluoromethyl)phenoxy]-acetic Acid

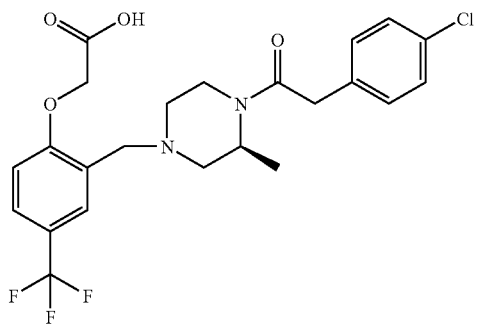 [SMILES: C[C@H]1CN(Cc2cc(C(F)(F)F)ccc2OCC(=O)O)CCN1C(=O)Cc1ccc(Cl)cc1]

a) (2S)-4-[[2-[2-(1,1-dimethylethoxy)-2-oxoethoxy]-5-(trifluoromethyl)phenyl]methyl]-2-methyl-1-piperazinecarboxylic Acid, 1,1-dimethylethyl Ester The sub-title compound was prepared by the method of example 89 part (d) using the products of example 1 part (d) and example 89 part (c).

$^1$H NMR (CDCl$_3$) δ 7.59 (1H, d), 7.53 (1H, dd), 6.83 (1H, d), 4.76 (2H, s), 4.2 (1H, broad s), 3.82 (1H, d), 3.61 (2H, s), 3.13 (1H, t), 2.78 (1H, d), 2.62 (1H, d), 2.09 (2H, m), 1.46 (9H, m) and 1.29 (3H, d).

b) [2-[[(3S)-3-methyl-1-piperazinyl]-methyl]-4-(trifluoromethyl)phenoxy]-acetic acid, 1,1-dimethylethyl Ester, TFA Salt The sub-title compound was prepared by the method of example 89 part (e) using the product of part (a).

c) [2-[[(3S)-4-[(4-chlorophenyl)acetyl]-3-methyl-1-piperazinyl]methyl]-4-(trifluoromethyl)phenoxy]-acetic Acid The title compound was prepared by the methods of examples 89 part (f) and example 89 part (g) using 4-chlorophenylacetyl chloride and the product of part (b).

MS: APCI (−ve): 483 (M−H).

$^1$H NMR (CDCl$_3$) δ 8.87 (1H, broad s), 7.55 (2H, s), 7.26 (2H, d), 7.13 (2H, d), 6.98 (1H, d), 4.67 (2H, q), 4.48 (1H, broad s), 4.00 (1H, broad s), 3.73 (2H, q), 3.66 (2H, s), 3.36 (1H, broad s), 3.00 (1H, d), 2.89 (1H, d), 2.45 (1H, d), 2.25 (1H, d) and 1.31 (3H, d).

EXAMPLE 106

[2-[[(3S)-4-[(4-fluorophenyl)acetyl]-3-methyl-1-piperazinyl]methyl]-4-(trifluoromethyl)phenoxy]-acetic Acid

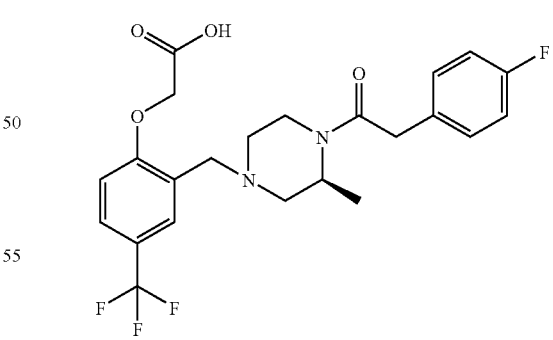

The title compound was prepared by the methods of examples 89 part (f) and example 89 part (g) using 4-chlorophenylacetyl chloride and the product of example 105 part (b).

MS: APCI (−ve): 467 (M−H).

$^1$H NMR (CDCl$_3$) δ 7.54 (2H, m), 7.37 (1H, broad s), 7.16 (2H, m), 6.98 (3H, m), 4.66 (2H, q), 4.61 (1H, broad s), 3.87

(1H, broad s), 3.73 (2H, q), 3.66 (2H, s), 3.36 (1H, broad s), 3.00 (1H, d), 2.90 (1H, d), 2.45 (1H, d), 2.25 (1H, t) and 1.28 (3H, d).

EXAMPLE 107

(2S)-2-[4-chloro-2-[(3S)-4-[(4-chlorophenyl)acetyl]-3-methyl-1-piperazinyl]phenoxy]-propanoic Acid

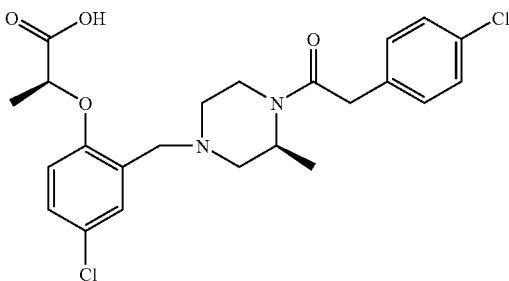 [SMILES: C[C@H](Oc1ccc(Cl)cc1CN1CCN(C(=O)Cc2ccc(Cl)cc2)[C@@H](C)C1)C(=O)O]

a) (2S)-2-(4-chloro-2-formylphenoxy)-propanoic Acid, Methyl Ester

Methyl (R)-(+)-lactate (3.33 g) and acetonitrile (16.7 ml) were charged to a flask and the resulting solution cooled to −5° C. Triethylamine (4.9 ml) was added. Triethylamine hydrochloride (0.31 g) was added. A solution of para-toluenesulfonyl chloride (5.8 g) dissolved in acetonitrile (16.7 ml) was added dropwise to the reaction mixture (over 40 mins), maintaining the temperature below 5° C. After complete addition a precipitate formed which was filtered. The filtrate was diluted further with acetonitrile (55 ml), to give (2R)-2-(4-methylphenoxy)-propanoic acid, methyl ester. The solution was treated with potassium carbonate (5 g) and 5-chloro-2-hydroxy benzaldehyde. The reaction mixture was heated at 50° C. for 32 h, then cooled to 20° C., diluted with water (100 ml) and extracted with tert-butyl methyl ether (250 ml). The organic phase was washed (brine), dried (MgSO$_4$) and concentrated in vacuo. The residue was purified by chromatography (silica, 5-20% EtOAc/hexane as eluent) to give the sub-title compound (5.3 g).

$^1$H NMR (CDCl$_3$) δ 10.49 (1H, s), 7.81 (1H, s), 7.44 (1H, d), 6.8 (1H, d), 4.87 (1H, q), 3.77 (3H, s), and 1.7 (3H, d).

b) (2S)-4-[[5-chloro-2-[(1S)-2-methoxy-1-methyl-2-oxoethoxy]phenyl]methyl]-2-methyl-1-piperazinecarboxylic Acid, 1,1-dimethylethyl Ester The product of part (a) and the product of example 89 part (c) were dissolved in methanol and excess MgSO$_4$ was added. Sodium triacetoxy borohydride (1.5 g) was added. After 2 h further sodium triacetoxy borohydride (1.5 g) was added and stirred for 1 h. Sodium triacetoxy borohydride (0.5 g) was added then, methanol was evaporated in vacuo. The residue was diluted with water and extracted (EtOAc×3), dried (MgSO$_4$) then concentrated in vacuo. Purified by chromatography (silica, using 3:1 hexane/ether as eluent) to give the sub-title compound (0.85 g).

MS: ESI (−ve): 426 (M−H).

$^1$H NMR (CDCl$_3$) δ 7.43 (1H, d), 7.11 (1H, dd), 6.64 (1H, d), 4.74 (1H, q), 4.25-4.16 (1H, m), 3.82 (1H, d), 3.74 (3H, s), 3.53 (2H, s), 3.13 (1H, dt), 2.77 (1H, d), 2.63 (1H, d), 2.24 (1H, dd), 2.1 (1H, dt), 1.61 (3H, d), 1.46 (9H, s) and 1.7 (3H, d).

c) (2S)-2-[4-chloro-2-[[(3S)-3-methyl-1-piperazinyl]methyl]phenoxy]-propanoic Acid, Methyl Ester, TFA Salt The sub-title compound was prepared by the method of example 89 part (e) using the product of part (b).

d) (2S)-2-[4-chloro-2-[[(3S)-4-[(4-chlorophenyl)acetyl]-3-methyl-1-piperazinyl]methyl]phenoxy]-propanoic Acid, Methyl Ester The sub-title compound was prepared by the method of example 89 part (f) using the product of part (c) and 4-chlorophenylacetyl chloride, MS: ESI (+ve): 478 (M+H).

$^1$H NMR (CDCl$_3$) δ 7.4 (1H, s), 7.34-7.25 (2H, m), 7.23-7.07 (3H, m), 6.62 (1H, d), 4.84-4.68 (1H, m), 4.73 (1H, q), 4.43 (1H, d), 4.06 (1H, s), 3.73 (3H, s), 3.68 (2H, s), 3.51 (2H, s), 3.33 (1H, t), 3.01 (1H, t), 2.84 (1H, d), 2.78-2.6 (1H, m), 1.6 (3H, d) and 1.28 (3H, d).

e) (2S)-2-[4-chloro-2-[(3S)-4-[(4-chlorophenyl)acetyl]-3-methyl-1-piperazipyl]phenoxy]-propanoic Acid The product from part d) (50 mg) was dissolved in THF (2 ml) and methanol (2 ml). 1M NaOH (0.1 ml) was added and the reaction mixture was stirred for 2.5 days, then concentrated in vacuo. The residue was triturated with ether to give the title compound (41 mg).

MS: APCI (+ve): 465 (M+H).

$^1$H NMR (DMSO-d6) δ 7.35 (2H, d), 7.3-7.19 (3H, m), 7.11 (1H, dd), 6.74 (1H, d), 4.6-4.48 (1H, m), 4.24-4.1 (2H, m), 3.68 (2H, s), 3.46 (2H, s), 3.32-3.25 (1H, m), 2.96-2.66 (2H, m), 2.13-2 (1H, m), 1.94 (1H, t), 1.33 (3H, d) and 1.26-1.13 (3H, m).

EXAMPLE 108

(2S)-2-[4-chloro-2-[(3S)-4-[(4-fluorophenyl)acetyl]-3-methyl-1-piperazinyl]-phenoxy]-propanoic Acid

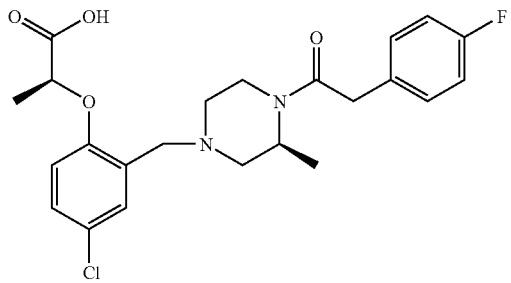 [SMILES: C[C@H](Oc1ccc(Cl)cc1CN1CCN(C(=O)Cc2ccc(F)cc2)[C@@H](C)C1)C(=O)O]

a) (2S)-2-[4-chloro-2-[(3S)-4-[(4-fluorophenyl)acetyl]-3-methyl-1-piperazinyl]phenoxy]-propanoic Acid, Methyl Ester The sub-title compound was prepared by the method of example 89 part (f) using the product of example 107 part (c) and 4-fluorophenylacetyl chloride.

¹H NMR (CDCl₃) δ 7.38 (1H, d), 7.31-7.15 (2H, m), 7.12 (1H, dd), 7.07-6.94 (2H, m), 6.62 (1H, d), 4.87-4.71 (1H, m), 4.73 (1H, qs), 4.00-3.97 (1H, m), 3.91 (3H, s), 3.65-3.51 (2H, m), 3.43-3.27 (1H, m), 2.92-2.61 (2H, m), 2.16-2.06 (1H, m) 1.59 (3H, d) and 1.27 (3H, d).

b) (2S)-2-[4-chloro-2-[(3S)-4-[(4-fluorophenyl)acetyl]-3-methyl-1-piperazinyl]phenoxy]-propanoic Acid The title compound was prepared by the method of example 107 part (e) using the product of part (a).
MS: APCI (+ve): 449 (M+H).
¹H NMR (DMSO-d₆) δ 7.37 (1H, d), 7.24 (3H, dd), 7.12 (2H, t), 6.9 (1H, d), 4.77 (1H, q), 4.63-4.52 (1H, m), 4.27-4.17 (1H, m), 3.81-3.71 (1H, m), 3.68 (2H, s), 3.62-3.49 (2H, m), 2.88-2.72 (2H, m), 2.21 (1H, dd), 2.11-1.99 (1H, m), 1.46 (3H, d) and 1.25-1.13 (3H, m).

EXAMPLE 109

(2S)-2-[4-chloro-2-[[(3S)-3-methyl-4-(phenylacetyl)-1-piperazinyl]methyl]phenoxy]-propanoic Acid

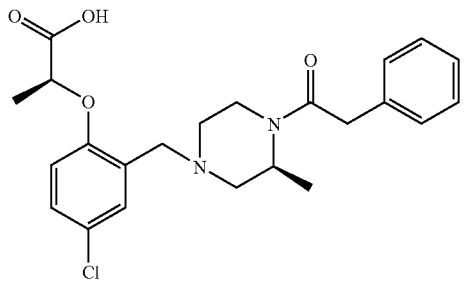 [SMILES: C[C@H](Oc1ccc(Cl)cc1CN1CCN(C(=O)Cc2ccccc2)[C@@H](C)C1)C(=O)O]

a) (3S)-3-methyl-1-piperazinecarboxylic Acid, 1,1-dimethylethyl Ester

Triethylamine (2.85 ml) was added to a solution of (S)-2-methyl piperazine (1 g) in methanol (25 ml) followed by portion wise addition of BOC anhydride (2.18 g). The reaction mixture was stirred for 17 h, concentrated in vacuo. The residue was partitioned between water and ethyl acetate. The organic phase was dried (MgSO₄), and then concentrated in vacuo. The residue was purified by chromatography (silica, ethyl acetate as eluent, then 90:10:1 mixture of ethyl acetate: methanol: ammonia) to give the sub-title compound (1.3 g).
¹H NMR (CDCl₃) δ 4.03-3.85 (2H, m), 2.95 (1H, d), 2.86-2.65 (3H, m), 2.5-2.3 (1H, m), 1.48 (9H, s) and 1.05 (3H, d).

b) (3S)-3-methyl-4-(phenylacetyl)-1-piperazinecarboxylic Acid, 1,1-dimethylethyl Ester The product from part a) (0.734 g), sodium hydrogen carbonate (0.769 g), DCM (6 ml) and water (6 ml) were charged to a flask and stirred vigorously. Phenylacetyl chloride (775 µl) was added dropwise, then stirred for 4 h, diluted with DCM, washed with water, then with brine. The organic fractions were dried (MgSO₄), then concentrated in vacuo to give the sub-title compound (1.07 g).
¹H NMR (CDCl₃) δ 7.32 (2H, t), 7.28-7.18 (3H, m), 4.87-4.76 (1H, m), 4.49-4.38 (1H, m), 4.1-3.92 (1H, m), 3.87-3.68 (2H, m), 3.01-2.81 (2H, m), 2.8-2.68 (1H, m), 2.62-2.5 (1H, m), 1.45 (9H, s) and 1.18-1.05 (3H, m).

c) (2S)-2-methyl-1-(phenylacetyl)-piperazine

TFA (5 ml) was added to a solution of the product from part b) (1.07 g) in DCM (10 ml) and stirred for 1 h. Toluene was added and the reaction mixture was concentrated in vacuo, and then triturated with ether to give the sub-title compound (0.99 g).

d) (2S)-2-[4-chloro-2-[[(3S)-3-methyl-4-(phenylacetyl)-1-piperazinyl]methyl]-phenoxy]-propanoic Acid, Methyl Ester The sub-title compound was prepared by the method of example 107 part (b) using the product of example 107 part (a) (0.25 g) and the product of part c) (0.34 g).
MS: ESI (+ve): 445 (M+H).

e) (2S)-2-[4-chloro-2-[[(3S)-3-methyl-4-(phenylacetyl)-1-piperazinyl]methyl]phenoxy]-propanoic Acid The title compound was prepared by the method of example 107 part (e) using the product of part (d).
MS: APCI (+ve): 431 (M+H).
¹H NMR (DMSO-d6) δ 7.34-7.17 (6H, m), 7.1 (1H, dd), 6.73 (1H, t), 4.6-4.51 (1H, m), 4.24-4.1 (2H, m), 3.73 (1H, d), 3.47-3.33 (2H, m), 3.24-3.15 (1H, m), 2.91-2.59 (3H, m), 2.04 (1H, dd), 1.91 (1H, t), 1.33 (3H, d) and 1.21-1.14 (3H, m).

EXAMPLE 110

(2S)-2-[4-chloro-2-[[(3S)-3-methyl-4-[(4-methylphenyl)acetyl]-1-piperazinyl]methyl]phenoxy]-propanoic Acid

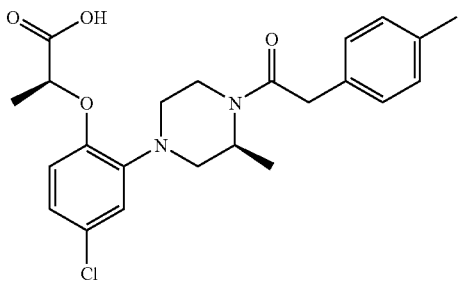 [SMILES: Cc1ccc(CC(=O)N2CCN(c3cc(Cl)ccc3O[C@@H](C)C(=O)O)C[C@@H]2C)cc1]

a) (2S)-2-[4-chloro-2-[[(3S)-3-methyl-4-[(4-methylphenyl)acetyl]-1-piperazinyl]methyl]phenoxy]-propanoic Acid, Methyl Ester The sub-title compound was prepared by the method of example 89 part (f) using the product of example 107 part (c) and 4-methylphenylacetyl chloride.
MS: ESI (+ve): 459 (M+H).

b) (2S)-2-[4-chloro-2-[[(3S)-3-methyl-4-[(4-methylphenyl)acetyl]-1-piperazinyl]methyl]phenoxy]-propanoic Acid The title compound was prepared by the method of example 107 part (e) using the product of part (a). The product was purified by reverse phase HPLC.
MS: APCI (+ve): 445 (M+H).
¹H NMR (DMSO-d6) δ 7.42-7.35 (2H, m), 7.20-7.06 (5H, m), 5-3.9 (3H, m), 3.83-3.67 (3H, m), 3.64-3.39 (2H, m), 3.26-3.03 (2H, m), 2.8-2.66 (2H, m), 2.31 (3H, s), 1.58 (2H, s), 3.62-3.49 (2H, m), 2.88-2.72 (2H, m), 2.21 (1H, dd), 2.11-1.99 (1H, m), 1.46 (3H, d) and 1.41-1.25 (3H, m).

EXAMPLE 111

(2S)-2-[4-chloro-2-[[(3S)-4-[(4-methoxyphenyl)acetyl]-3-methyl-1-piperazinyl]methyl]phenoxy]-propanoic Acid

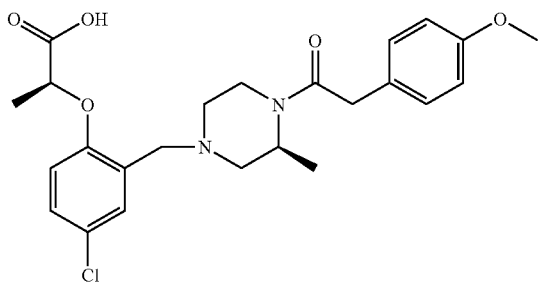 [SMILES: COc1ccc(CC(=O)N2CCN(Cc3cc(Cl)ccc3O[C@@H](C)C(=O)O)C[C@@H]2C)cc1]

a) (2S)-2-[4-chloro-2-[[(3S)-4-[(4-methoxyphenyl)acetyl]-3-methyl-1-piperazinyl]methyl]phenoxy]-propanoic Acid, Methyl Ester The sub-title compound was prepared by the method of example 89 part (f) using the product of example 107 part (c) and 4-methoxylphenylacetyl chloride.
MS: ESI (+ve): 475 (M+H).

b) (2S)-2-[4-chloro-2-[[(3S)-4-[(4-methoxyphenyl)acetyl]-3-methyl-1-piperazinyl]methyl]phenoxy]-propanoic Acid The title compound was prepared by the method of example 107 part (e) using the product of part (a). The product was purified by reverse phase HPLC.
MS: APCI (−ve): 459 (M−H).
$^1$H NMR (CD$_3$OD) δ 7.37 (2H, d), 7.22-7.08 (3H, m), 6.88 (2H, d), 5.03-4.85 (2H, m), 4.59-4.41 (2H, m), 4.02-3.88 (1H, m), 3.76 (3H, s), 3.73 (2H, s), 3.64-3.37 (2H, m), 3.20-3.01 (2H, m), 2.69 (1H, t), 1.57 (3H, d), and 1.38-1.29 (3H, m).

EXAMPLE 112

(2S)-2-[4-chloro-2-[[(3S)-4-[(3,4-dichlorophenyl)acetyl]-3-methyl-1-piperazinyl]methyl]phenoxy]-propanoic Acid

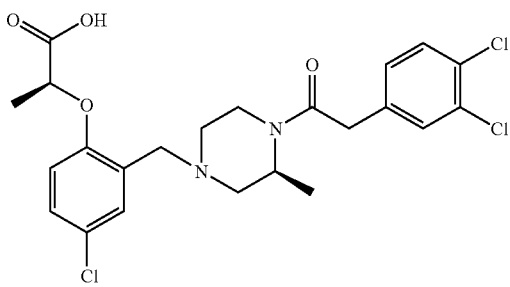 [SMILES: C[C@H](Oc1ccc(Cl)cc1CN1CCN(C(=O)Cc2ccc(Cl)c(Cl)c2)[C@@H](C)C1)C(=O)O]

a) 3,4-dichlorophenyl acetyl chloride

The sub-title compound was prepared by the method of example 90 part (a) using 3,4-dichlorophenyl acetic acid.

b) (2S)-2-[4-chloro-2-[[(3S)-4-[(3,4-dichlorophenyl)acetyl]-3-methyl-1-piperazinyl]methyl]phenoxy]-propanoic Acid, Methyl Ester The sub-title compound was prepared by the method of example 89 part (f) using the product of example 107 part (c) and the product of part (a).
MS: ESI (+ve): 514.9 (M+H).

c) (2S)-2-[4-chloro-2-[[(3S)-4-[(3,4-dichlorophenyl)acetyl]-3-methyl-1-piperazinyl]methyl]phenoxy]-propanoic Acid The title compound was prepared by the method of example 107 part (e) using the product of part (a). The product was purified by reverse phase HPLC.
MS: APCI (−ve): 499 (M−H).
$^1$H NMR (CD$_3$OD) δ 7.49-7.33 (4H, m), 7.22-7.07 (2H, m), 5.03-4.81 (2H, m), 4.59-4.38 (2H, m), 4.03-3.57 (4H, m), 3.54-3.39 (1H, m), 3.13 (2H, d), 2.85-2.68 (1H, m), 1.59 (3H, d), and 1.46-1.33 (3H, m).

EXAMPLE 113

(2S)-2-[4-chloro-2-[[(3S)-3-methyl-4-[[4-(trifluoromethyl)phenyl]acetyl]-1-piperazinyl]methyl]phenoxy]-propanoic Acid

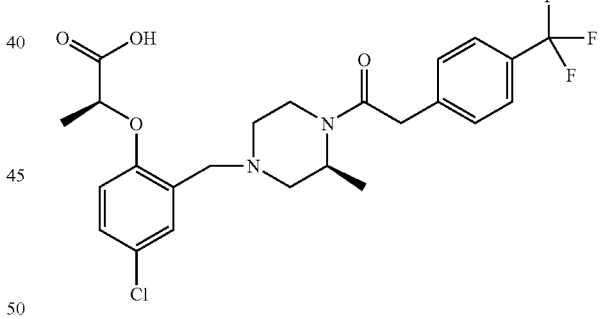

a) 4-(trifluoromethyl)-benzeneacetyl Chloride

The sub-title compound was prepared by the method of example 90 part (a) using 4-trifluoromethylphenyl acetic acid.

b) (2S)-2-[4-chloro-2-[[(3S)-3-methyl-4-[[4-(trifluoromethyl)phenyl]acetyl]-1-piperazinyl]methyl]phenoxy]-propanoic Acid, Methyl Ester The sub-title compound was prepared by the method of example 89 part (f) using the product of example 107 part (c) and the product of part (a).
MS: ESI (+ve): 513 (M+H).

c) (2S)-2-[4-chloro-2-[[(3S)-3-methyl-4-[[4-(trifluoromethyl)phenyl]acetyl]-1-piperazinyl]methyl]phenoxy]-propanoic Acid The title compound was prepared by the method of example 107 part (e) using the product of part (a). The product was purified by reverse phase HPLC.

MS: APCI (−ve): 497 (M−H).

$^1$H NMR (CD$_3$OD) δ 7.63 (2H, d), 7.50-7.34 (4H, m), 7.11 (2H, d), 5.05-4.87 (2H, m), 4.61-4.4 (2H, m), 4.07-3.82 (3H, m), 3.77 (1H, d), 3.72-3.58 (1H, m), 3.14 (2H, d), 2.84-2.69 (1H, m), 1.59 (3H, d) and 1.46-1.39 (3H, d).

EXAMPLE 114

(2S)-2-[4-chloro-2-[(3S)-4-[[2-fluoro-4-(trifluoromethyl)phenyl]acetyl]-3-methyl-1-piperazinyl]methylphenoxy]-propanoic Acid

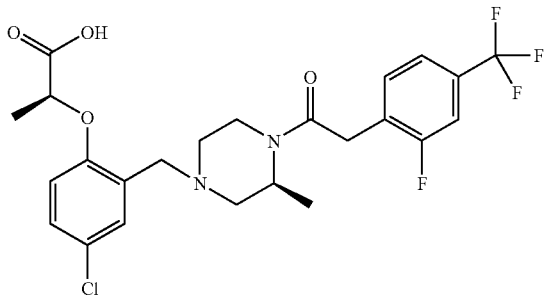 [SMILES: C[C@H](Oc1ccc(Cl)cc1CN1CCN(C(=O)Cc2ccc(C(F)(F)F)cc2F)[C@@H](C)C1)C(=O)O]

a) 2-fluoro-4-(trifluoromethyl)-benzeneacetyl Chloride

The sub-title compound was prepared by the method of example 90 part (a) using 2-fluoro-4-trifluoromethylphenyl acetic acid.

b) (2S)-2-[4-chloro-2-[(3S)-4-[[2-fluoro-4-(trifluoromethyl)phenyl]acetyl]-3-methyl-1-piperazinyl] methylphenoxy]-propanoic Acid Methyl Ester The sub-title compound was prepared by the method of example 89 part (f) using the product of example 107 part (c) and the product of part (a).

MS: ESI (+ve): 531 (M+H).

c) (2S)-2-[4-chloro-2-[(3S)-4-[[2-fluoro-4-(trifluoromethyl)phenyl]acetyl]-3-methyl-1-piperazinyl] methylphenoxy]-propanoic Acid The title compound was prepared by the method of example 107 part (e) using the product of part (a).

MS: APCI (−ve): 515 (M−H).

$^1$H NMR (CD$_3$OD) δ 7.51-7.36 (5H, m), 7.14 (1H, d), 4.97 (1H, q), 4.67-4.41 (2H, m), 4.11-3.98 (1H, m), 3.95-3.86 (2H, m), 3.85-3.7 (2H, m), 3.54 (1H, d), 3.24-3.16 (2H, m), 2.98-2.82 (1H, m), 1.6 (3H, d) and 1.48-1.37 (3H, m).

EXAMPLE 115

(2S)-2-[4-chloro-2-[(3S)-4-[(2,4-dichlorophenyl)acetyl]-3-methyl-1-piperazinyl]methylphenoxy]-propanoic Acid

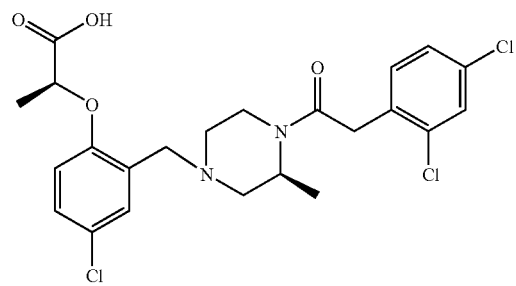 [SMILES: C[C@H](Oc1ccc(Cl)cc1CN1CCN(C(=O)Cc2ccc(Cl)cc2Cl)[C@@H](C)C1)C(=O)O]

a) 2,4-dichloro-benzeneacetyl Chloride

The sub-title compound was prepared by the method of example 90 part (a) using 2,4-dichlorophenyl acetic acid.

b) (2S)-2-[4-chloro-2-[(3S)-4-[(2,4-dichlorophenyl)acetyl]-3-methyl-1-piperazinyl]methylphenoxy]-propanoic Acid, Methyl Ester The sub-title compound was prepared by the method of example 89 part f) using the product of example 107 part c) and the product of part a).

MS: ESI (+ve): 515 (M+H).

c) (2S)-2-[4-chloro-2-[(3S)-4-[(2,4-dichlorophenyl)acetyl]-3-methyl-1-piperazinyl]methylphenoxy]-propanoic Acid The title compound was prepared by the method of example 107 part (e) using the product of part (a). The product was purified by reverse phase HPLC.

MS: APCI (−ve): 499 (M−H).

$^1$H NMR (CD$_3$OD) δ 7.50-7.37 (2H, m), 7.37-7.22 (3H, m), 7.08 (1H, d), 4.99-4.83 (1H, m), 4.06-3.91 (1H, m), 3.90-3.61 (4H, m), 3.50-3.34 (1H, m), 3.14 (1H, d), 3.07 (1H, d), 2.86-2.65 (1H, m), 1.59 (3H, d) and 1.46-1.33 (3H, m).

EXAMPLE 116

(2S)-2-[4-chloro-2-[(3S)-4-[(4-chloro-2-fluorophenyl)acetyl]-3-methyl-1-piperazinyl]methylphenoxy]-propanoic Acid

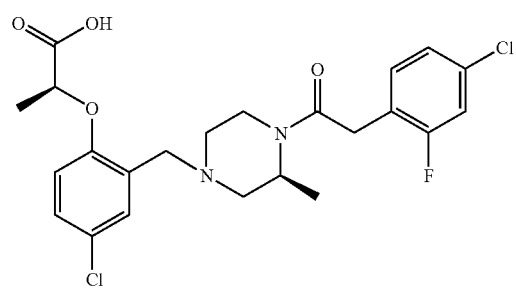 [SMILES: C[C@H](Oc1ccc(Cl)cc1CN1CCN(C(=O)Cc2ccc(Cl)cc2F)[C@@H](C)C1)C(=O)O]

a) 4-chloro-2-fluoro-benzeneacetyl Chloride

The sub-title compound was prepared by the method of example 90 part (a) using 4-chloro-2-fluoro-phenyl acetic acid.

b) (2S)-2-[4-chloro-2-[(3S)-4-[(4-chloro-2-fluorophenyl)acetyl]-3-methyl-1-piperazinyl]methylphenoxy]-propanoic Acid Methyl Ester The sub-title compound was prepared by the method of example 89 part (f) using the product of example 107 part (c) and the product of part (a).
MS: ESI (+ve): 497 (M+H).

c) (2S)-2-[4-chloro-2-[(3S)-4-[(4-chloro-2-fluorophenyl)acetyl]-3-methyl-1-piperazinyl]methylphenoxy]-propanoic Acid The title compound was prepared by the method of example 107 part (e) using the product of part (a).
MS: APCI (–ve): 481 (M–H).
$^1$H NMR (CD$_3$OD) δ 7.41 (1H, d), 7.36 (1H, dd), 7.25 (1H, t), 7.2-7.15 (2H, m), 7.09 (1H, d), 4.98-4.83 (1H, m), 4.6-4.37 (2H, m), 4.04-3.92 (1H, m), 3.89-3.63 (4H, m), 3.49-3.4 (1H, m), 3.19-3.06 (2H, m), 2.89-2.65 (1H, m), 1.59 (3H, d) and 1.50-1.33 (3H, m).

EXAMPLE 117

(2S)-2-[4-chloro-2-[(3S)-3-methyl-4-[[4-(1-methylethyl)phenyl]acetyl]-1-piperazinyl]methylphenoxy]-propanoic Acid

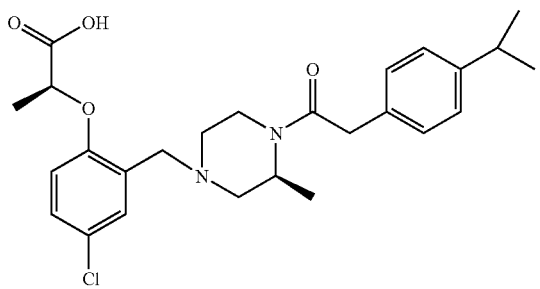 [SMILES: CC(C)c1ccc(CC(=O)N2CCN(Cc3cc(Cl)ccc3O[C@@H](C)C(=O)O)C[C@@H]2C)cc1]

a) 4-(1-methylethyl)-benzeneacetyl chloride

The sub-title compound was prepared by the method of example 90 part (a) using 4-isopropylphenyl acetic acid, used directly without characterisation.

b) (2S)-2-[4-chloro-2-[(3S)-3-methyl-4-[[4-(1-methylethyl)phenyl]acetyl]-1-piperazinyl]methylphenoxy]-propanoic Acid Methyl Ester The sub-title compound was prepared by the method of example 89 part (f) using the product of example 107 part (c) and the product of part (a).
MS: ESI (+ve): 487 (M+H).

c) (2S)-2-[4-chloro-2-[(3S)-3-methyl-4-[[4-(1-methylethyl)phenyl]acetyl]-1-piperazinyl]methylphenoxy]-propanoic Acid The title compound was prepared by the method of example 107 part (e) using the product of part (a). The product was purified by reverse phase HPLC.
MS: APCI (–ve): 471 (M–H).

$^1$H NMR (CD$_3$OD) δ 7.41-7.28 (2H, m), 7.23-7.11 (4H, m), 7.08 (1H, d), 5.02-4.91 (1H, m), 4.59-4.28 (2H, m), 4.00-3.88 (1H, m), 3.82-3.68 (3H, m), 3.63-3.39 (2H, m), 3.13-3.00 (2H, m), 2.92-2.82 (1H, sept), 2.64 (1H, t), 1.57 (3H, d), 1.39-1.27 (3H, m) and 1.22 (6H, d).

EXAMPLE 118

[2-[(3S)-3-methyl-4-(phenylacetyl)-1-piperazinyl]-4-(trifluoromethyl)methylphenoxy]-acetic Acid

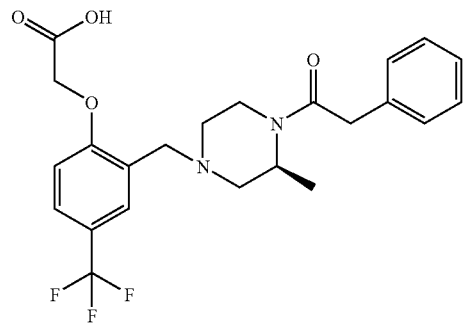 [SMILES: C[C@H]1CN(Cc2cc(C(F)(F)F)ccc2OCC(=O)O)CCN1C(=O)Cc1ccccc1]

The title compound was prepared by the method of example 89 part (d) using the product of example 109 part (c) and the product of example 1 part d). The ester hydrolysis was carried out by the method of example 88 part (f).
MS: APCI (+ve): 451 (M+H)
$^1$H NMR (DMSO-d6) δ 7.71 (1H, s), 7.56 (1H, d), 7.30 (2H, m), 7.21 (3H, m), 7.05 (1H, d), 4.72 (2H, s), 4.56 (1H, m), 4.22 (1H, m), 3.81-3.52 (1H, m), 3.68 (2H, s), 3.56 (2H, s), 3.23 (1H, m), 2.93-2.59 (2H, m), 2.02 (2H, m) and 1.17 (3H, d).

EXAMPLE 119

2-[4-chloro-2-[(3S)-3-methyl-4-(phenylsulfonyl)-1-piperazinyl]methylphenoxy]-2-methyl-propanoic Acid

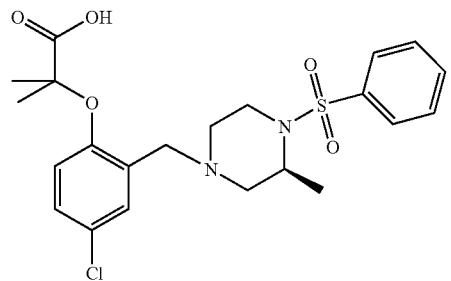 [SMILES: C[C@H]1CN(Cc2cc(Cl)ccc2OC(C)(C)C(=O)O)CCN1S(=O)(=O)c1ccccc1]

a) 2-(4-chloro-2-formylphenoxy)-2-methyl-propanoic Acid, Ethyl Ester 5-chloro-2-hydroxy-benzaldehyde (0.626 g), ethyl-1,2-bromoisobutyrate (0.59 ml), DMF (4 ml) and caesium carbonate (1.3 g) were charged to a flask and heated at 90° C. under nitrogen for 3 h. The reaction mixture was cooled to room temperature then diluted with ethyl acetate, washed with water, sodium hydrogen carbonate, brine, and then dried (MgSO$_4$) and concentrated in vacuo to give the sub-title compound (0.679 g).

$^1$H NMR (CDCl$_3$) δ 10.43 (1H, s), 7.8 (1H, d), 7.39 (1H, dd), 6.76 (1H, d), 4.24 (2H, q), 1.68 (6H, s) and 1.24 (3H, t).

b) 2-[4-chloro-2-[[(3S)-3-methyl-4-(phenylsulfonyl)-1-piperazinyl]methyl phenoxy]-2-methyl-propanoic Acid The products of part a) (0.242 g), the product of example 59 part b) (0.248 g) MgSO$_4$ (0.54 g) and THF (3 ml) were charged to a flask and stirred for 6 h. Sodiumtriacetoxy borohydride (0.57 g) was added and stirred for 16 h. The mixture was partitioned between 2M sodium carbonate and ethyl acetate. The organic layer was dried (MgSO$_4$) then concentrated in vacuo. The residue was purified by SCX resin eluting with acetonitrile, then methanol, finally 7N ammonia in methanol. The basic fractions were concentrated and further purified by chromatography (silica, 50% ether/isohexane as eluent). to give a colourless oil. The oil (92 mg) was dissolved in THF (2 ml) and treated with 6.25 M NaOH (1 ml). The reaction mixture was stirred for 6 days, quenched with 15% acetic acid, extracted with ethyl acetate. The organic phase was dried (MgSO$_4$) then concentrated in vacuo. The residue was purified by reverse phase HPLC to give the title compound (38 mg).

MS: APCI (+ve): 467 (M+H).

$^1$H NMR (DMSO-d6) δ 7.8 (2H, d), 7.63 (3H, m), 7.26 (1H, d), 7.17 (1H, dd), 6.75 (1H, d), 3.99 (1H, m), 3.56 (1H, d), 3.42-3.10 (4H, m), 2.68 (1H, d), 2.00 (1H, dd), 1.89 (1H, td), 1.44 (6H, s) and 1.08 (3H, d).

EXAMPLE 120

[4-chloro-2-[[(3S)-3-(1-methylethyl)-4-(phenylacetyl)-1-piperazinyl]-methyl]phenoxy]-acetic Acid

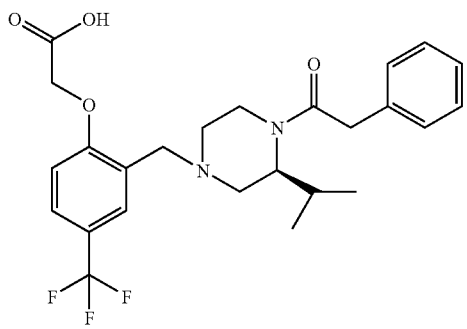 [SMILES: CC(C)[C@H]1CN(Cc2cc(C(F)(F)F)ccc2OCC(=O)O)CCN1C(=O)Cc1ccccc1]

a) (3S)-3-(1-methylethyl)-1-(phenylmethyl)-2,5-piperazinedione

The sub-title compound was prepared by the method of example 69 part (a) using N-Boc-L-valine.

MS: ESI (+ve): 247 (M+H).

$^1$H NMR (DMSO-d6) δ 7.39-7.24 (5H, m), 7.01-6.92 (1H, m), 4.76 (1H, d), 4.46 (1H, d), 3.94 (1H, m), 3.83 (2H, d), 2.47 (1H, m), 1.04 (3H, d) and 0.89 (3H, d).

b) (3S)-3-(1-methylethyl)-1-(phenylmethyl)-piperazine

The sub-title compound was prepared by the method of example 69 part (b) using the product of part (a).

MS: ESI (+ve): 219 (M+H).

c) (2S)-2-(1-methylethyl)-1-(phenylacetyl)-4-(phenylmethyl)-piperazine

The sub-title compound was prepared by the method of example 109 part (b) using the product of part (b).

d) (2S)-2-(1-methylethyl)-1-(phenylacetyl)-piperazine

The sub-title compound was prepared by the method of example 69 part (d) using the product of part (c).

MS: ESI (+ve): 247 (M+H).

e) [4-chloro-2-[[(3S)-(1-methylethyl)-4-(phenylacetyl)-1-piperazinyl]methyl]phenoxy]-acetic Acid The title compound was prepared by the methods of example 89 part (d) and example 88 part (f) using the product of example part (d) and the product of example 13 part (a).

MS: APCI (+ve): 445 (M+H).

$^1$H NMR (DMSO-d6) δ 7.36 (1H, d), 7.28 (1H, d), 7.25 (5H, m), 6.9 (1H, d), 4.61 (2H, s), 4.35-4.07 (1H, m), 3.8-3.44 (2H, m), 3.49 (2H, s), 3.18-2.67 (3H, m), 2.52-2.4 (1H, m), 2.39-2.27 (1H, m), 2.00-1.78 (2H, m), 0.84 (3H, m), and 0.70 (3H, m).

EXAMPLE 121

(2S)-2-[4-chloro-2-[[3-oxo-4-(phenylmethyl)-1-piperazinyl]-methyl]-phenoxy]-propanoic Acid

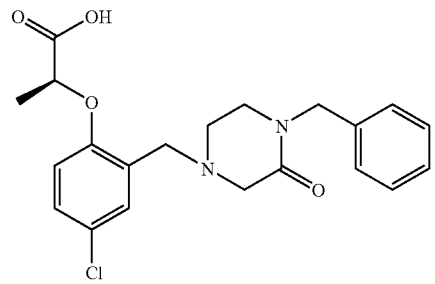 [SMILES: C[C@H](Oc1ccc(Cl)cc1CN1CCN(Cc2ccccc2)C(=O)C1)C(=O)O]

a) 3-oxo-4-(phenylmethyl)-1-piperazinecarboxylic Acid, 1,1-dimethylethyl Ester

Sodium hydride (88 mg, 60% wt.) was added portionwise to a solution of 4-BOC-piperazinone (400 mg) in DMF (10 ml). The reaction mixture was stirred for 1 h, and then benzyl bromide (262 µl) was added dropwise and the mixture stirred at room temp for 16 h. The reaction was quenched with methanol and diluted with water, and then extracted with EtOAC. The organic extracts were concentrated in vacuo and the residue was purified by chromatography (silica, 20% ether/hexane as eluent) to give the sub-title compound (429 mg).

$^1$H NMR (CDCl$_3$) δ 7.37-7.24 (5H, m), 4.63 (2H, s), 4.56 (2H, s), 3.58 (2H, t), 3.25 (2H, t) and 1.46 (9H, s).

b) 1-(phenylmethyl)-2-piperazinone

The product of part a) (420 mg) was stirred in TFA (10 ml) for 30 min, then concentrated in vacuo to give the sub-title compound as an oil (415 mg).

MS: ESI (+ve): 191 (M+H).

c) (2S)-2-[4-chloro-2-[[3-oxo-4-(phenylmethyl)-1-piperazinyl]methyl]phenoxy]-propanoic Acid, Methyl Ester The product of example 107 part (a) (135 mg), the product of part (b) and MgSO$_4$ (xs) in THF (10 ml) were charged to a flask and heated at 50° C. for approximately 16 h. The reaction mixture was cooled to room temperature and sodium triacetoxy borohydride (1 equivalent) added then 0.5 equivalent added after 1 hour. The reaction was stirred for a further 1 hour, then diluted with water, extracted EtOAc (×3), washed (brine), dried (MgSO$_4$) concentrated in vacuo. The residue was purified by chromatography (silica, ether as eluent) to give the sub-title compound (20 mg).

d) (2S)-2-[4-chloro-2-[[3-oxo-4-(phenylmethyl)-1-piperazinyl]methyl]phenoxy]-propanoic Acid The title compound was prepared by the method of example 107 part (e) using the product of part c).
MS: APCI (−ve): 401 (M−H).
$^1$H NMR (CD$_3$OD) δ 7.39 (1H, d), 7.37-7.25 (6H, m), 7.04 (1H, d), 4.9-4.84 (1H, m), 4.65 (2H, q), 4.28 (1H, d), 3.82 (1H, d), 3.72 (1H, d), 3.59 (1H, d), 3.52-3.4 (2H, m), 3.24-3.10 (2H, m) and 1.60 (3H, d).
Pharmacological Data
Ligand Binding Assay
[$^3$H]PGD$_2$ was purchased from Perkin Elmer Life Sciences with a specific activity of 100-210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml 0.1 mM dithiothreitol, 1 mM EDTA, 0.1 mM phenyl methyl sulphonyl fluoride and 100 µg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 µg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 µl of 6.25 nM [$^3$H]PGD$_2$, 20 µl membrane saturated SPA beads both in assay buffer and 10 µl of compound solution or 13,14-dihydro-15-keto prostaglandin D$_2$ (DK-PGD2, for determination of non-specific binding, Cayman chemical company).

Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 µM. Specifically Example 42 has a pIC$_{50}$ value of 6.88, example 7 has a pIC$_{50}$ value of 7.05, example 57 has a pIC$_{50}$ value of 8.3 and example 91 has a pIC$_{50}$ value of 7.8.

The invention claimed is:

1. A compound of formula (I) or a pharmaceutically acceptable salt thereof:

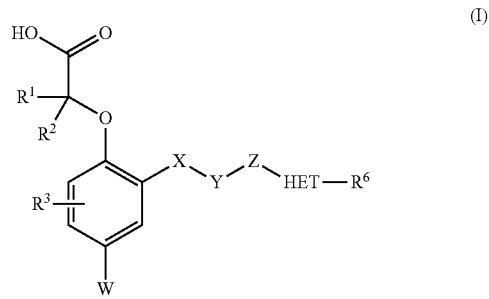

in which:
R$^1$ and R$^2$ independently represent a hydrogen atom, halogen, C$_2$-C$_6$ alkenyl, C$_2$-C$_6$ alkynyl, C$_3$-C$_7$ cycloalkyl or a C$_{1-6}$alkyl group, the latter four groups being optionally substituted by one or more substituents independently selected from halogen, C$_3$-C$_7$ cycloalkyl, NR$^9$R$^{10}$, OR$^8$, S(O)$_n$R$^7$ (where n is 0, 1 or 2);
or
R$^1$ and R$^2$ together can form a 3-8 membered ring optionally containing one or more atoms selected from O, S, NR$^{11}$ and itself optionally substituted by one or more C$_1$-C$_3$ alkyl or halogen;
W is halogen, cyano, nitro, SO$_2$R$^7$, SO$_2$NR$^9$R$^{10}$, OR$^8$, or C$_{1-6}$alkyl, the latter being optionally substituted by one or more substituents independently selected from halogen, OR$^8$ and NR$^7$R$^8$, S(O)$_n$R$^5$ where n is 0, 1 or 2;
R$^3$ is one or more substituents independently selected from hydrogen, halogen, CN, nitro, SO$_2$R$^7$, OR$^8$, SR$^7$, SOR$^7$, SO$_2$NR$^9$R$^{10}$, CONR$^9$R$^{10}$, NR$^9$R$^{10}$, NR$^{11}$SO$_2$R$^7$, NR$^{11}$CO$_2$R$^7$, NR$^{11}$COR$^7$ or C$_{1-6}$alkyl, the latter being optionally substituted by one or more substituents independently selected from halogen, OR$^8$ and NR$^9$R$^{10}$, S(O)$_n$R$^7$ where n is 0, 1 or 2;
X represents a bond, or C$_1$-C$_6$ alkyl, optionally substituted by one or more substituents independently selected from halogen, C$_1$-C$_6$ alkyl the latter being optionally substituted by one or more substituents independently selected from halogen, OR$^6$ and NR$^7$R$^8$, S(O)$_n$R$^5$ where n is 0, 1 or 2;
Y represents a diamine of the following type:—

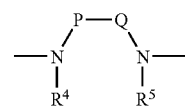

R$^4$ and R$^5$ independently represent hydrogen, SO$_2$R$^7$, C(O)R$^7$, CO$_2$R$^7$ and C$_1$-C$_6$ alkyl, the latter being optionally substituted by one or more substituents independently selected from aryl, heteroaryl, halogen, $OR^8$ and $NR^9R^{10}$, $S(O)_nR^7$ where n is 0, 1 or 2;

$R^4$ and $R^5$ are joined together or one of $R^4$ and $R^5$ is joined onto P or Q to form a saturated heterocyclic 3-10 membered ring with, 1 or 2 endocyclic nitrogen atoms;

P and Q independently represent, $C_1$-$C_6$ alkyl optionally substituted by one or more substituents independently selected from (=O), halogen, $OR^8$ and $NR^9R^{10}$, $S(O)_nR^7$ (where n is 0, 1 or 2), $C_1$-$C_6$ alkyl, $C_3$-$C_6$ cycloalkyl, aryl or heteroaryl (the latter two being optionally substituted by one or more substituents independently selected from halogen, $OR^8$ and $NR^9R^{10}$, $CONR^9R^{10}$, $S(O)_nR^7$ where n is 0, 1 or 2);

Z represents a bond, $(CR^{12})_n$—C(O), $(CR^{12})_n$—$S(O)_n$, $C(O)(CR^{12})_n$, or $S(O)_2(CR^{12})_n$, $S(O)_2N(CR^{12})n$, where n=0, 1 or 2;

HET represents aryl or heteroaryl;

$R^6$ represents one or more substituents independently selected from hydrogen, halogen, CN, nitro, $COR^7$, $CO_2R^8$, $SO_2R^7$, $OR^8$, $SR^8$, $SOR^7$, $SO_2NR^9R^{10}$, $CONR^9R^{10}$, $NR^9R^{10}$, $NR^8SO_2R^7$, $NR^8CO_2R^8$, $NR^8COR^7$, $NR^8CONR^9R^{10}$, $NR^8SO_2NR^9R^{10}$, aryl, heteroaryl, $C_2$-$C_6$ alkenyl, $C_2$-$C_6$ alkynyl, $C_3$-$C_7$ cycloalkyl or $C_{1-6}$alkyl, the latter four groups being optionally substituted by one or more substituents independently selected from halogen, $C_3$-$C_7$ cycloalkyl, CN, $OR^8$, $NR^9R^{10}$, $S(O)_nR^7$ (where n is 0, 1 or 2), $CONR^9R^{10}$, $NR^8COR^7$, $SO_2NR^9R^{10}$ and $NR^8SO_2R^7$;

$R^7$ represents a $C_1$-$C_6$ alkyl, an aryl or a heteroaryl group all of which may be optionally substituted by halogen atoms, $OR^8$, $NR^{14}R^{15}$;

$R^8$ represents hydrogen, $C_1$-$C_6$, alkyl, an aryl or a heteroaryl group all of which may be optionally substituted by halogen atoms, $OR^8$, $NR^{14}R^{15}$;

$R^9$ and $R^{10}$ independently represent hydrogen, $C_3$-$C_7$ cycloalkyl or $C_{1-6}$alkyl, the latter two groups being optionally substituted by one or more substituents independently selected from halogen, $C_3$-$C_7$ cycloalkyl, $OR^6$ and $NR_{14}R^{15}$, $S(O)_nR^6$ (where n=0, 1 or 2), $CONR^7R^8$, $NR^6COR^7$, $SO_2NR^7R^8$ and $NR^6SO_2R^5$;

or $R^9$ and $R^{10}$ together with the nitrogen atom to which they are attached can form a 3-8 membered saturated heterocylic ring optionally containing one or more atoms selected from 0, $S(O)_n$ (where n=0, 1 or 2), $NR^{13}$, and itself optionally substituted by halogen or $C_{1-3}$ alkyl;

$R^{11}$ represents a hydrogen atom, $C(O)R^9$, $C_1$-$C_6$ alkyl an aryl or a heteroaryl group (the latter three can be optionally substituted by halogen);

$R^{12}$ reperesents one or more from hydrogen, or a $C_{1-6}$alkyl group, the latter being optionally substituted by one or more substituents independently selected from halogen, $C_3$-$C_7$ cycloalkyl, $NR^{14}R^{15}$, $OR^8$, $S(O)_nR^7$ (where n is 0, 1 or 2);

$R^{13}$ represent hydrogen, $C_{1-4}$ alkyl, —$COC_1$-$C_4$ alkyl, $COYC_1$-$C_4$alkyl where Y is O or $NR^7$; and $R^{14}$ and $R^{15}$ independently represent hydrogen, $C_{1-4}$ alkyl;

or $R^{14}$ and $R^{15}$ together with the nitrogen atom to which they are attached can form a 3-8 membered saturated heterocylic ring optionally containing one or more atoms selected from 0, $S(O)_n$ (where n=0, 1 or 2), $NR^{13}$, and itself optionally substituted by halogen or $C_{1-3}$ alkyl.

2. A compound according to claim 1 in which Y is piperazine, alkyl substituted piperazine piperazinone, imidazolidine, homopiperazine, aminopyrrolidine, aminoazetidine, or aminopiperidine.

3. A compound according to claim 1 in which W is halogen, $CF_3$, CN or $C_1$-$C_6$alkyl.

4. A compound according to claim 1 in which $R^1$ and $R^2$ are independently hydrogen or methyl.

5. A compound according to claim 1 in which $R^3$ is hydrogen or halogen.

6. A compound according to claim 1 in which X is a bond or $CH_2$.

7. A compound according to claim 1 in which the group Z is $SO_2$, $SO_2CH_2$, $C(O)CH_2$ $C(O)C(Me)_2$, C(O) or C(O)$CH_2CH_2$.

8. A compound according to claim 1 in which $R^6$ is one or more substituents selected from halogen, hydrogen, $C_1$-$C_6$ alkyl optionally substituted by one or more halogen atoms, alkoxy optionally substituted by halogen atoms, nitro, cyano or $SO_2$alkyl.

9. A compound according to claim 1 selected from:

[2-[4-[(4-Fluorophenypsulfonyl]-1-piperazinyl]-4-(trifluoromethyl)phenoxy]-acetic acid;

[2-[[4-(phenylsulfonyl)-1-piperazinyl]methyl]-4-(trifluoromethyl)phenoxy]-acetic acid;

[2-[4-[[(4-cyanophenyesulfonyl]-1-piperazinylmethyl]]-4-(trifluoromethyl)phenoxy]-acetic acid;

[2-[[4-[(2-fluorophenyl)sulfonyl]-1-piperazinyl]methyl]-4-(trifluoromethyl)phenoxy]-acetic acid;

[2-[[4-[(2-methylphenyl)sulfonyl]-1-piperazinyl]methyl]-4-(trifluoromethyl)phenoxy]-acetic acid;

[2-[[4-[(4-nitrophenyl)sulfonyl]-1-piperazinyl]methyl]-4-(trifluoromethyl)phenoxy]-acetic acid;

[2-[[4-[(4-fluorophenyl)sulfonyl]hexahydro-1H-1,4-diazepin-1-yl]methyl]-4-(trifluoromethyl)phenoxy]-acetic acid;

[2-[hexahydro-4-[[(4-methoxyphenyl)sulfonyl]-1H-1,4-diazepin-1-yl]methyl]-4-(trifluoromethyl)phenoxy]-acetic acid;

[2-[[hexahydro-4-(phenylsulfonyl)-1H-1,4-diazepin-1-yl]methyl]-4-(trifluoromethyl)phenoxy]-acetic acid;

[2-[[4-[(4-cyanophenyl)sulfonyl]hexahydro-1H-1,4-diazepin-1-yl]methyl]-4-(trifluoromethyl)phenoxy]-acetic acid;

[4-chloro-2-[4-(phenylsulfonyl)-1-piperazinyl]phenoxy]-acetic acid;

[4-chloro-2-[[4-[(4-fluorophenyl)sulfonyl]-1-piperazinyl]methyl]phenoxy]-acetic acid;

[4-chloro-2-[[4-[(4-chlorophenyl)sulfonyl]-1-piperazinyl]methyl]phenoxy]-acetic acid;

[4-chloro-2-[[4-[[4-(trifluoromethyl)phenyl]methyl]sulfonyl]-1-piperazinyl]phenoxy]-acetic acid;

[4-chloro-2-[[4-[[4-(trifluoromethoxy)phenyl]methyl]sulfonyl]-1-piperazinyl]phenoxy]-acetic acid;

[4-chloro-2-[4-[[[4-(methylsulfonyl)phenyl]sulfonyl]-1-piperazinyl]methyl]phenoxy]-acetic acid;

[4-chloro-2-[[4-[(3-fluorophenyl)sulfonyl]-1-piperazinyl]methyl]phenoxy]-acetic acid;

[4-chloro-2-[[4-[[3-(trifluoromethyl)phenyl]sulfonyl]-1-piperazinyl]methyl]phenoxy]-acetic acid;

[4-chloro-2-[[4-[(3-chlorophenyl)sulfonyl]-1-piperazinyl]methyl]phenoxy]-acetic acid;

[4-chloro-2-[[4-[[3-(trifluoromethoxy)phenyl]sulfonyl]-1-piperazinyl]methyl]phenoxy]-acetic acid;

[4-chloro-2-[[4-[[3-(difluoromethoxy)phenyl]sulfonyl]-1-piperazinyl]methyl]phenoxy]-acetic acid;

[4-chloro-2-[[4-[(3-chloro-4-fluorophenyl)sulfonyl]-1-piperazinyl]methyl]phenoxy]-acetic acid;
[4-chloro-2-[[4-[(3,4-dichlorophenyl)sulfonyl]-1-piperazinyl]methyl]phenoxy]-acetic acid;
[4-chloro-2-[[4-[(3,4-difluorophenyl)sulfonyl]-1-piperazinyl]methyl]phenoxy]-acetic acid;
[4-chloro-2-[[4-[(phenylmethyl)sulfonyl]-1-piperazinyl]methyl]phenoxy]-acetic acid;
[4-chloro-2-[[4-[[(2-nitrophenyl)methyl]sulfonyl]-1-piperazinyl]methyl]phenoxy]-acetic acid;
[4-chloro-2-[[4-[[(3-chlorophenyl)methyl]sulfonyl]-1-piperazinyl]methyl]phenoxy]-acetic acid;
[4-chloro-2-[[4-[[(4-chlorophenyl)methyl]sulfonyl]-1-piperazinyl]methyl]phenoxy]-acetic acid;
[2-[[4-(phenylacetyl)-1-piperazinyl]methyl]-4-(trifluoromethyl)phenoxy]-acetic acid;
[4-Chloro-2-[[4-[(4-chlorophenyl)acetyl]-1-piperazinyl]methyl]phenoxy]-acetic acid;
[4-Chloro-2-[[4-(1-oxo-3-phenylpropyl)-1-piperazinyl]methyl]phenoxy]-acetic acid;
[3-Chloro-2-[[4-[(4-chlorophenypacetyl]-1-piperazinyl]methyl]phenoxy]-acetic acid;
[2-Chloro-2-[[4-[(4-chlorophenypacetyl]-1-piperazinyl]methyl]phenoxy]-acetic acid;
[4-chloro-2-[1-[4-(phenylsulfonyl)-1-piperazinyl]ethyl]phenoxy]-acetic acid trifluoroacetate salt;
[2-[1-(4-benzoyl-1-piperazinyl)ethyl]-4-chlorophenoxy]-acetic acid, trifluoroacetate salt;
[4-chloro-2-[[[1-[(phenylmethyl)sulfonyl]-3pyrrolidinyl]amino]methyl]phenoxy]-acetic acid;
[4-chloro-2-[[[1-(phenylsulfonyl)-3-pyrrolidinyl]amino]methyl]phenoxy]-acetic acid;
[4-chloro-2-[4-(phenylsulfonyl)-1-piperazinyl]phenoxy]-acetic acid;
[4-chloro-2-[4-[(phenylmethyl)sulfonyl]-1-piperazinyl]phenoxy]-acetic acid;
[4-chloro-2-[4-(phenylacetyl)-1-piperazinyl]phenoxy]-acetic acid;
[2-[(4-benzoyl-1-piperazinyl)methyl]-4-(trifluoromethyl)phenoxy]-acetic acid;
[2-[[4-(2-thienylacetyl)-1-piperazinyl]methyl]-4-(trifluoromethyl)phenoxy]-acetic acid;
[4-Chloro-2-[[4-[[(4-fluorophenyl)methyl]sulfonyl]-1-piperazinyl]methyl]phenoxy]acetic acid;
[4-Chloro-2-[[4-[[(4-methylphenyl)methyl]sulfonyl]-1-piperazinyl]methyl]phenoxy]acetic acid;
[4-Chloro-2-[[4-[[(3-methylphenyl)methyl]sulfonyl]-1-piperazinyl]methyl]phenoxy]acetic acid;
[4-Chloro-2-[[4-[(2-pyridinylmethyl)sulfonyl]-1-piperazinyl]methyl]phenoxy]acetic acid;
[4-Chloro-2-[[4-[(3-pyridinylmethyl)sulfonyl]-1-piperazinyl]methyl]phenoxy]acetic acid;
[4-Chloro-2-[[4-[(4-methylphenyl)acetyl]-1-piperazinyl]methyl]phenoxy]acetic acid;
[4-Chloro-2-[[4-[(4-fluorophenyl)acetyl]-1-piperazinyl]methyl]phenoxy]acetic acid;
[4-Chloro-2-[[4-[(4-methoxyphenyl)acetyl]-1-piperazinyl]methyl]phenoxy]acetic acid;
[4-Chloro-2-[[4-(3-pyridinylacetyl)-1-piperazinyl]methyl]phenoxy]acetic acid;
[4-Chloro-2-[[4-[(4-cyanophenyl)acetyl]-1-piperazinyl]methyl]phenoxy]acetic acid;
[4-Chloro-2-[[2-methyl-4-(phenylsulfonyl)-1-piperazinyl]methyl]phenoxy]acetic acid;
[4-Chloro-2-[[2-methyl-4-[(phenylmethyl)sulfonyl]-1-piperazinyl]methyl]phenoxy]acetic acid;
[4-Chloro-2-[[(2R)-2-methyl-4-(phenylsulfonyl)-1-piperazinyl]methyl]phenoxy]acetic acid;
[4-Chloro-2-[[3-methyl-4-[(phenylmethyl)sulfonyl]-1-piperazinyl]methyl]phenoxy]acetic acid;
[4-Chloro-2-[[3-methyl-4-(phenylsulfonyl)-1-piperazinyl]methyl]phenoxy]acetic acid;
[4-Chloro-2-[[3-methyl-4-(phenylacetyl)-1-piperazinyl]methyl]phenoxy]acetic acid;
[4-Chloro-2-[[(3S)-3-methyl-4-(phenylsulfonyl)-1-piperazinyl]methyl]phenoxy]acetic acid;
[4-Chloro-2-[[(3R)-3-methyl-4-(phenylsulfonyl)-1-piperazinyl]methyl]phenoxy]acetic acid;
[4-Chloro-2-[[(3R)-3-methyl-4-[(phenylmethyl)sulfonyl]-1-piperazinyl]methyl]phenoxy]acetic acid;
[4-Chloro-2-[[(3S)-3-methyl-4-[(phenylmethyl)sulfonyl]-1-piperazinyl]methyl]phenoxy]acetic acid;
[4-Chloro-2-[[(3R)-3-methyl-4-(phenylacetyl)-1-piperazinyl]methyl]phenoxy]acetic acid;
[4-Chloro-2-[[(3S)-3-methyl-4-(phenylacetyl)-1-piperazinyl]methyl]phenoxy]acetic acid;
c) [4-Chloro-2-[[(3S)-3-methyl-4-(phenylacetyl)-1-piperazinyl]methyl]phenoxy]acetic acid;
[4-Chloro-2-[[(3S)-4-[(4-chlorophenyl)acetyl]-3-methyl 1-piperazinyl]methyl]phenoxy]acetic acid;
[2-[(4-Benzoyl-3-methyl-1-piperazinyl)methyl]-4-chlorophenoxy]acetic acid;
[4-chloro-2-[[2,5-dimethyl-4-(phenylacetyl)-1-piperazinyl]methyl]phenoxy]acetic acid;
[4-Chloro-2-[[4-(1-oxo-2-phenylpropyl)-1-piperazinyl]methyl]phenoxy]-acetic acid;
[4-Chloro-2-[[(3S)-3-ethyl-4-(phenylsulfonyl)-1-piperazinyl]methyl]phenoxy]acetic acid;
[4-chloro-2-[[(3S)-3-ethyl-4-(phenylacetyl)-1-piperazinyl]methyl]phenoxy]-acetic acid;
(Cis)-[4-chloro-2-[[2,3-dimethyl-4-(phenylacetyl)-1-piperazinyl]methyl]phenoxy]-acetic acid;
[4-chloro-2-[[(3S)-4-(phenylsulfonyl)-3-propyl-1-piperazinyl]methyl]phenoxy]-acetic acid;
[4-Chloro-2-[[(3S)-4-(phenylacetyl)-3-propyl-1-piperazinyl]methyl]phenoxy]acetic acid;
[4-chloro-2-[[(3R,5S)-3,5-dimethyl-4-(phenylacetyl)-1-piperazinyl]methyl]phenoxy]-acetic acid;
[4-chloro-2-[[hexahydro-4-(phenylsulfonyl)-1H-1,4-diazepin-1-yl]methyl]phenoxy]-acetic acid;
[4-chloro-2-[[hexahydro-4-[(phenylmethyl)sulfonyl]-1H-1,4-diazepin-1-yl]methyl]phenoxy]-acetic acid;
[4-chloro-2-[[hexahydro-4-(phenylacetyl)-1H-1,4-diazepin-1-yl]methyl]phenoxy]-acetic acid;
[4-Fluoro-2-[4-(phenyl)acetyl-1-piperazinyl]methyl]phenoxy]-acetic acid;
[4-Fluoro-2-[[4-[(phenyl)sulfonyl]-1-piperazinyl]methyl]phenoxy]-acetic acid;
[4-Fluoro-2-[[4-[(phenylmethyl)sulfonyl]-1-piperazinyl]methyl]phenoxy]-acetic acid;
(2S)-2-[4-fluoro-2-[[4-(phenylacetyl)-1-piperazinyl]methyl]phenoxy]-propanoic acid;
(2S)-2-[4-fluoro-2-[[4-(phenylsulfonyl)-1-piperazinyl]methyl]phenoxy]-propanoic acid;
(2S)-2-[4-fluoro-2-[[4-[(phenylmethyl)sulfonyl]-1-piperazinyl]methyl]phenoxy]-propanoic acid;
[4-chloro-2-[[methyl[1-(phenylsulfonyl)-3-pyrrolidinyl]amino]methyl]phenoxy]-acetic acid;
[4-Cyano-2-[[(3S)-3-methyl-4-(phenylacetyl)-1-piperazinyl]methyl]phenoxy]acetic acid;
[4-Methyl-2-[[(3S)-3-methyl-4-(phenylacetyl)-1-piperazinyl]methyl]phenoxy]acetic acid;

[2-[[(3S)-3-Methyl-4-(phenylacetyl)-1-piperazinyl]methyl]-4-(trifluoromethyl)phenoxy]acetic acid;
[4-(1-methylethyl)-2-[[4-(phenylsulfonyl)-1piperazinyl]methyl]phenoxy]acetic acid;
[4-chloro-2-[[(3S)-4-[(4-fluorophenyl)acetyl]-3-methyl-1-piperazinyl]methyl]phenoxy]-acetic acid;
[4-chloro-2-[[(3S)-4-[(2,4-difluorophenyl)acetyl]-3-methyl-1-piperazinyl]methyl]phenoxy]-acetic acid;
[4-chloro-2-[[(3S)-4-[(3-fluorophenyl)acetyl]-3-methyl-1-piperazinyl]methyl]phenoxy]-acetic acid;
[4-chloro-2-[[(3S)-4-[(3-chlorophenyl)acetyl]-3-methyl-1-piperazinyl]methyl]phenoxy]-acetic acid;
[4-chloro-2-[[(3S)-4-[(2-chlorophenyl)acetyl]-3-methyl-1-piperazinyl]methyl]phenoxy]-acetic acid;
[4-chloro-2-[[3S)-4-[[2-fluoro-4-(trifluoromethyl)phenyl]acetyl]-3-methyl-1-piperazinyl]methyl]phenoxy]-acetic acid;
[4-chloro-2-[[(3S)-4-[(3,4-dichlorophenyl)acetyl]-3-methyl-1-piperazinyl]methyl]phenoxy]-acetic acid;
[4-chloro-2-[[(3S)-4-[(2,4-dichlorophenyl)acetyl]-3-methyl-1-piperazinyl]methyl]phenoxy]-acetic acid;
[4-chloro-2-[[(3S)-3-methyl-4-[[4-(trifluoromethyl)phenyl]acetyl]-1-piperazinyl]methyl]phenoxy]-acetic acid;
[4-chloro-2-[[(3S)-3-methyl-4-[(4-methylphenyl)acetyl]-1-piperazinyl]methyl]phenoxy]-acetic acid;
[4-chloro-2-[[(3S)-4-[(4-chloro-2-fluorophenyl)acetyl]-3-methyl-1-piperazinyl]methyl]phenoxy]-acetic acid;
[4-chloro-2-[[(3S)-4-[(3-fluoro-4-methylphenyl)acetyl]-3-methyl-1-piperazinyl]methyl]phenoxy]-acetic acid;
[4-chloro-2-[[(3S)-4-[[3-fluoro-4-(trifluoromethyl)phenyl]acetyl]-3-methyl-1-piperazinyl]methyl]phenoxy]-acetic acid;
[4-chloro-2-[[(3S)-3-methyl-4-[[4-(trifluoromethoxy)phenyl]acetyl]-1-piperazinyl]methyl]phenoxy]-acetic acid;
[4-chloro-2-[[(3S)-4-[2-(4-chlorophenyl)-2-methyl-1-oxopropyl]-3-methyl-1-piperazinyl]methyl]phenoxy]-acetic acid;
[4-chloro-2-[[(3S)-4-[(4-methoxyphenyl)acetyl]-3-methyl-1-piperazinyl]methyl]phenoxy]-acetic acid;
[2-[[(3S)-4-[(4-chlorophenyl)acetyl]-3-methyl-1-piperazinyl]methyl]-4-(trifluoromethyl)phenoxy]-acetic acid;
[2-[[(3S)-4-[(4-fluorophenyl)acetyl]-3-methyl-1-piperazinyl]methyl]-4-(trifluoromethyl)phenoxy]-acetic aci
(2S)-2-[4-chloro-2-[(3S)-4-[(4-chlorophenyl)acetyl]-3-methyl-1-piperazinyl]phenoxy]-propanoic acid;
(2S)-2-[4-chloro-2-[(3S)-4-[(4-fluorophenyl)acetyl]-3-methyl-1-piperazinyl]phenoxy]-propanoic acid;
(2S)-2-[4-chloro-2-[[(3S)-3-methyl-4-(phenylacetyl)-1-piperazinyl]methyl]phenoxy]-propanoic acid;
(2S)-2-[4-chloro-2-[[(3S)-3-methyl-4-[(4-methylphenyl)acetyl]-1-piperazinyl]methyl]phenoxy]-propanoic acid;
(2S)-2-[4-chloro-2-[[(3S)-4-[(4-methoxyphenyl)acetyl]-3-methyl-1-piperazinyl]methyl]phenoxy]-propanoic acid;
(2S)-2-[4-chloro-2-[[(3S)-4-[(3,4-dichlorophenyl)acetyl]-3-methyl-1-piperazinyl]methyl]phenoxy]-propanoic acid;
(2S)-2-[4-chloro-2-[[(3S)-3-methyl-4-[[4-(trifluoromethyl)phenyl]acetyl]-1-piperazinyl]methyl]phenoxy]-propanoic acid;
(2S)-2-[4-chloro-2-[(3S)-4-[[2-fluoro-4-(trifluoromethyl)phenyl]acetyl]-3-methyl-1-piperazinyl]methylphenoxy]-propanoic acid;
(2S)-2-[4-chloro-2-[(3S)-4-[(2,4-dichlorophenyl)acetyl]-3-methyl-1-piperazinyl]methylphenoxy]-propanoic acid;
(2S)-2-[4-chloro-2-[(3S)-4-[(4-chloro-2-fluorophenyl)acetyl]-3-methyl-1-piperazinyl]methylphenoxy]-propanoic acid;
(2S)-2-[4-chloro-2-[(3S)-3-methyl-4-[[4-(1-methylethyl)phenyl]acetyl]-1-piperazinyl]methylphenoxy]-propanoic acid;
[2-[(3S)-3-methyl-4-(phenylacetyl)-1-piperazinyl]-4-(trifluoromethyl)methylphenoxy]-acetic acid;
2-[4-chloro-2-[(3S)-3-methyl-4-(phenylsulfonyl)-1-piperazinyl]methylphenoxy]-2-methyl-propanoic acid;
[4-chloro-2-[[(3S)-3-(1-methylethyl)-4-(phenylacetyl)-1-piperazinyl]methyl]phenoxy]-acetic acid; and
(2S)-2-[4-chloro-2-[[3-oxo-4-(phenylmethyl)-1-piperazinyl]methyl]phenoxy]-propanoic acid;
and pharmaceutically acceptable salts thereof.

10. A method for the therapeutic treatment of asthma in a patient, which comprises administering to the patient a therapeutically effective amount of a compound of formula (I), or a pharmaceutically acceptable salt thereof, as claimed in claim 1.

11. A method for the therapeutic treatment of rhinitis in a patient, which comprises administering to the patient a therapeutically effective amount of a compound of formula (I), or a pharmaceutically acceptable salt thereof, as claimed in claim 1.

* * * * *